United States Patent
Reiley

(10) Patent No.: US 12,004,961 B2
(45) Date of Patent: Jun. 11, 2024

(54) APPARATUS, SYSTEMS, AND METHODS FOR THE FIXATION OR FUSION OF BONE

(71) Applicant: SI-Bone Inc., Santa Clara, CA (US)

(72) Inventor: Mark A. Reiley, Delray Beach, FL (US)

(73) Assignee: SI-Bone Inc., Santa Clara, CA (US)

( * ) Notice: Subject to any disclaimer, the term of this patent is extended or adjusted under 35 U.S.C. 154(b) by 344 days.

(21) Appl. No.: 16/930,174

(22) Filed: Jul. 15, 2020

(65) Prior Publication Data
US 2020/0345507 A1 Nov. 5, 2020

Related U.S. Application Data

(63) Continuation of application No. 15/952,102, filed on Apr. 12, 2018, now abandoned, which is a
(Continued)

(51) Int. Cl.
  *A61F 2/44* (2006.01)
  *A61B 17/16* (2006.01)
  (Continued)

(52) U.S. Cl.
  CPC .......... *A61F 2/447* (2013.01); *A61B 17/1615* (2013.01); *A61B 17/1659* (2013.01);
  (Continued)

(58) Field of Classification Search
  CPC .......... A61F 2/4455; A61F 2002/30622; A61F 2/46; A61F 2/4601; A61F 2/4644; A61F 2002/4677
  (Continued)

(56) References Cited

U.S. PATENT DOCUMENTS

| 1,951,278 A | * | 3/1934 | Ericsson | A61B 17/7283 606/67 |
| 2,136,471 A | * | 11/1938 | Schneider | A61B 17/72 411/487 |

(Continued)

FOREIGN PATENT DOCUMENTS

| CN | 1128944 A | 8/1996 |
| CN | 1190882 A | 8/1998 |

(Continued)

OTHER PUBLICATIONS

Reckling et al.; U.S. Appl. No. 17/116,903 entitled "Sacro-iliac joint stabilizing implants and methods of implantation," filed Dec. 9, 2020.

(Continued)

*Primary Examiner* — Eduardo C Robert
*Assistant Examiner* — Christina Negrellirodriguez
(74) *Attorney, Agent, or Firm* — Shay Glenn LLP

(57) ABSTRACT

Assemblies of one or more implant structures make possible the achievement of diverse interventions involving the fusion and/or stabilization of the SI-joint and/or lumbar and sacral vertebra in a non-invasive manner, with minimal incision, and without the necessitating the removing the intervertebral disc. The representative lumbar spine interventions, which can be performed on adults or children, include, but are not limited to, SI-joint fusion or fixation; lumbar interbody fusion; translaminar lumbar fusion; lumbar facet fusion; trans-iliac lumbar fusion; and the stabilization of a spondylolisthesis.

13 Claims, 42 Drawing Sheets

Related U.S. Application Data continuation of application No. 15/195,955, filed on Jun. 28, 2016, now Pat. No. 9,949,843, which is a continuation-in-part of application No. 14/274,486, filed on May 9, 2014, now Pat. No. 9,486,264, and a continuation-in-part of application No. 13/858,814, filed on Apr. 8, 2013, now Pat. No. 9,375,323, said application No. 14/274,486 is a continuation of application No. 13/786,037, filed on Mar. 5, 2013, now Pat. No. 8,734,462, said application No. 13/858,814 is a continuation of application No. 12/960,831, filed on Dec. 6, 2010, now Pat. No. 8,414,648, said application No. 13/786,037 is a continuation of application No. 12/924,784, filed on Oct. 5, 2010, now Pat. No. 8,388,667, said application No. 12/960,831 is a continuation-in-part of application No. 11/136,141, filed on May 24, 2005, now Pat. No. 7,922,765, said application No. 12/924,784 is a continuation-in-part of application No. 11/136,141, filed on May 24, 2005, now Pat. No. 7,922,765.

(51) Int. Cl.
*A61B 17/68* (2006.01)
*A61B 17/70* (2006.01)
*A61B 17/86* (2006.01)
*A61B 17/17* (2006.01)
*A61F 2/00* (2006.01)
*A61F 2/28* (2006.01)
*A61F 2/30* (2006.01)
*A61F 2/42* (2006.01)

(52) U.S. Cl.
CPC ...... *A61B 17/1664* (2013.01); *A61B 17/1671* (2013.01); *A61B 17/68* (2013.01); *A61B 17/7055* (2013.01); *A61B 17/866* (2013.01); *A61B 17/8685* (2013.01); *A61F 2/4455* (2013.01); *A61F 2/446* (2013.01); *A61B 17/1637* (2013.01); *A61B 17/1757* (2013.01); *A61B 17/864* (2013.01); *A61F 2/0077* (2013.01); *A61F 2/28* (2013.01); *A61F 2002/30062* (2013.01); *A61F 2002/30156* (2013.01); *A61F 2002/30179* (2013.01); *A61F 2002/3023* (2013.01); *A61F 2002/30235* (2013.01); *A61F 2002/30405* (2013.01); *A61F 2002/305* (2013.01); *A61F 2002/30576* (2013.01); *A61F 2002/30604* (2013.01); *A61F 2002/30622* (2013.01); *A61F 2/30767* (2013.01); *A61F 2002/30777* (2013.01); *A61F 2002/30785* (2013.01); *A61F 2002/30787* (2013.01); *A61F 2002/3082* (2013.01); *A61F 2002/30841* (2013.01); *A61F 2002/3085* (2013.01); *A61F 2002/30995* (2013.01); *A61F 2002/4238* (2013.01); *A61F 2/4465* (2013.01); *A61F 2002/448* (2013.01); *A61F 2210/0004* (2013.01); *A61F 2220/0025* (2013.01); *A61F 2230/0023* (2013.01); *A61F 2230/0058* (2013.01); *A61F 2230/0069* (2013.01); *A61F 2310/00017* (2013.01); *A61F 2310/00023* (2013.01); *A61F 2310/00029* (2013.01); *A61F 2310/00131* (2013.01); *A61F 2310/00179* (2013.01); *A61F 2310/00329* (2013.01); *A61F 2310/00796* (2013.01); *A61F 2310/0097* (2013.01)

(58) Field of Classification Search
USPC ......... 606/60, 246, 279, 95, 96, 98, 99, 104; 623/17.11–17.16; 128/898
See application file for complete search history.

(56) References Cited

U.S. PATENT DOCUMENTS

| | | | |
|---|---|---|---|
| 2,243,717 A | 5/1941 | Moreira | |
| 2,414,882 A | 7/1947 | Longfellow | |
| 2,562,419 A | 7/1951 | Ferris | |
| 2,675,801 A | 4/1954 | Bambara et al. | |
| 2,697,433 A | 12/1954 | Zehnder | |
| 3,076,453 A | 2/1963 | Tronzo | |
| 3,506,982 A | 4/1970 | Steffee | |
| 3,694,821 A | 10/1972 | Moritz | |
| 3,709,218 A | 1/1973 | Halloran | |
| 3,744,488 A | 7/1973 | Cox | |
| 4,059,115 A | 11/1977 | Jumashev et al. | |
| 4,156,943 A | 6/1979 | Collier | |
| 4,197,645 A | 4/1980 | Scheicher | |
| 4,292,964 A | 10/1981 | Ulrich | |
| 4,341,206 A | 7/1982 | Perrett et al. | |
| 4,344,190 A | 8/1982 | Lee et al. | |
| 4,399,813 A | 8/1983 | Barber | |
| 4,423,721 A | 1/1984 | Otte et al. | |
| 4,475,545 A * | 10/1984 | Ender | A61B 17/7283 606/64 |
| 4,501,269 A | 2/1985 | Bagby | |
| 4,569,338 A | 2/1986 | Edwards | |
| 4,612,918 A * | 9/1986 | Slocum | A61D 9/00 606/279 |
| 4,622,959 A | 11/1986 | Marcus | |
| 4,630,601 A * | 12/1986 | Harder | A61B 17/7208 606/62 |
| 4,638,799 A | 1/1987 | Moore | |
| 4,657,550 A | 4/1987 | Daher | |
| 4,743,256 A * | 5/1988 | Brantigan | A61F 2/447 128/898 |
| 4,773,402 A | 9/1988 | Asher et al. | |
| 4,787,378 A | 11/1988 | Sodhi | |
| 4,790,303 A * | 12/1988 | Steffee | A61B 17/7022 606/86 R |
| 4,834,757 A | 5/1989 | Brantigan | |
| 4,846,162 A | 7/1989 | Moehring | |
| 4,877,019 A | 10/1989 | Vives | |
| 4,878,915 A | 11/1989 | Brantigan | |
| 4,898,186 A * | 2/1990 | Ikada | A61L 31/06 606/77 |
| 4,904,261 A | 2/1990 | Dove et al. | |
| 4,950,270 A | 8/1990 | Bowman et al. | |
| 4,961,740 A | 10/1990 | Ray et al. | |
| 4,969,888 A | 11/1990 | Scholten et al. | |
| 4,981,481 A | 1/1991 | Kranz et al. | |
| 5,034,011 A | 7/1991 | Howland | |
| 5,034,013 A | 7/1991 | Kyle et al. | |
| 5,035,697 A | 7/1991 | Frigg | |
| 5,041,118 A | 8/1991 | Wasilewski | |
| 5,053,035 A | 10/1991 | McLaren | |
| 5,059,193 A | 10/1991 | Kuslich | |
| 5,066,296 A | 11/1991 | Chapman et al. | |
| 5,098,434 A | 3/1992 | Serbousek | |
| 5,102,414 A | 4/1992 | Kirsch | |
| 5,108,397 A | 4/1992 | White | |
| 5,122,141 A | 6/1992 | Simpson et al. | |
| 5,139,498 A | 8/1992 | Astudillo Ley | |
| 5,139,500 A | 8/1992 | Schwartz | |
| 5,147,367 A | 9/1992 | Ellis | |
| 5,147,402 A | 9/1992 | Bohler et al. | |
| 5,190,551 A | 3/1993 | Chin et al. | |
| 5,197,961 A | 3/1993 | Castle | |
| 5,242,444 A | 9/1993 | MacMillan | |
| 5,298,254 A | 3/1994 | Prewett et al. | |
| 5,334,205 A | 8/1994 | Cain | |
| 5,380,325 A | 1/1995 | Lahille et al. | |
| 5,390,683 A | 2/1995 | Pisharodi | |
| 5,433,718 A | 7/1995 | Brinker | |
| 5,443,466 A | 8/1995 | Shah | |
| 5,458,638 A | 10/1995 | Kuslich et al. | |
| 5,470,334 A | 11/1995 | Ross et al. | |
| 5,480,402 A | 1/1996 | Kim | |
| 5,569,249 A | 10/1996 | James et al. | |

(56) References Cited

U.S. PATENT DOCUMENTS

| | | |
|---|---|---|
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A | 6/1998 | Perry |
| 5,766,252 A | 6/1998 | Henry et al. |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,030,162 A | 2/2000 | Huebner et al. |
| 6,053,916 A | 4/2000 | Moore |
| 6,056,749 A | 5/2000 | Kuslich |
| 6,066,175 A | 5/2000 | Henderson et al. |
| 6,086,589 A | 7/2000 | Kuslich et al. |
| 6,096,080 A * | 8/2000 | Nicholson ......... A61B 17/1604 623/17.16 |
| 6,120,292 A | 9/2000 | Buser et al. |
| 6,120,504 A | 9/2000 | Brumback et al. |
| 6,143,031 A | 11/2000 | Knothe et al. |
| 6,197,062 B1 | 3/2001 | Fenlin |
| 6,206,924 B1 | 3/2001 | Timm |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Michelson |
| 6,306,140 B1 | 10/2001 | Siddiqui |
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,551,343 B1 * | 4/2003 | Tormala ............. A61B 17/064 606/154 |
| 6,556,857 B1 | 4/2003 | Estes et al. |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,582,467 B1 | 6/2003 | Teitelbaum et al. |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,712,852 B1 | 3/2004 | Chung et al. |
| 6,723,099 B1 | 4/2004 | Goshert |
| 6,723,100 B2 | 4/2004 | Biedermann et al. |
| 6,740,118 B2 | 5/2004 | Eisermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,989,033 B1 | 1/2006 | Schmidt |
| 6,991,461 B2 | 1/2006 | Gittleman |
| 6,993,406 B1 | 1/2006 | Cesarano et al. |
| 7,018,416 B2 | 3/2006 | Hanson et al. |
| 7,118,579 B2 | 10/2006 | Michelson |
| 7,147,666 B1 | 12/2006 | Grisoni |
| 7,175,663 B1 | 2/2007 | Stone |
| 7,211,085 B2 | 5/2007 | Michelson |
| 7,223,269 B2 | 5/2007 | Chappuis |
| 7,314,488 B2 | 1/2008 | Reiley |
| 7,335,205 B2 | 2/2008 | Aeschlimann et al. |
| 7,338,500 B2 | 3/2008 | Chappuis |
| 7,396,365 B2 | 7/2008 | Michelson |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,608,097 B2 | 10/2009 | Kyle |
| 7,608,098 B1 | 10/2009 | Stone et al. |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,846,162 B2 | 12/2010 | Nelson et al. |
| 7,850,732 B2 | 12/2010 | Heinz |
| 7,857,832 B2 | 12/2010 | Culbert et al. |
| 7,887,565 B2 | 2/2011 | Michelson |
| 7,892,265 B2 | 2/2011 | Perez-Cruet et al. |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,142,481 B2 | 3/2012 | Warnick |
| 8,202,305 B2 * | 6/2012 | Reiley ................. A61B 17/864 606/279 |
| 8,268,099 B2 | 9/2012 | O'Neill et al. |
| 8,308,779 B2 | 11/2012 | Reiley |
| 8,308,783 B2 | 11/2012 | Morris et al. |
| 8,317,862 B2 | 11/2012 | Troger et al. |
| 8,348,950 B2 | 1/2013 | Assell et al. |
| 8,350,186 B2 | 1/2013 | Jones et al. |
| 8,388,667 B2 * | 3/2013 | Reiley ................ A61B 17/8695 606/301 |
| 8,394,129 B2 | 3/2013 | Morgenstern Lopez |
| 8,398,635 B2 | 3/2013 | Vaidya |
| 8,414,648 B2 * | 4/2013 | Reiley ................ A61B 17/1615 606/279 |

(56) References Cited

U.S. PATENT DOCUMENTS

| | | |
|---|---|---|
| 8,425,570 B2 * | 4/2013 | Reiley .................. A61B 17/866 606/279 |
| 8,430,930 B2 | 4/2013 | Hunt |
| 8,444,693 B2 * | 5/2013 | Reiley .................. A61F 2/4455 623/17.11 |
| 8,449,585 B2 | 5/2013 | Wallenstein et al. |
| 8,467,851 B2 | 6/2013 | Mire et al. |
| 8,470,004 B2 * | 6/2013 | Reiley ................ A61B 17/1671 606/279 |
| 8,475,505 B2 | 7/2013 | Nebosky et al. |
| 8,529,608 B2 | 9/2013 | Terrill et al. |
| 8,608,802 B2 | 12/2013 | Bagga et al. |
| D697,209 S | 1/2014 | Walthall et al. |
| 8,641,737 B2 | 2/2014 | Matthis et al. |
| 8,663,332 B1 | 3/2014 | To et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,845,693 B2 | 9/2014 | Smith et al. |
| 8,858,601 B2 | 10/2014 | Reiley |
| 8,920,477 B2 * | 12/2014 | Reiley ................ A61B 17/1615 606/279 |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,979,911 B2 | 3/2015 | Martineau et al. |
| 8,986,348 B2 * | 3/2015 | Reiley .................. A61B 17/863 606/279 |
| RE45,484 E | 4/2015 | Foley et al. |
| 9,039,743 B2 | 5/2015 | Reiley |
| 9,044,321 B2 | 6/2015 | Mauldin et al. |
| 9,060,876 B1 | 6/2015 | To et al. |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,198,676 B2 | 12/2015 | Pilgeram et al. |
| 9,220,535 B2 | 12/2015 | Röbling et al. |
| 9,314,348 B2 | 4/2016 | Emstad |
| 9,358,057 B1 | 6/2016 | Whipple et al. |
| 9,375,243 B1 | 6/2016 | Vestgaarden |
| 9,375,323 B2 | 6/2016 | Reiley |
| 9,445,852 B2 | 9/2016 | Sweeney |
| 9,451,999 B2 | 9/2016 | Simpson et al. |
| 9,452,065 B1 | 9/2016 | Lawson |
| 9,486,264 B2 * | 11/2016 | Reiley ..................... A61B 17/68 |
| 9,492,201 B2 | 11/2016 | Reiley |
| 9,498,264 B2 | 11/2016 | Harshman et al. |
| 9,510,872 B2 | 12/2016 | Donner et al. |
| 9,517,095 B2 | 12/2016 | Vaidya |
| 9,526,548 B2 | 12/2016 | Asfora |
| 9,554,909 B2 | 1/2017 | Donner |
| 9,561,063 B2 | 2/2017 | Reiley |
| 9,566,100 B2 | 2/2017 | Asfora |
| 9,603,613 B2 | 3/2017 | Schoenefeld et al. |
| 9,603,644 B2 | 3/2017 | Sweeney |
| 9,615,856 B2 | 4/2017 | Arnett et al. |
| 9,622,783 B2 * | 4/2017 | Reiley ................ A61B 17/1615 |
| 9,655,656 B2 | 5/2017 | Whipple |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,763,695 B2 | 9/2017 | Mirda |
| 9,820,789 B2 | 11/2017 | Reiley |
| 9,826,986 B2 | 11/2017 | Donner et al. |
| 9,839,448 B2 | 12/2017 | Reckling et al. |
| 9,848,892 B2 | 12/2017 | Biedermann et al. |
| 9,936,983 B2 | 4/2018 | Mesiwala et al. |
| 9,949,776 B2 | 4/2018 | Mobasser et al. |
| 9,949,843 B2 | 4/2018 | Reiley et al. |
| 9,956,013 B2 * | 5/2018 | Reiley ................ A61B 17/1615 |
| 9,993,276 B2 | 6/2018 | Russell |
| 10,004,547 B2 | 6/2018 | Reiley |
| 10,058,430 B2 | 8/2018 | Donner et al. |
| 10,166,033 B2 | 1/2019 | Reiley et al. |
| 10,194,962 B2 | 2/2019 | Schneider et al. |
| 10,201,427 B2 | 2/2019 | Mauldin et al. |
| 10,219,885 B2 | 3/2019 | Mamo et al. |
| 10,258,380 B2 | 4/2019 | Sinha |
| 10,271,882 B2 | 4/2019 | Biedermann et al. |
| 10,335,217 B2 | 7/2019 | Lindner |
| 10,363,140 B2 | 7/2019 | Mauldin et al. |
| 10,426,533 B2 | 10/2019 | Mauldin et al. |
| 10,492,921 B2 | 12/2019 | McShane, III et al. |
| 10,531,904 B2 | 1/2020 | Kolb |
| 10,653,454 B2 | 5/2020 | Frey et al. |
| 10,653,544 B2 | 5/2020 | Forsell |
| 10,729,475 B2 | 8/2020 | Childs |
| 10,743,995 B2 | 8/2020 | Fallin et al. |
| 10,758,283 B2 | 9/2020 | Frey et al. |
| 10,799,367 B2 | 10/2020 | Vrionis et al. |
| 10,806,597 B2 | 10/2020 | Sournac et al. |
| 10,842,634 B2 | 11/2020 | Pasini et al. |
| 10,932,838 B2 | 3/2021 | Mehl et al. |
| D972,137 S | 12/2022 | Schifano et al. |
| 11,571,245 B2 | 2/2023 | Stuart et al. |
| 11,607,251 B2 | 3/2023 | Albert et al. |
| 11,607,256 B1 | 3/2023 | Folsom et al. |
| 11,672,664 B2 | 6/2023 | Mauldin et al. |
| 11,752,011 B2 | 9/2023 | Stuart et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |
| 2002/0038123 A1 | 3/2002 | Visotsky et al. |
| 2002/0049497 A1 * | 4/2002 | Mason ..................... A61F 2/447 623/17.11 |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0120335 A1 | 8/2002 | Angelucci et al. |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0088251 A1 | 5/2003 | Braun et al. |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kustich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |

(56) References Cited

U.S. PATENT DOCUMENTS

| | | |
|---|---|---|
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0037319 A1 | 2/2005 | Bulard et al. |
| 2005/0049590 A1 | 3/2005 | Alleyne et al. |
| 2005/0055023 A1 | 3/2005 | Sohngen et al. |
| 2005/0070905 A1 | 3/2005 | Donnelly et al. |
| 2005/0071004 A1 | 3/2005 | Re et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0113919 A1 | 5/2005 | Cragg et al. |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1* | 7/2005 | Zucherman ........ A61B 17/1671 623/17.11 |
| 2005/0159749 A1 | 7/2005 | Levy et al. |
| 2005/0159812 A1 | 7/2005 | Dinger et al. |
| 2005/0165398 A1 | 7/2005 | Reiley |
| 2005/0192572 A1 | 9/2005 | Abdelgany et al. |
| 2005/0216082 A1 | 9/2005 | Wilson et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0273101 A1 | 12/2005 | Schumacher |
| 2005/0277940 A1 | 12/2005 | Neff |
| 2006/0036247 A1 | 2/2006 | Michelson |
| 2006/0036251 A1* | 2/2006 | Reiley ................ A61B 17/8625 606/301 |
| 2006/0036252 A1 | 2/2006 | Baynham et al. |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0085068 A1* | 4/2006 | Barry ..................... G09B 23/30 606/279 |
| 2006/0089656 A1 | 4/2006 | Allard et al. |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241600 A1 | 10/2006 | Ensign et al. |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 | 2/2007 | Matthis et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233080 A1 | 10/2007 | Na et al. |
| 2007/0233146 A1 | 10/2007 | Henniges et al. |
| 2007/0233247 A1 | 10/2007 | Schwab |
| 2007/0250166 A1 | 10/2007 | McKay |
| 2007/0270833 A1 | 11/2007 | Bonutti et al. |
| 2007/0270879 A1 | 11/2007 | Isaza et al. |
| 2007/0282443 A1 | 12/2007 | Globerman et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154374 A1 | 6/2008 | Labrom |
| 2008/0161810 A1 | 7/2008 | Melkent |
| 2008/0161927 A1 | 7/2008 | Savage et al. |
| 2008/0183204 A1 | 7/2008 | Greenhalgh et al. |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0294202 A1 | 11/2008 | Peterson et al. |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1 | 3/2009 | Bhatnagar et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevoets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0187247 A1 | 7/2009 | Metcalf, Jr. et al. |
| 2009/0216238 A1 | 8/2009 | Stark |
| 2009/0270928 A1 | 10/2009 | Suddaby |
| 2009/0287254 A1 | 11/2009 | Nayet et al. |
| 2009/0312798 A1 | 12/2009 | Varela |
| 2009/0319043 A1 | 12/2009 | McDevitt et al. |
| 2009/0324678 A1 | 12/2009 | Thorne et al. |
| 2010/0003638 A1 | 1/2010 | Collins et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0094420 A1 | 4/2010 | Grohowski |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |

(56) References Cited

U.S. PATENT DOCUMENTS

| | | |
|---|---|---|
| 2010/0145461 A1 | 6/2010 | Landry et al. |
| 2010/0160977 A1 | 6/2010 | Gephart et al. |
| 2010/0168798 A1 | 7/2010 | Clineffet et al. |
| 2010/0191292 A1 | 7/2010 | DeMeo et al. |
| 2010/0262242 A1 | 10/2010 | Chavatte et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184417 A1 | 7/2011 | Kitch et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0230966 A1 | 9/2011 | Trieu |
| 2011/0238074 A1 | 9/2011 | Ek |
| 2011/0238124 A1 | 9/2011 | Richelsoph |
| 2011/0238181 A1 | 9/2011 | Trieu |
| 2011/0245930 A1 | 10/2011 | Alley et al. |
| 2011/0257755 A1 | 10/2011 | Bellemere et al. |
| 2011/0264229 A1 | 10/2011 | Donner |
| 2011/0276098 A1 | 11/2011 | Biedermann et al. |
| 2011/0295272 A1 | 12/2011 | Assell et al. |
| 2011/0295370 A1 | 12/2011 | Suh et al. |
| 2011/0313471 A1 | 12/2011 | McLean et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0035667 A1 | 2/2012 | Van Nortwick et al. |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1 | 7/2012 | Trieu |
| 2012/0226318 A1 | 9/2012 | Wenger et al. |
| 2012/0253398 A1 | 10/2012 | Metcalf et al. |
| 2012/0259372 A1 | 10/2012 | Glazer et al. |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0072984 A1 | 3/2013 | Robinson |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0274890 A1 | 10/2013 | McKay |
| 2013/0325129 A1 | 12/2013 | Huang |
| 2014/0012334 A1 | 1/2014 | Armstrong et al. |
| 2014/0012340 A1 | 1/2014 | Beck et al. |
| 2014/0031934 A1 | 1/2014 | Trieu |
| 2014/0031935 A1 | 1/2014 | Donner et al. |
| 2014/0031938 A1 | 1/2014 | Lechmann et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0172027 A1 | 6/2014 | Biedermann et al. |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1 | 9/2014 | Mauldin et al. |
| 2014/0276851 A1 | 9/2014 | Schneider et al. |
| 2014/0277139 A1 | 9/2014 | Vrionis et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288649 A1 | 9/2014 | Hunt |
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0012051 A1 | 1/2015 | Warren et al. |
| 2015/0039037 A1 | 2/2015 | Donner et al. |
| 2015/0080951 A1 | 3/2015 | Yeh |
| 2015/0080972 A1 | 3/2015 | Chin et al. |
| 2015/0094765 A1 | 4/2015 | Donner et al. |
| 2015/0112444 A1 | 4/2015 | Aksu |
| 2015/0147397 A1 | 5/2015 | Altschuler |
| 2015/0150683 A1 | 6/2015 | Donner et al. |
| 2015/0173805 A1 | 6/2015 | Donner et al. |
| 2015/0173904 A1 | 6/2015 | Stark |
| 2015/0182268 A1 | 7/2015 | Donner et al. |
| 2015/0190149 A1 | 7/2015 | Assell et al. |
| 2015/0190187 A1 | 7/2015 | Parent et al. |
| 2015/0209094 A1 | 7/2015 | Anderson |
| 2015/0216566 A1 | 8/2015 | Mikhail et al. |
| 2015/0238203 A1 | 8/2015 | Asfora |
| 2015/0250513 A1 | 9/2015 | De Lavigne Sainte |
| 2015/0250611 A1 | 9/2015 | Schifano et al. |
| 2015/0250612 A1 | 9/2015 | Schifano et al. |
| 2015/0257892 A1 | 9/2015 | Lechmann et al. |
| 2015/0313720 A1 | 11/2015 | Lorio |
| 2015/0320450 A1 | 11/2015 | Mootien et al. |
| 2015/0320451 A1 | 11/2015 | Mootien et al. |
| 2015/0320469 A1 | 11/2015 | Biedermann et al. |
| 2015/0342753 A1 | 12/2015 | Donner et al. |
| 2016/0000488 A1 | 1/2016 | Cross, III |
| 2016/0022429 A1 | 1/2016 | Greenhalgh et al. |
| 2016/0095711 A1 | 4/2016 | Castro |
| 2016/0095721 A1 | 4/2016 | Schell et al. |
| 2016/0100870 A1 | 4/2016 | Lavigne et al. |
| 2016/0106477 A1 | 4/2016 | Hynes et al. |
| 2016/0106479 A1 | 4/2016 | Hynes et al. |
| 2016/0120661 A1 | 5/2016 | Schell et al. |
| 2016/0143671 A1 | 5/2016 | Jimenez |

(56) References Cited

U.S. PATENT DOCUMENTS

| | | |
|---|---|---|
| 2016/0157908 A1 | 6/2016 | Cawley et al. |
| 2016/0166301 A1 | 6/2016 | Papangelou et al. |
| 2016/0175113 A1 | 6/2016 | Lins |
| 2016/0184103 A1 | 6/2016 | Fonte et al. |
| 2016/0213487 A1 | 7/2016 | Wilson et al. |
| 2016/0242820 A1 | 8/2016 | Whipple et al. |
| 2016/0242912 A1 | 8/2016 | Lindsey et al. |
| 2016/0249940 A1 | 9/2016 | Stark |
| 2016/0287171 A1 | 10/2016 | Sand et al. |
| 2016/0287301 A1 | 10/2016 | Mehl et al. |
| 2016/0310188 A1 | 10/2016 | Marino et al. |
| 2016/0310197 A1 | 10/2016 | Black et al. |
| 2016/0324643 A1 | 11/2016 | Donner et al. |
| 2016/0324656 A1 | 11/2016 | Morris et al. |
| 2016/0374727 A1 | 12/2016 | Greenhalgh et al. |
| 2017/0014235 A1 | 1/2017 | Jones et al. |
| 2017/0020573 A1 | 1/2017 | Cain et al. |
| 2017/0020585 A1 | 1/2017 | Harshman et al. |
| 2017/0049488 A1 | 2/2017 | Vestgaarden |
| 2017/0086885 A1 | 3/2017 | Duncan et al. |
| 2017/0128083 A1 | 5/2017 | Germain |
| 2017/0128214 A1 | 5/2017 | Mayer |
| 2017/0135733 A1 | 5/2017 | Donner et al. |
| 2017/0135737 A1 | 5/2017 | Krause |
| 2017/0143513 A1 | 5/2017 | Sandstrom et al. |
| 2017/0156879 A1 | 6/2017 | Janowski |
| 2017/0156880 A1 | 6/2017 | Halverson et al. |
| 2017/0202511 A1 | 7/2017 | Chang et al. |
| 2017/0209155 A1 | 7/2017 | Petersen |
| 2017/0216036 A1 | 8/2017 | Cordaro |
| 2017/0224393 A1 | 8/2017 | Lavigne et al. |
| 2017/0246000 A1 | 8/2017 | Pavlov et al. |
| 2017/0258498 A1 | 9/2017 | Redmond et al. |
| 2017/0258506 A1 | 9/2017 | Redmond et al. |
| 2017/0258606 A1 | 9/2017 | Afzal |
| 2017/0266007 A1 | 9/2017 | Gelaude et al. |
| 2017/0296344 A1 | 10/2017 | Souza et al. |
| 2017/0303938 A1 | 10/2017 | Rindal et al. |
| 2017/0333205 A1 | 11/2017 | Joly et al. |
| 2018/0104071 A1 | 4/2018 | Reckling et al. |
| 2018/0177534 A1 | 6/2018 | Mesiwala et al. |
| 2018/0200063 A1 | 7/2018 | Kahmer et al. |
| 2018/0228617 A1 | 8/2018 | Srour et al. |
| 2018/0228621 A1 | 8/2018 | Reiley et al. |
| 2018/0368894 A1 | 12/2018 | Wieland et al. |
| 2019/0090888 A1 | 3/2019 | Sand et al. |
| 2019/0133613 A1 | 5/2019 | Reiley et al. |
| 2019/0133783 A1 | 5/2019 | Unger et al. |
| 2019/0142606 A1 | 5/2019 | Freudenberger |
| 2019/0159818 A1 | 5/2019 | Schneider et al. |
| 2019/0159901 A1 | 5/2019 | Mauldin et al. |
| 2019/0298528 A1 | 10/2019 | Lindsey et al. |
| 2019/0298542 A1 | 10/2019 | Kloss |
| 2019/0343640 A1 | 11/2019 | Donner et al. |
| 2019/0343641 A1 | 11/2019 | Mauldin et al. |
| 2019/0343653 A1 | 11/2019 | McKay |
| 2020/0000595 A1 | 1/2020 | Jones et al. |
| 2020/0008817 A1 | 1/2020 | Reiley et al. |
| 2020/0008850 A1 | 1/2020 | Mauldin et al. |
| 2020/0246158 A1 | 8/2020 | Bergey |
| 2020/0261240 A1 | 8/2020 | Mesiwala et al. |
| 2020/0268525 A1 | 8/2020 | Mesiwala et al. |
| 2022/0031474 A1 | 2/2022 | Reckling et al. |
| 2022/0096098 A1 | 3/2022 | Sand et al. |
| 2022/0280303 A1 | 9/2022 | Mauldin et al. |
| 2022/0409381 A1 | 12/2022 | Ginn |
| 2023/0000526 A1 | 1/2023 | Follini et al. |
| 2023/0000630 A1 | 1/2023 | Ginn et al. |
| 2023/0000631 A1 | 1/2023 | Ginn et al. |
| 2023/0076180 A1 | 3/2023 | Schifano et al. |
| 2023/0095586 A1 | 3/2023 | Mauldin et al. |
| 2023/0210667 A1 | 7/2023 | Lindsey et al. |
| 2023/0263554 A1 | 8/2023 | Stuart et al. |
| 2023/0270559 A1 | 8/2023 | Mesiwala et al. |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| DE | 102011001264 A1 | 9/2012 |
| DE | 102012106336 A1 | 1/2014 |
| EP | 1287796 A1 | 3/2003 |
| EP | 2070481 B1 | 2/2012 |
| EP | 2796104 A1 | 10/2014 |
| EP | 2590576 B1 | 10/2015 |
| EP | 2749238 B1 | 3/2017 |
| EP | 2887899 B1 | 8/2017 |
| EP | 2341852 B1 | 8/2018 |
| EP | 2496162 B1 | 10/2018 |
| EP | 3616634 A1 | 3/2020 |
| EP | 2408389 B1 | 4/2021 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2007535973 A | 12/2007 |
| JP | 2008540036 A | 11/2008 |
| JP | 2009521990 A | 6/2009 |
| JP | 2009533159 A | 9/2009 |
| JP | 2010137016 A | 6/2010 |
| JP | 2015510506 A | 4/2015 |
| WO | WO97/31517 A2 | 8/1997 |
| WO | WO01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2006/074321 A2 | 7/2006 |
| WO | WO2009/025884 A2 | 2/2009 |
| WO | WO2009/029074 A1 | 3/2009 |
| WO | WO2010/105196 A1 | 9/2010 |
| WO | WO2011010463 A1 | 1/2011 |
| WO | WO2011/110865 A2 | 9/2011 |
| WO | WO2011/124874 A1 | 10/2011 |
| WO | WO2011/149557 A1 | 12/2011 |
| WO | WO2012/015976 A1 | 2/2012 |
| WO | WO2013/000071 A1 | 1/2013 |
| WO | WO2013/119907 A1 | 8/2013 |
| WO | WO2017/147537 A1 | 8/2017 |

OTHER PUBLICATIONS

Stuart et al.; U.S. Appl. No. 17/104,753 entitled "Bone stabilizing implants and methods of placement across SI joints," filed Nov. 25, 2020.

Schneider et al.; U.S. Appl. No. 17/443,388 entitled "Matrix implant," filed Jul. 26, 2021.

Mesiwala et al.; U.S. Appl. No. 17/217,794 entitled "Implants for spinal fizxation or fusion," filed Mar. 30, 2021.

Acumed; Acutrak Headless Compressioin Screw (product information); 12 pgs; © 2005; retrieved Sep. 25, 2014 from http://www.rcsed.ac.uk/fellows/lvanrensburg/classification/surgtech/acumed/manuals/acutrak-brochure%200311.pdf.

Al-Khayer et al.; Percutaneous sacroiliac joint arthrodesis, a novel technique; J Spinal Disord Tech; vol. 21; No. 5; pp. 359-363; Jul. 2008.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

(56) References Cited

OTHER PUBLICATIONS

Lu et al.; Mechanical properties of porous materials; Journal of Porous Materials; 6(4); pp. 359-368; Nov. 1, 1999.
Peretz et al.; The internal bony architecture of the sacrum, Spine; 23(9); pp. 971-974; May 1, 1998.
Richards et al.; Bone density and cortical thickness in normal, osteopenic, and osteoporotic sacra; Journal of Osteoporosis; 2010(ID 504078); 5 pgs; Jun. 9, 2010.
Wise et al.; Minimally invasive sacroiliac arthrodesis, outcomes of a new technique; J Spinal Disord Tech; vol. 21; No. 8; pp. 579-584; Dec. 2008.
Reiley; U.S. Appl. No. 16/932,001 entitled "Apparatus, systems, and methods for the fixation or fusion of bone," filed Jul. 17, 2020.
Reiley; U.S. Appl. No. 16/933,084 entitled "Apparatus, systems, and methods for the fixation or fusion of bone," filed Jul. 20, 2020.
Reiley; U.S. Appl. No. 16/933,108 entitled "Apparatus, systems, and methods for the fixation or fusion of bone," filed Jul. 20, 2020.
Mesiwala et al.; U.S. Appl. No. 17/649,265 entitled "Implants for spinal fixation and or fusion," filed Jan. 28, 2022.
Mesiwala et al.; U.S. Appl. No. 17/649,296 entitled "Implants for spinal fixation and or fusion," filed Jan. 28, 2022.
Mauldin et al.; U.S. Appl. No. 17/649,544 entitled "Fenestrated implant," filed Jan. 31, 2022.
Mauldin et al.; U.S. Appl. No. 17/650,473 entitled "Fenestrated implant," filed Feb. 9, 2022.
Reiley et al.; U.S. Appl. No. 18/317,832 entitled "Implants for bone fixation or fusion," filed May 15, 2023.
Mauldin et al.; U.S. Appl. No. 18/311,103 entitled "Systems, device, and methods for joint fusion," filed May 2, 2023.

\* cited by examiner (Anterior)

(Posterior)

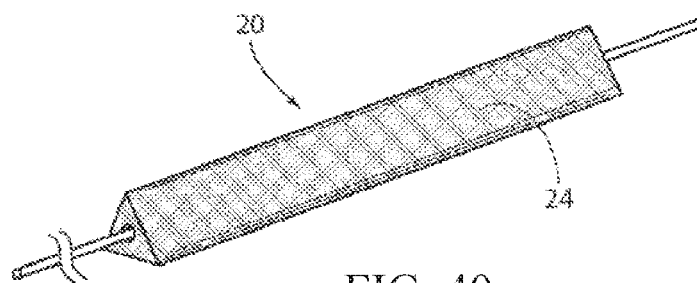
FIG. 40
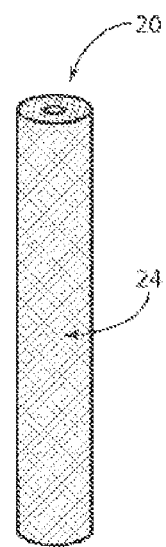 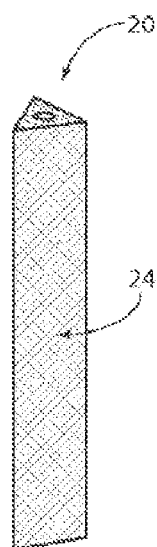 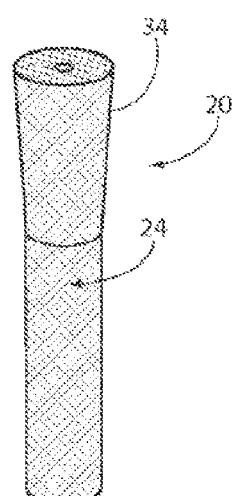
FIG. 41      FIG. 42      FIG. 43
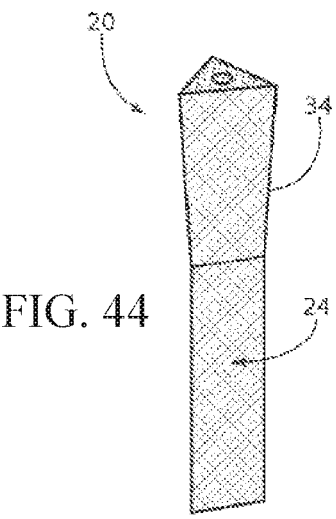
FIG. 44

Translaminar Lumbar Fusion (Posterior Approach)

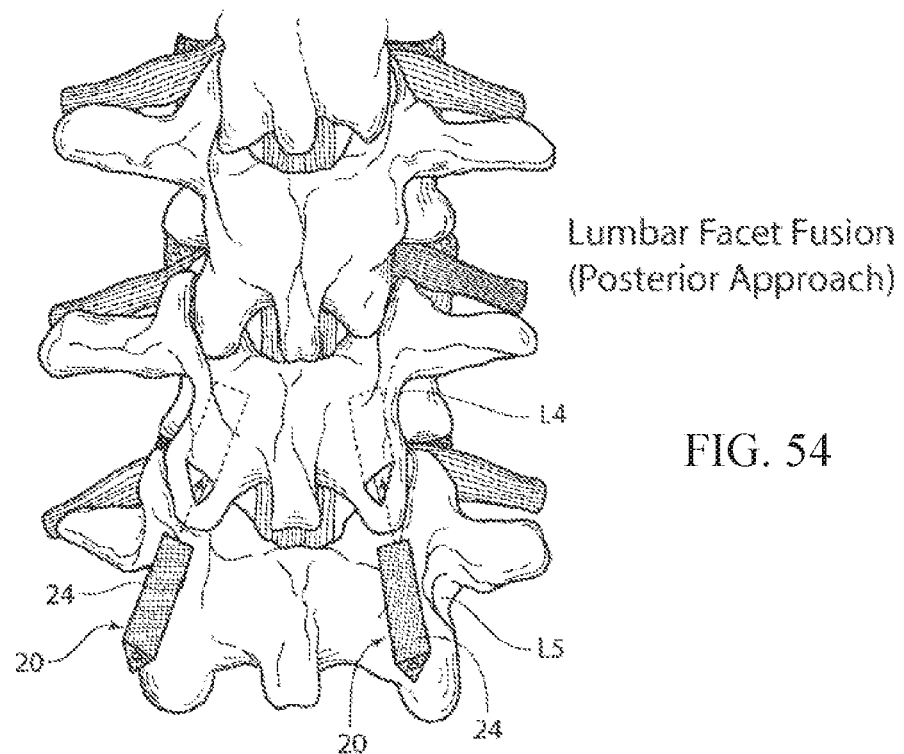
Lumbar Facet Fusion (Posterior Approach)
FIG. 54
FIG. 55
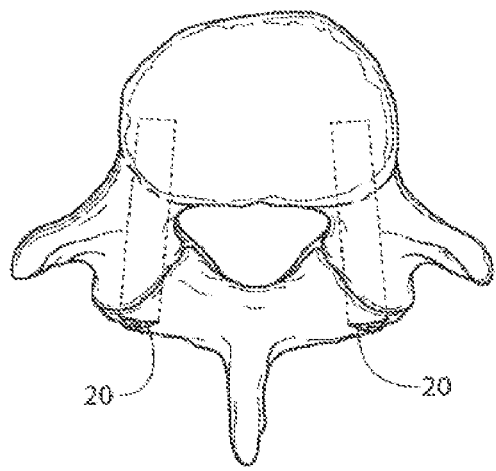
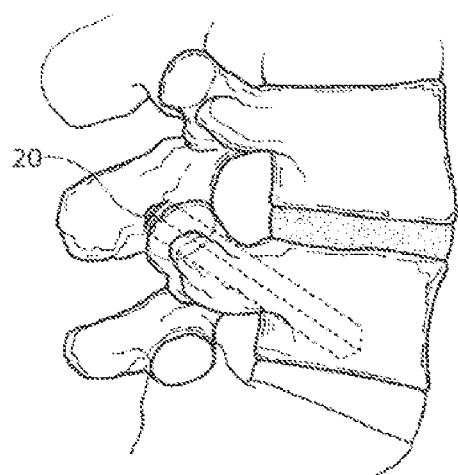
FIG. 56

APPARATUS, SYSTEMS, AND METHODS FOR THE FIXATION OR FUSION OF BONE

CROSS REFERENCE TO RELATED APPLICATIONS

This application is a continuation of U.S. patent application Ser. No. 15/952,102, filed Apr. 12, 2018, which is a continuation of U.S. patent application Ser. No. 15/195,955, filed Jun. 28, 2016, titled "APPARATUS, SYSTEMS, AND METHODS FOR THE FIXATION OR FUSION OF BONE", now U.S. Pat. No. 9,949,843, which is a continuation-in-part of U.S. patent application Ser. No. 13/858,814, filed Apr. 8, 2013, titled "APPARATUS, SYSTEMS, AND METHODS FOR ACHIEVING TRANS-ILIAC LUMBAR FUSION," now U.S. Pat. No. 9,375,323, which is a continuation of U.S. patent application Ser. No. 12/960,831, filed Dec. 6, 2010, titled "APPARATUS, SYSTEMS, AND METHODS FOR ACHIEVING TRANS-ILIAC LUMBAR FUSION," now U.S. Pat. No. 8,414,648, which is a continuation-in-part of U.S. patent application Ser. No. 11/136,141, filed May 24, 2005, titled "SYSTEMS AND METHODS FOR THE FIXATION OR FUSION OF BONE," now U.S. Pat. No. 7,922,765.

U.S. patent application Ser. No. 15/952,102, filed Apr. 12, 2018, is a continuation of U.S. patent application Ser. No. 15/195,955, filed Jun. 28, 2016, titled "APPARATUS, SYSTEMS, AND METHODS FOR THE FIXATION OR FUSION OF BONE", now U.S. Pat. No. 9,949,843, which is also a continuation-in-part of U.S. patent application Ser. No. 14/274,486, filed May 9, 2014, now U.S. Pat. No. 9,486,264, which is a continuation of U.S. patent application Ser. No. 13/786,037, filed Mar. 5, 2013, titled "SYSTEMS AND METHODS FOR THE FIXATION OR FUSION OF BONE USING COMPRESSIVE IMPLANTS," now U.S. Pat. No. 8,734,462, which is a continuation of U.S. patent application Ser. No. 12/924,784, filed Oct. 5, 2010, titled "SYSTEMS AND METHODS FOR THE FIXATION OR FUSION OF BONE USING COMPRESSIVE IMPLANTS," now U.S. Pat. No. 8,388,667, which is a continuation-in-part of U.S. patent application Ser. No. 11/136,141, filed May 24, 2005, titled "SYSTEMS AND METHODS FOR THE FIXATION OR FUSION OF BONE," now U.S. Pat. No. 7,922,765 B2, each of which are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This application relates generally to the fixation or fusion of bone.

BACKGROUND

Many types of hardware are available both for the fixation of bones that are fractured and for the fixation of bones that are to fused (arthrodesed).

For example, the human hip girdle (see FIGS. 9 and 10) is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain.

To relieve pain generated from the SI Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screw and screw with plates are used for sacro-iliac fusion. At the same time the cartilage has to be removed from the "synovial joint" portion of the SI joint. This requires a large incision to approach the damaged, subluxed, dislocated, fractured, or degenerative joint.

The spine (see FIG. 37) is a complex interconnecting network of nerves, joints, muscles, tendons and ligaments, and all are capable of producing pain.

The spine is made up of small bones, called vertebrae. The vertebrae protect and support the spinal cord. They also bear the majority of the weight put upon the spine.

Between each vertebra is a soft, gel-like "cushion," called an intervertebral disc. These flat, round cushions act like shock absorbers by helping absorb pressure and keep the bones from rubbing against each other. The intervertebral disc also binds adjacent vertebrae together. The intervertebral discs are a type of joint in the spine. Intervertebral disc joints can bend and rotate a bit but do not slide as do most body joints.

Each vertebra has two other sets of joints, called facet joints (see FIG. 38). The facet joints are located at the back of the spine (posterior). There is one facet joint on each lateral side (right and left). One pair of facet joints faces upward (called the superior articular facet) and the other pair of facet joints faces downward (called the inferior articular facet). The inferior and superior facet joints mate, allowing motion (articulation), and link vertebrae together. Facet joints are positioned at each level to provide the needed limits to motion, especially to rotation and to prevent forward slipping (spondylolisthesis) of that vertebra over the one below.

In this way, the spine accommodates the rhythmic motions required by humans to walk, run, swim, and perform other regular movements. The intervertebral discs and facet joints stabilize the segments of the spine while preserving the flexibility needed to turn, look around, and get around.

Degenerative changes in the spine can adversely affect the ability of each spinal segment to bear weight, accommodate movement, and provide support. When one segment deteriorates to the point of instability, it can lead to localized pain and difficulties. Segmental instability allows too much movement between two vertebrae. The excess movement of the vertebrae can cause pinching or irritation of nerve roots. It can also cause too much pressure on the facet joints, leading to inflammation. It can cause muscle spasms as the paraspinal muscles try to stop the spinal segment from moving too much. The instability eventually results in faster degeneration in this area of the spine.

Degenerative changes in the spine can also lead to spondylolysis and spondylolisthesis. Spondylolisthesis is the term used to describe when one vertebra slips forward on the one below it. This usually occurs because there is a spondylolysis (defect) in the vertebra on top. For example, a fracture or a degenerative defect in the interarticular parts of lumbar vertebra L1 may cause a forward displacement of the lumbar vertebra L5 relative to the sacral vertebra S1 (called L5-S1 spondylolisthesis). When a spondylolisthesis occurs, the facet joint can no longer hold the vertebra back. The intervertebral disc may slowly stretch under the increased stress and allow other upper vertebra to slide forward.

An untreated persistent, episodic, severely disabling back pain problem can easily ruin the active life of a patient. In many instances, pain medication, splints, or other normally-indicated treatments can be used to relieve intractable pain in a joint. However, in for severe and persistent problems that cannot be managed by these treatment options, degenerative changes in the spine may require a bone fusion surgery to stop both the associated disc and facet joint problems.

A fusion is an operation where two bones, usually separated by a joint, are allowed to grow together into one bone. The medical term for this type of fusion procedure is arthrodesis.

Lumbar fusion procedures have been used in the treatment of pain and the effects of degenerative changes in the lower back. A lumbar fusion is a fusion in the S1-L5-L4 region in the spine.

One conventional way of achieving a lumbar fusion is a procedure called anterior lumbar interbody fusion (ALIF). In this procedure, the surgeon works on the spine from the front (anterior) and removes a spinal disc in the lower (lumbar) spine. The surgeon inserts a bone graft into the space between the two vertebrae where the disc was removed (the interbody space). The goal of the procedure is to stimulate the vertebrae to grow together into one solid bone (known as fusion). Fusion creates a rigid and immovable column of bone in the problem section of the spine. This type of procedure is used to try and reduce back pain and other symptoms.

Facet joint fixation procedures have also been used for the treatment of pain and the effects of degenerative changes in the lower back. These procedures take into account that the facet joint is the only true articulation in the lumbosacral spine. In one conventional procedure for achieving facet joint fixation, the surgeon works on the spine from the back (posterior). The surgeon passes screws from the spinous process through the lamina and across the mid-point of one or more facet joints.

Conventional treatment of spondylolisthesis may include a laminectomy to provide decompression and create more room for the exiting nerve roots. This can be combined with fusion using, e.g., an autologous fibular graft, which may be performed either with or without fixation screws to hold the bone together. In some cases the vertebrae are moved back to the normal position prior to performing the fusion, and in others the vertebrae are fused where they are after the slip, due to the increased risk of injury to the nerve with moving the vertebra back to the normal position.

Currently, these procedures entail invasive open surgical techniques (anterior and/or posterior). Further, ALIF entails the surgical removal of the disc. Like all invasive open surgical procedures, such operations on the spine risk infections and require hospitalization. Invasive open surgical techniques involving the spine continue to be a challenging and difficult area.

SUMMARY OF THE DISCLOSURE

Embodiments of the invention provide bone fixation/fusion systems, devices, and related methods for stabilizing adjacent bone segments in a minimally invasive manner. The adjacent bone segments can comprise parts of the same bone that have been fractured, or two or more individual bones separated by a space or joint. As used herein, "bone segments" or "adjacent bone regions" refer to either situation, i.e., a fracture line in a single bone (which the devices serve to fixate), or a space or joint between different bone segments (which the devices serve to arthrodese or fuse). The devices can therefore serve to perform a fixation function between two or more individual bones, or a fusion function between two or more parts of the same bone, or both functions.

One aspect of the invention provides assemblies and associated methods for the fixation or fusion of bone structures comprising first and second bone segments separated by a fracture line or joint. The assemblies and associated methods comprise an anchor body sized and configured to be introduced into the first and second bone segments. The anchor body has a distal end located in an interior region of the second bone segment; a proximal end located outside an exterior region of the first bone segment; and an intermediate region spanning the fracture line or joint between the first and second bone segments. The assemblies and associated methods also include a distal anchor secured to the interior region of the second bone segment and affixed to the distal end of the anchor body to anchor the distal end in the second bone segment. The assemblies and associated methods further include a proximal anchor secured to the exterior region of the first bone segment and affixed to the proximal end of the anchor body, which, in concert with the distal anchor, places the anchor body in compression to compress and fixate the bone segments relative to the fracture line or joint. The assemblies and associated methods also include an elongated implant structure carried by the intermediate region of the anchor body and spanning the fracture line or joint between the bone segments. The elongated implant structure includes an exterior surface region treated to provide bony in-growth or through-growth along the implant structure, to accelerate the fixation or fusion of the first and second bone segments held in compression and fixated by the anchor body.

The bone fixation/fusion systems, devices, and related methods are well suited for stabilizing adjacent bone segments in the SI-Joint.

Accordingly, another aspect of the invention provides a method for the fusion of the sacral-iliac joint between an iliac and a sacrum. The method comprises creating an insertion path through the ilium, through the sacral-iliac joint, and into the sacrum. The method includes providing an anchor body sized and configured to be introduced through the insertion path laterally into the ilium and sacrum. The anchor body has a distal end sized and configured to be located in an interior region of the sacrum; a proximal end sized and configured to be located outside an exterior region of the iliac; and an intermediate region sized and configured to span the sacral-iliac joint. The method includes providing an elongated implant structure sized and configured to be passed over the anchor body to span the sacral-iliac joint between the iliac and sacrum. The elongated implant structure includes an exterior surface region treated to provide bony in-growth or through-growth along the implant structure. The method includes introducing the anchor body through the insertion path from the ilium, through the sacral-iliac joint, and into the sacrum. The method includes anchoring the distal end of the anchor body in the interior region of the sacrum. The method includes passing the elongated implant structure over the anchor body to span the sacral-iliac joint between the ilium and sacrum, and anchoring the proximal end of the anchor body to an exterior region of the ilium, which, in concert with the anchored distal end, places the anchor body in compression to compress and fixate the sacral-iliac joint. The bony in-growth or through-growth region of the implant structure accelerates the fixation or fusion of the sacral-iliac joint held in compression and fixated by the anchor body.

Embodiments of the invention provide apparatus, systems, and methods for the fusion and/or stabilization of the lumbar spine. The apparatus, systems, and methods include one or more elongated, stem-like implant structures sized and configured for the fusion or stabilization of adjacent bone structures in the lumbar region of the spine, either across the intervertebral disc or across one or more facet joints. Each implant structure includes a region formed along at least a portion of its length to promote bony in-growth onto or into surface of the structure and/or bony growth entirely through all or a portion of the structure. The bony in-growth or through-growth region along the surface of the implant structure accelerates bony in-growth or through-growth onto, into, or through the implant structure 20. The implant structure therefore provides extra-articular/intra osseous fixation, when bone grows in and around the bony in-growth or through-growth region. Bony in-growth or through-growth onto, into, or through the implant structure helps speed up the fusion and/or stabilization process of the adjacent bone regions fixated by the implant structure.

The assemblies of one or more implant structures make possible the achievement of diverse interventions involving the fusion and/or stabilization of lumbar and sacral vertebra in a non-invasive manner, with minimal incision, and without the necessitating the removing the intervertebral disc. The representative lumbar spine interventions, which can be performed on adults or children, include, but are not limited to, lumbar interbody fusion; translaminar lumbar fusion; lumbar facet fusion; trans-iliac lumbar fusion; and the stabilization of a spondylolisthesis.

BRIEF DESCRIPTION OF THE DRAWINGS

FIGS. 11 to 13A and 13B are anatomic views showing, respectively, in exploded perspective, assembled perspective, assembled anterior view, and assembled axial section view, the implantation of three implant structures, without association of a compression stem assembly, for the fixation of the SI-Joint using a lateral approach laterally through the ilium, the SI-Joint, and into the sacrum S1.

FIGS. 14 to 16A and 16B are anatomic views showing, respectively, in exploded perspective, assembled perspective, assembled anterior view, and assembled axial section view, the implantation of three implant structures, in association with a compression stem assembly, for the fixation of the SI-Joint using a lateral approach laterally through the ilium, the SI-Joint, and into the sacrum S1.

FIGS. 17 to 19A and 19B are anatomic views showing, respectively, in exploded perspective, assembled perspective, assembled lateral view, and assembled axial section view, the implantation of three implant structures, without association of a compression stem assembly, for the fixation of the SI-Joint using a postero-lateral approach entering from the posterior iliac spine of the ilium, angling through the SI-Joint, and terminating in the sacral alae.

FIGS. 20 to 22A and 22B are anatomic views showing, respectively, in exploded perspective, assembled perspective, assembled lateral view, and assembled axial section view, the implantation of three implant structures, in association with a compression stem assembly, for the fixation of the SI-Joint using a postero-lateral approach entering from the posterior iliac spine of the ilium, angling through the SI-Joint, and terminating in the sacral alae.

FIG. 40 is a perspective view of a representative embodiment of an elongated, stem-like, cannulated implant structure well suited for the fusion or stabilization of adjacent bone structures in the lumbar region of the spine, either across the intervertebral disc or across one or more facet joints.

FIGS. 41 to 44 are perspective views of other representative embodiments of implant structures well suited for the fusion or stabilization of adjacent bone structures in the lumbar region of the spine, either across the intervertebral disc or across one or more facet joints.

FIG. 54 is an anatomic posterior perspective view, exploded prior to implantation, of a representative configuration of an assembly of one or more implant structures like that shown in FIG. 40, sized and configured to achieve lumbar facet fusion, in a non-invasive manner and without removal of the intervertebral disc.

FIG. 55 is an anatomic inferior transverse plane view showing the assembly shown in FIG. 54 after implantation.

FIG. 56 is an anatomic lateral view showing the assembly shown in FIG. 54 after implantation.

DETAILED DESCRIPTION

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

Part I

The following describes embodiments of the invention for use in the fixation or fusion of the SI-joint and other bone segments or joints.

I. The Compression Stem Assembly

Figure 1:
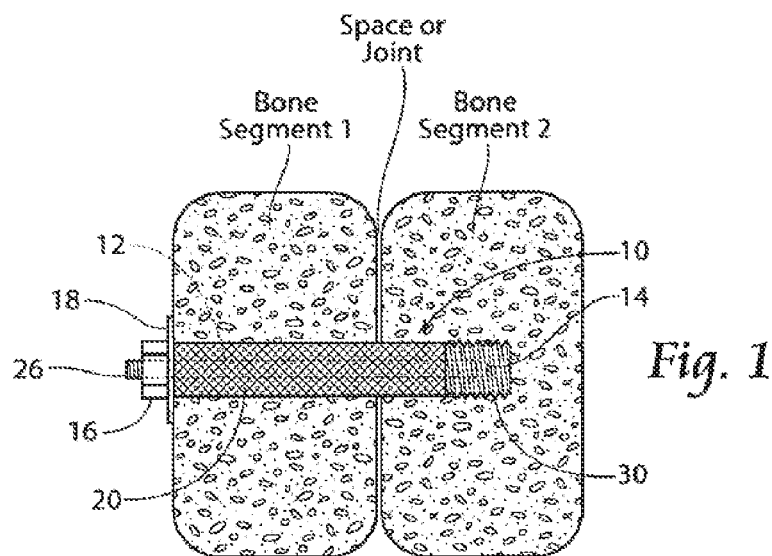
FIG. 1 is a side section view of a compression stem assembly assembled in adjacent bone regions, which are shown in FIG. 1 in a diagrammatically fashion for the purpose of illustration, without anatomic detail, which is later shown, e.g., in FIG. 16.
Figure 2:
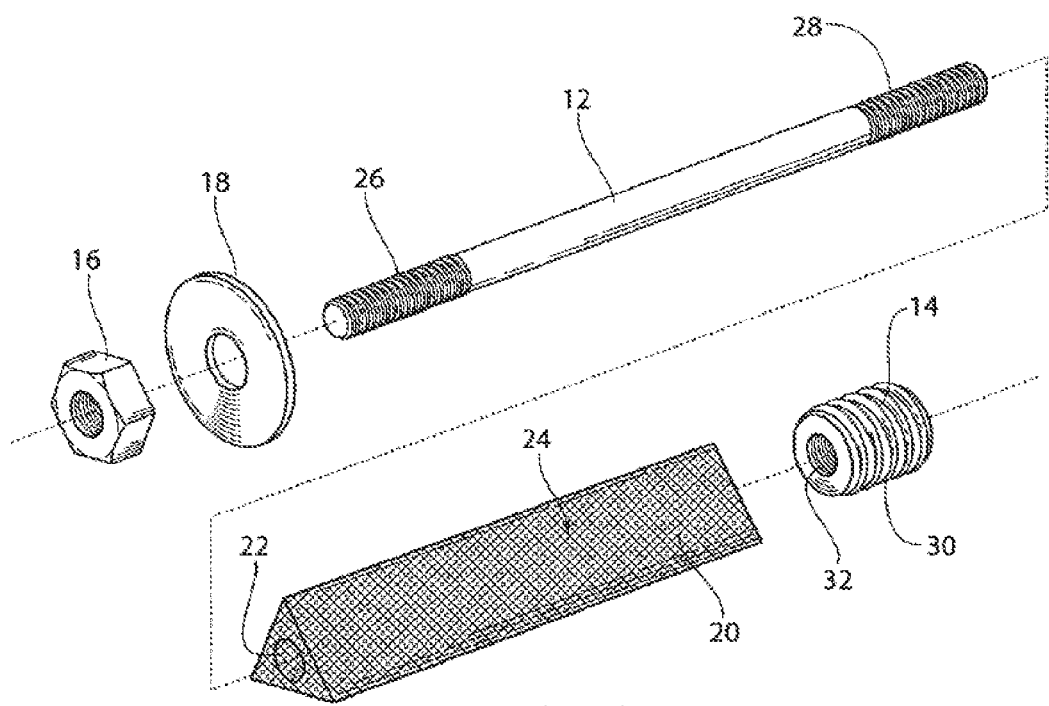
FIG. 2 is an exploded perspective view of the components of the compression stem assembly shown in FIG. 1 prior to assembly.

FIGS. 1 and 2 show in assembled and exploded views, respectively, a representative configuration of a compression stem assembly 10 sized and configured for the fixation of bone fractures (i.e., fixation of parts of the same bone) or for the fixation of bones which are to be fused (arthrodesed) (i.e. fixation of two or more individual bones that are adjacent and/or jointed). For the sake of shorthand, the assembly 10 will sometimes be called a bone fixation/fusion compression assembly, to indicate that it can perform a fixation function between two or more individual bones), or a fusion function between two or more parts of the same bone, or both functions. As used herein, "bone segments" or "adjacent bone regions" refer to either situation, i.e., a fracture line in a single bone or a space or joint between different bone segments. In FIG. 1, the bone segment or adjacent bone regions are shown diagrammatically without anatomic detail for the purpose of illustration. Later, e.g., in FIGS. 13 to 16 and FIGS. 20 to 22, the bone segments or adjacent bone regions are shown in a specific anatomic setting, comprising the joint between the sacrum and the ilium of the pelvis, also anatomically called the sacroiliac joint (SI-Joint).

As shown in FIGS. 1 and 2, the compression stem assembly 10 comprises an anchor body 12, which (as shown in FIG. 1) is sized and configured to be placed in compression within bone segments or adjacent bone regions. In a representative embodiment, the anchor body 12 takes the form of a cylindrical anchor pin or rod. Still, the anchor body 12 can possess other geometries.

The anchor body 12 is anchored at a distal end to a distal anchor screw 14 coupled to an interior bone region in one side of the space or joint. The anchor body 12 is secured at a proximal end, on the opposite side of the space or joint, to an exterior bone region by an anchor nut 16 and anchor washer 18. The distal anchor screw 14 and anchor nut 16 hold the anchor body 12 in compression and, in doing so, the anchor body 12 compresses and fixates the bone segments or adjacent bone regions.

The anchor body 12 carries within the bone regions or segments an elongated, stem-like, cannulated implant structure 20. The implant structure 20 includes an interior bore 22 that accommodates its placement by sliding over the anchor body 12. As FIG. 2 shows, the implant structure 20 includes a region 24 formed along at least a portion of its length to promote bony in-growth onto or into surface of the structure and/or bony growth entirely through all or a portion of the structure. The bony-in-growth or through-growth region 24 along the surface of the implant structure 20 accelerates bony in-growth or through-growth onto, into, or through the implant structure 20. Bony in-growth or through-growth onto, into, or through the implant structure 20 helps speed up the fusion process or fracture healing time of the bone segments or adjacent bone regions held in compression and fixated by the anchor body 12.

A. The Anchor Body, Nut, and Washer

The anchor body 12, nut 16, and washer 18 can be formed—e.g., by machining, molding, or extrusion—from a material usable in the prosthetic arts that is capable of being placed into and holding compressive forces and that is not subject to significant bio-absorption or resorption by surrounding bone or tissue over time. The anchor body 12, nut 16, and washer 18 are intended to remain in place for a time sufficient to stabilize the fracture or fusion site. Examples of such materials include, but are not limited to, titanium, titanium alloys, tantalum, chrome cobalt, surgical steel, or any other total joint replacement metal and/or ceramic, sintered glass, artificial bone, any uncemented metal or ceramic surface, or a combination thereof.

In length (see FIG. 1), the anchor body 12 is sized to span a distance through one adjacent bone segment or region, through the intervening space or joint, and at least partially into the other adjacent bone segment or region. The anchor body 12 is sized on length and diameter according to the local anatomy. The morphology of the local structures can be generally understood by medical professionals using textbooks of human skeletal anatomy along with their knowledge of the site and its disease or injury. The physician is also able to ascertain the dimensions of the anchor body 12 based upon prior analysis of the morphology of the targeted bone region using, for example, plain film x-ray, fluoroscopic x-ray, or MRI or CT scanning. A representative diameter for the anchor body 12 can range between 3.2 mm to 3.5 mm.

As best shown in FIG. 2, at least the proximal and distal regions of the anchor body 12 include external helical ridges or screw threads 26 and 28 formed around the cylindrical body of the anchor body 12. Alternatively, the anchor body 12, if desired, can be threaded substantially along its entire length. Desirably, the direction of the screw threads 26 and 28 is the same at both proximal and distal regions of the anchor body 12, e.g., they desirably comprise right-hand threads.

The proximal region of the anchor body 12 carrying the threads 26 is sized to extend, in use, a distance outside the one adjacent bone segment or region. In this way, the proximal region is, in use, exposed so that the proximal anchor nut 16 and washer 18 can be attached. The anchor nut 16 includes complementary internal screw threads that are sized and configured to mate with the external screw threads 26 on the proximal region of the anchor body 12. Representative diameters for an anchor nut 16 and anchor washer 18 for a 3.2 mm anchor body 12 are, respectively, 3.2 mm and 8 mm.

The distal region of the anchor body 12 carrying the threads 28 is sized to extend at least partially into the other adjacent bone segment or region, where it is to be coupled to the anchor screw 14, as will next be described.

B. The Anchor Screw

Like the anchor body 12, nut and washer 18, the anchor screw 14 can likewise be formed—e.g., by machining, or molding—from a durable material usable in the prosthetic arts that is capable of being screwed into bone and that is not subject to significant bio-absorption or resorption by surrounding bone or tissue over time. The anchor screw 14, like the other components of the compression assembly 10, is intended to remain in place for a time sufficient to stabilize the fracture or fusion site. Examples of such materials include, but are not limited to, titanium, titanium alloys, tantalum, chrome cobalt, surgical steel, or any other total joint replacement metal and/or ceramic, or a combination thereof.

The anchor screw 14 is sized to span a distance within the other adjacent bone segment or region at the terminus of the threaded distal region 28 of the anchor body 12. As best shown in FIG. 2, the anchor screw 14 includes external helical ridges or screw threads 30 formed around the cylindrical body of the anchor screw 14. The external screw threads 30 are sized and configured to gain purchase in bone when rotated, so that the anchor screw 14 can be advanced and seated by rotation into bone in the bone segment or region. The anchor screw 14, seated within the bone, resists axial migration and separation. A representative range of lengths for the anchor screw 14 can be between 5 mm to 20 mm, again depending upon the demands of the local anatomy. A representative diameter for the anchor screw 14 is about 7 mm.

The anchor screw 14 also includes internal helical ridges or screw threads 32 formed within a bore in the anchor screw 14. The internal screw threads 32 are sized and configured to mate with the complementary external screw threads 28 on the distal region of the anchor body 12. When threaded and mated to the internal screw threads 32 of the anchor screw 14, the anchor screw 14 anchors the distal region of the anchor body 12 to bone to resists axial migration of the anchor body 12. As before described, the anchor screw 14 (on the distal end) and the anchor nut 16 and anchor washer 18 (on the proximal end) hold the anchor body 12 in compression, thereby compressing and fixating the bone segments or adjacent bone regions.

Alternatively, in place of the anchor screw 14, an internally threaded component free external screw threads can be is sized and configured to be securely affixed within the broached bore in the most distal bone segment where the broached bore terminates, e.g., by making an interference fit and/or otherwise being secured by the use of adhesives. Like the anchor screw 14, the interference fit and/or adhesives anchor the overall implant structure. Adhesives may also be used in combination with the anchor screw 14.

C. The Implant Structure

The implant structure 20 can be formed—e.g., by machining, molding, or extrusion—from a durable material usable in the prosthetic arts that is not subject to significant bioabsorption or resorption by surrounding bone or tissue over time. The implant structure 20, like the other components of the compression assembly 10, is intended to remain in place for a time sufficient to stabilize the fracture or fusion site. Such materials include, but are not limited to, titanium, titanium alloys, tantalum, tivanium (aluminum, vanadium, and titanium), chrome cobalt, surgical steel, or any other total joint replacement metal and/or ceramic, sintered glass, artificial bone, any uncemented metal or ceramic surface, or a combination thereof. Alternatively, the implant structure 20 may be formed from a suitable durable biologic material or a combination of metal and biologic material, such as a biocompatible bone-filling material. The implant structure 20 may be molded from a flowable biologic material, e.g., acrylic bone cement, that is cured, e.g., by UV light, to a non-flowable or solid material.

The implant structure 20 is sized according to the local anatomy. The morphology of the local structures can be generally understood by medical professionals using textbooks of human skeletal anatomy along with their knowledge of the site and its disease or injury. The physician is also able to ascertain the dimensions of the implant structure 20 based upon prior analysis of the morphology of the targeted bone region using, for example, plain film x-ray, fluoroscopic x-ray, or MRI or CT scanning.

Figure 3:
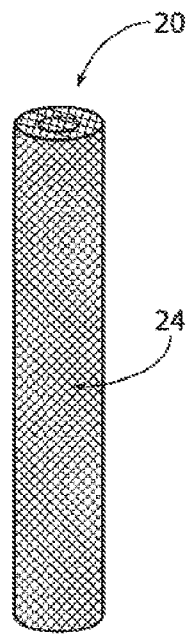
FIGS. 3 to 7 are alternative embodiments of an implant structure which forms a part of the compression stem assembly shown in FIGS. 1 and 2, illustrating different cross-sectional geometries and configurations for the implant structure 20.
Figure 4:
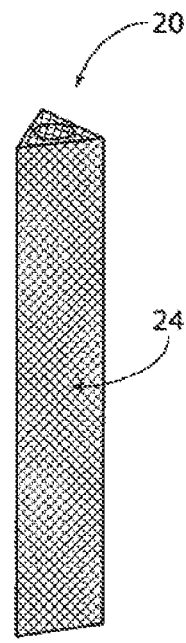

As FIGS. 3 to 7 show, the implant structure 20 can take various shapes and have various cross-sectional geometries. The implant structure 20 can have, e.g., a generally curvilinear (i.e., round or oval) cross-section—as FIG. 3 shows for purposes of illustration—or a generally rectilinear cross section (i.e., square or rectangular or triangular—as FIG. 4 shows for purposes of illustration—or combinations thereof. In FIG. 2, the implant structure 20 is shown to be triangular in cross section, which effectively resists rotation and micromotion once implanted.

Figure 5:
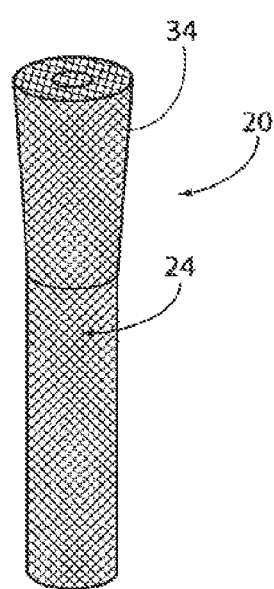
Figure 6:
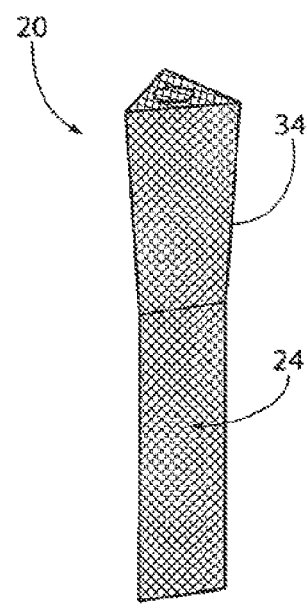
Figure 7:
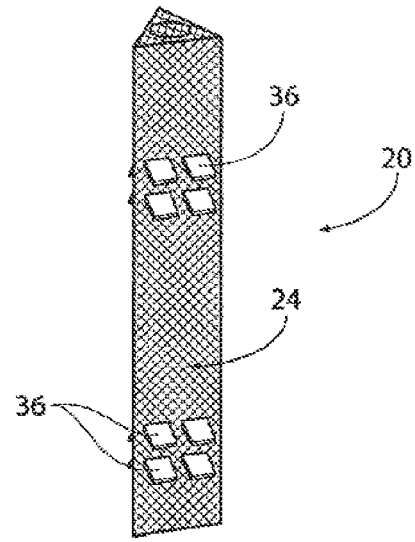

As FIGS. 5 and 6 show, the implant structure 20, whether curvilinear (FIG. 5) or rectilinear (FIG. 6) can include a tapered region 34 at least along a portion of its axial length, meaning that the width or diameter of the implant structure 20 incrementally increases along its axial length. Desirably, the tapered region 34 corresponds with, in use, the proximal region of the implant structure 20 (i.e., the last part of the implant structure 20 to enter bone). The amount of the incremental increase in width or diameter can vary. As an example, for an implant structure 20 having a normal diameter of 7 mm, the magnitude of the incremental increase at its maximum can range between about 0.25 mm to 1.25 mm. The tapered region 34 further enhances the creation and maintenance of compression between the bone segments or regions.

To further enhance the creation and maintenance of compression between the bone segments or regions (see FIG. 7), the implant structure 20, whether curvilinear or rectilinear or tapered, can include projecting bone-gripping surfaces 36 in the form of "teeth" or wings or the like. The teeth or wings 36 can project, e.g., 2 to 4 mm from the surface of the implant structure 20 and face in the direction of the compression forces at proximal and distal ends of the implant structure 20, taking purchase into the bone segments as they are compressed together by the compression assembly.

The bony in-growth or through-growth region 24 may extend along the entire outer surface of the implant structure 20, as shown in FIG. 1 or 2, or the bony in-growth or through-growth region 24 may cover just a specified distance on either side of the bone segments or fracture line. The bony in-growth region 24 or through-growth can comprise, e.g., through holes, and/or various surface patterns, and/or various surface textures, and/or pores, or combinations thereof. The configuration of the bony in-growth or through-growth region 24 can, of course, vary. By way of examples, the bony in-growth or through-growth region 24 can comprise an open mesh configuration; or beaded configuration; or a trabecular configuration; or include holes or fenestrations. Any configuration conducive to bony in-growth and/or bony through-growth will suffice.

The bony in-growth or through-growth region 24 can be coated or wrapped or surfaced treated to provide the bony in-growth or through-growth region, or it can be formed from a material that itself inherently possesses a structure conducive to bony in-growth or through-growth, such as a porous mesh, hydroxyapetite, or other porous surface. The bony in-growth or through-growth region can include holes that allow bone to grow throughout the region.

In a preferred embodiment, the bony in-growth region or through-growth region 24 comprises a porous plasma spray coating on the implant structure 20. This creates a biomechanically rigorous fixation/fusion system, designed to support reliable fixation/fusion and acute weight bearing capacity.

The bony in-growth or through-growth region 24 may further be covered with various other coatings such as antimicrobial, antithrombotic, and osteoinductive agents, or a combination thereof. The entire implant structure 20 may be impregnated with such agents, if desired.

D. Implantation of the Compression Stem Assembly

FIGS. 8A to 8L diagrammatically, show for purposes of illustration, a representative procedure for implanting a compression stem assembly 10. More detailed, anatomically-focused descriptions of particular implantation techniques of the compression stem assembly 10 in the SI-Joint will be described later.

Figure 8A:
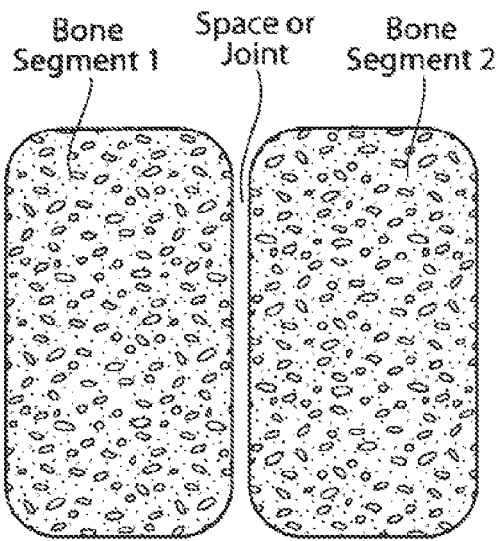
FIGS. 8A to 8L are side section views of the introduction and assembly of the compression stem assembly shown in FIGS. 1 and 2, which is shown in FIGS. 8A to 8L in a diagrammatically fashion for the purpose of illustration, without anatomic detail, as later shown, e.g., in FIG. 16.
Figure 8B:
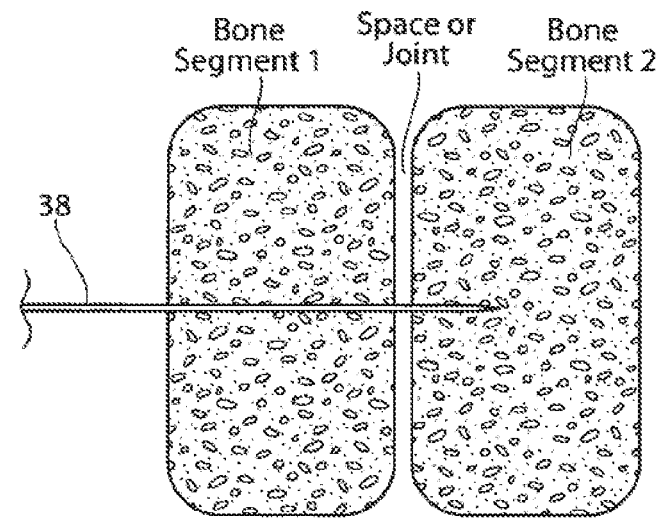

The physician identifies the bone segments or adjacent bone regions that are to be fixated or fused (arthrodesed) (see FIG. 8A). Aided by conventional visualization techniques, e.g., using X-ray image intensifiers such as a C-arms or fluoroscopes to produce a live image feed which is displayed on a TV screen, a guide pin 38 is introduced by conventional means (see FIG. 8B) through the one adjacent bone segment or region, through the intervening space or joint, and partially into the other adjacent bone segment or region.

A cannulated drill bit 40 is passed over the guide pin 38 (see FIG. 8C), to form a pilot insertion path or bore 42 through the one adjacent bone segment or region, through the intervening space or joint, and partially into the other adjacent bone segment or region. A single drill bit or multiple drill bits 40 can be employed to drill through bone fragments or bone surfaces to create a pilot bore 42 of the desired size and configuration. A region of bone distal to the pilot bore 42 is left undrilled and native for seating of the anchor screw 14. When the pilot bore 42 is completed, the cannulated drill bit 40 is removed.

A broach 44 having the external geometry and dimensions matching the external geometry and dimensions of the implant structure 20 (which, in the illustrated embodiment, is triangular) (see FIG. 8D) is tapped over the guide pin 38 through the pilot bore 42. The shaped broach 44 cuts along the edges of the pilot bore 42 to form the desired profile (which, in the illustrated embodiment, is triangular) to accommodate the implant structure 20 through the one adjacent bone segment or region, through the intervening space or joint, and partially into the other adjacent bone segment or region.

The broach 44 is withdrawn (see FIG. 8E), and the anchor screw 14 (its internal screw threads 32 mated to the distal end of a cannulated threaded screw driver 46) is passed over the guide pin 38 to the terminus of the broached bore 48 in the distal bone segment. The anchor screw 14 is threaded by operation of the screw driver 46 (see FIG. 8F) into the undrilled and native bone beyond the terminus of the broached bore 48. For example, the anchor screw 14 can be advanced and buried in bone at least 5 mm beyond the terminus of the broached bore 48.

Figure 8C:
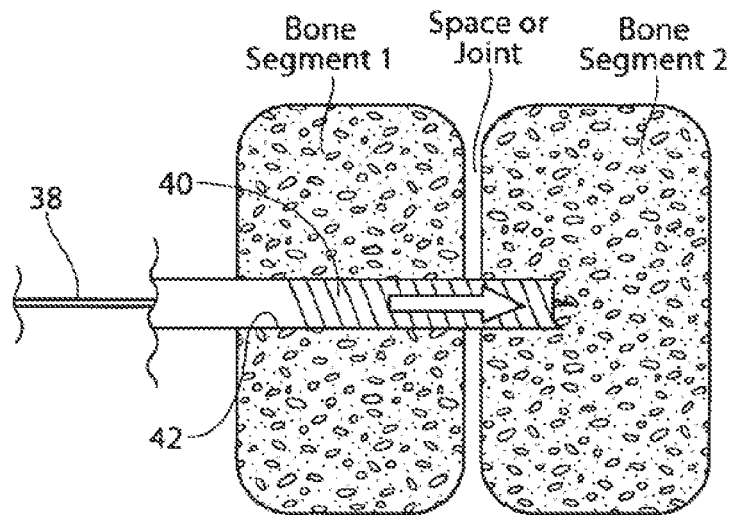
Figure 8D:
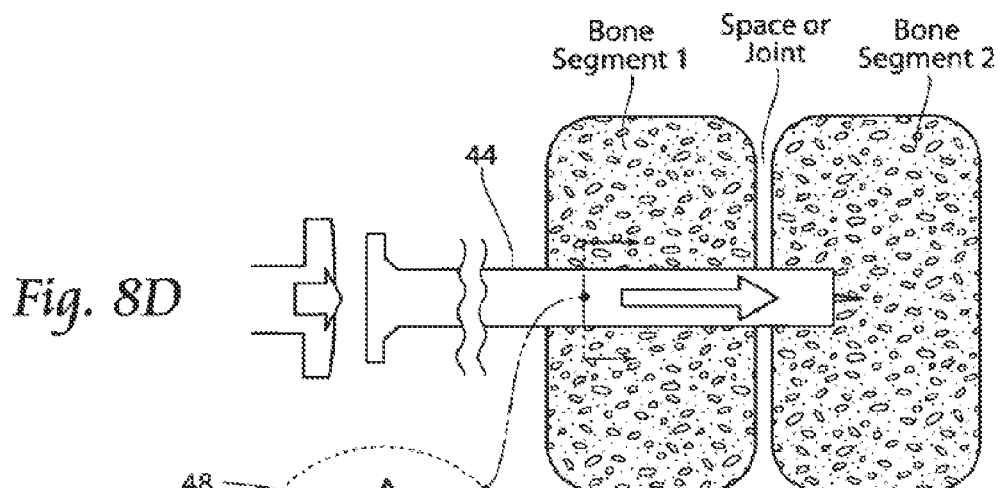
Figure 8E:
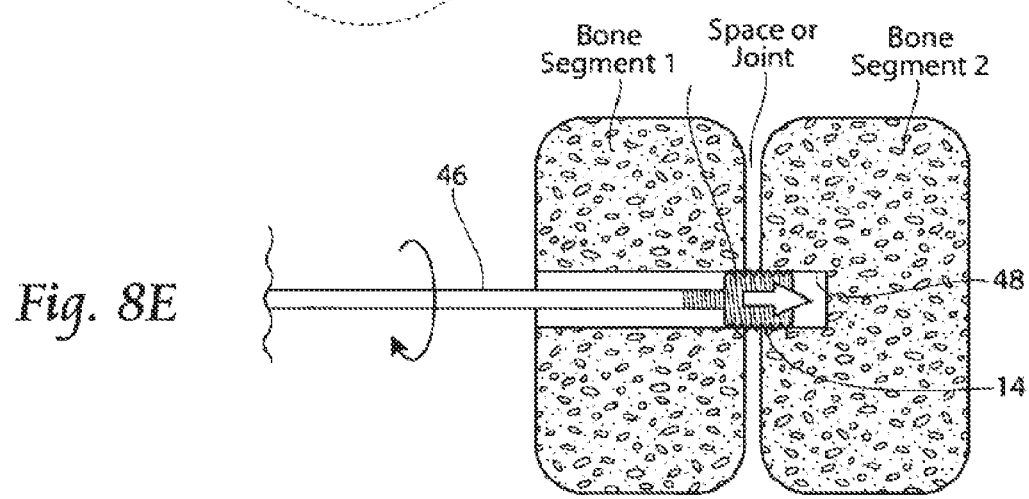
Figure 8F:
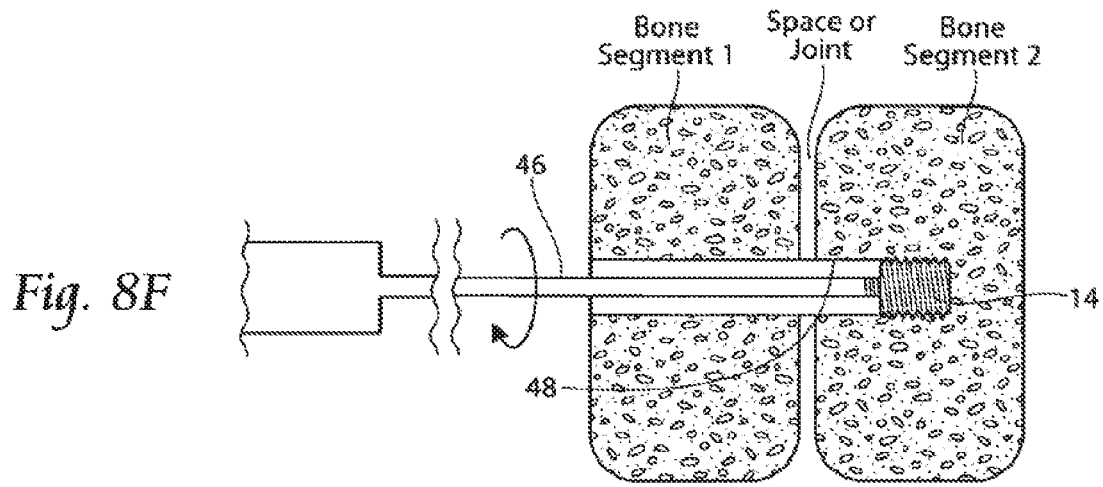
Figure 8G:
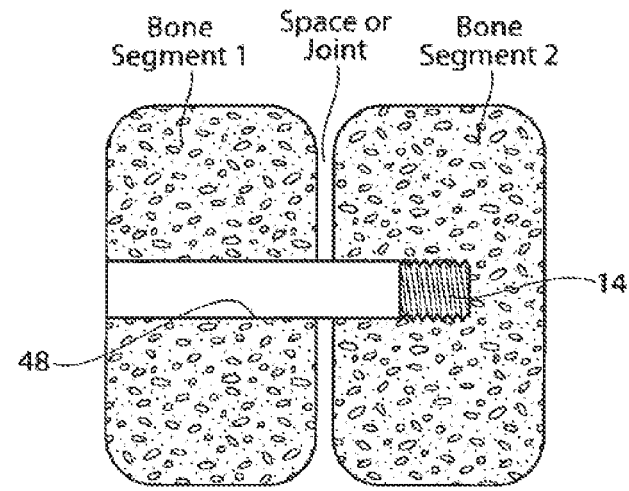

The threaded screw driver 46 is unthreaded by reverse rotation from the anchor screw 14, and the guide pin 38 is removed (see FIG. 8G). The anchor body 12 is inserted, and its threaded distal end 28 is threaded into and mated with the internal screw threads 32 of the anchor screw 14 (see FIG. 8H).

Figure 8H:
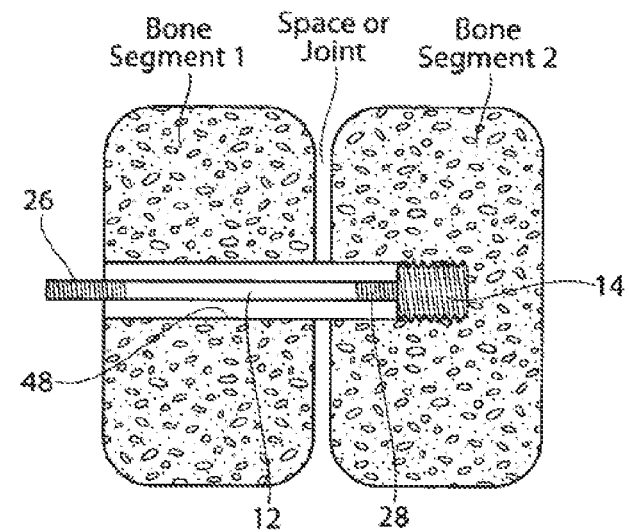

As shown in FIG. 8H, due to its purposeful size and configuration, when its threaded distal end 28 is suitably threaded to the anchor screw 14, the threaded proximal end 26 of the anchor body 12 projects an exposed distance outside the proximal end of the broached bore 48.

Figure 8I:
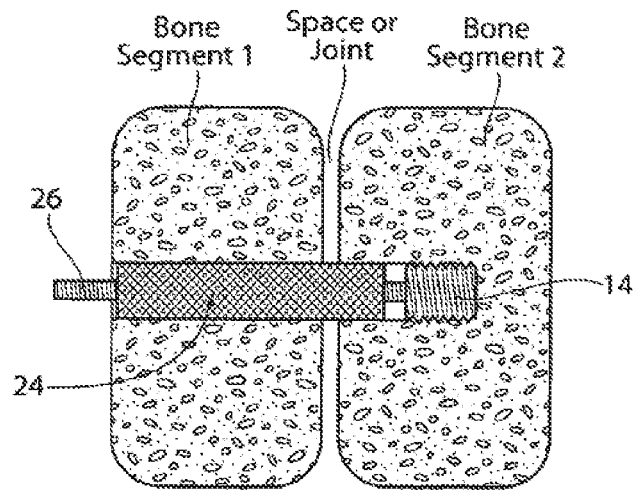

The implant structure 20 is passed over the anchor body 12 by sliding it over the anchor body 12. As FIG. 8I shows, the length of the implant structure 20 selected is less than the distance between the anchor screw 14 and the threaded proximal end 26, such that, when initially inserted and before compression is applied to the anchor body 26, the distal end of the implant structure 20 is spaced from the proximal end of the anchor screw 14 (see FIG. 8I). The distance can range, e.g., between about 4 mm to about 10 mm.

Figure 8J:
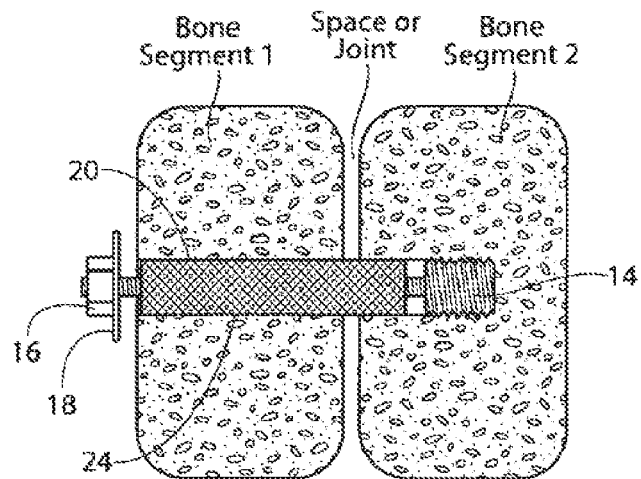
Figure 8K:
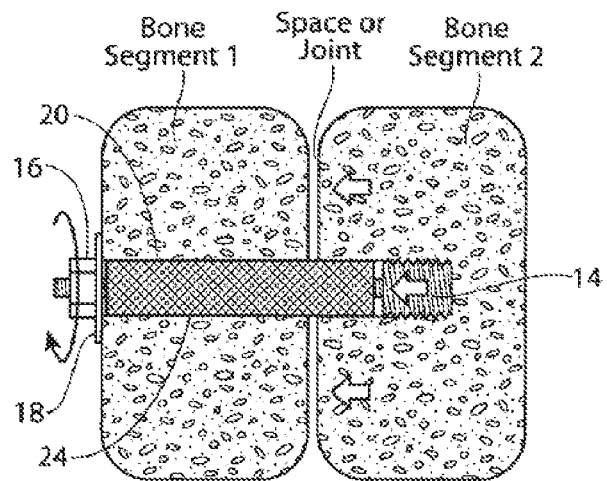
Figure 8L:
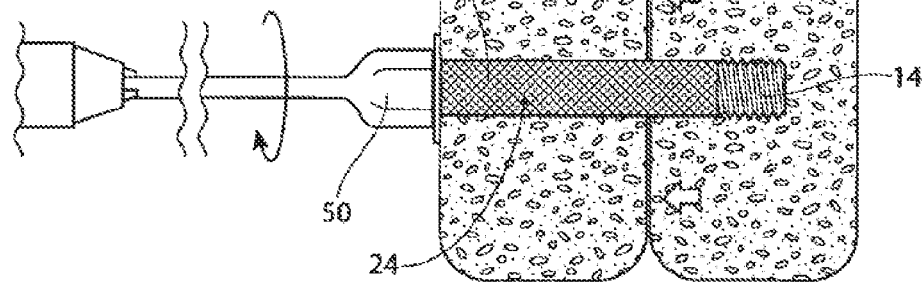

The anchor washer 18 is passed by sliding over the exposed threaded proximal end 26 of the anchor body 12 into abutment against an exterior bone surface (see FIG. 8J). The anchor nut 16 is threaded onto and mated to the threaded proximal end 26 of the anchor body 12 (see FIG. 8K). The anchor nut 16 is tightened against the anchor washer 18 using a hand (or powered) chuck 50 (see FIG. 8L), until a desired amount of compression is applied to the bone regions by the assembly 10. The compression will reduce the distance between the bone segments (as FIGS. 8K and 8L show), as the distal end 28 of the anchor body 12, affixed to the anchor screw 14 in the more distal bone segment, draws the more distal bone segment toward the more proximal bone segment, while eventually placing the implant structure 20 itself into compression within the broached bore 48 as the implant structure 20 comes into abutment against both the anchor washer 18 and the anchor screw 14, assuring intimate contact between the bony in-growth region 24 and bone within the broached bore 48.

The intimate contact created by the compression between the bony in-growth or through-growth region 24 along the surface of the implant structure 20 accelerates bony in-growth or through-growth onto, into, or through the implant structure 20, to accelerate the fusion process or fracture healing time.

As will be described in greater detail later, more than one compression stem assembly 10 can be implanted in a given bone segment. For example, as will be described later (see, e.g., FIG. 20), three such compression stem assemblies can be implanted to fuse a SI-Joint.

E. Alternative Embodiments

1. Distal Anchor Plate

Figure 31:
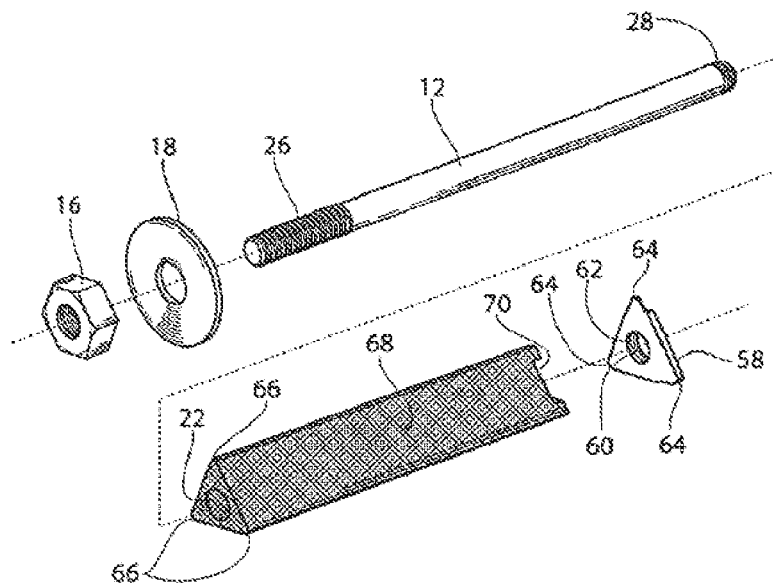
FIG. 31 is an exploded perspective view of the components of an alternative embodiment of a compression stem assembly prior to assembly.
Figure 32:
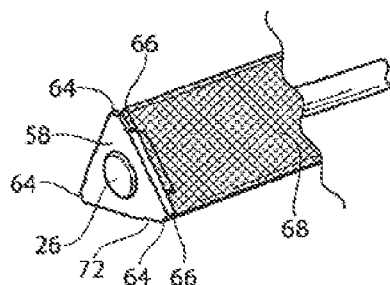
FIGS. 32 and 33 are perspective views of the alternative embodiment of a compression stem assembly shown in FIG. 31 after assembly, showing rotation of an anchor plate associated with the assembly from an aligned position (FIG. 32) to a bone-gripping position (shown in FIG. 33), to anchor the assembly in bone.
Figure 33:
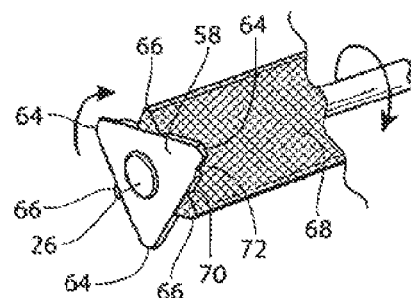

An alternative embodiment for the compression stem assembly 10 is shown in FIGS. 31 to 33. In use, the compression stem assembly 10 is sized and configured to be implanted in adjoining bone segments, which are separated by a space or joint, for the purpose of bone fixation or joint fusion, as already described.

In this embodiment (see FIG. 31), the anchor body 12, nut 16, and washer 18 are sized and configured as previously described. Likewise, the implant structure 20 is sized and configured with a generally rectilinear cross section, as also earlier described and shown in FIG. 4.

In this embodiment, instead of a threaded anchor screw 14, the distal end of the assembly 10 is anchored into bone by a generally rectilinear anchor plate 58. The anchor plate 58 is formed—e.g., by machining, or molding—from a hard, durable material usable in the prosthetic arts that is capable of cutting into and gaining purchase in bone, and that is not subject to significant bio-absorption or resorption by surrounding bone or tissue over time.

As best shown in FIGS. 31 and 32, the rectilinear anchor plate 58 is sized and configured to match the rectilinear cross section of the implant structure itself. In the illustrated arrangement, the implant structure 20 is generally triangular in cross section, and so, too, is the anchor plate 58. As such, the anchor plate 58 includes apexes 64. The sides of the anchor plate 58 between the apexes are sharpened to comprise bone cutting edges 72.

The anchor plate 58 also includes a bore 60 in its geometric center (see FIG. 31). Internal helical ridges or screw threads 62 are formed within the bore 68. The internal screw threads 62 are sized and configured to mate with the complementary external screw threads 28 on the distal region of the anchor body 12. The distal region of the anchor body 12 can thereby be threaded to the anchor plate 58 (as shown in FIG. 32). When threaded to the anchor body 12, the anchor plate 58 rotates in common with the anchor body 12 (as shown in FIG. 33).

Prior to introduction of the implant structure 20 into the broached bore 48 formed in the manner previously described (and as shown in FIGS. 8A to 8D), the anchor body 12 is passed through the bore 22 of the implant structure 20, and the anchor plate 58 is threaded to the distal threaded region 26 of the anchor body 12, which is sized to project beyond the distal end of the implant structure 20. Further, as FIG. 32 shows, the anchor plate 58 is additionally rotationally oriented in a position aligned with the distal end of the implant structure 20. In the aligned position (FIG. 32), the apexes 64 of the anchor plate 58 overlay and register with the apexes 66 of the distal end of the implant structure 20. The implant structure 20, anchor body 12, and anchor plate 58 are introduced as a unit through the broached bore 48 in the orientation shown in FIG. 32. In the aligned position, the anchor plate 58 offers no resistance to passage of the implant structure 20 through the broached bore 48.

Upon contacting the terminus of the broached bore, the proximal end of the anchor body 58 is rotated 60.degree. degrees (as shown in FIG. 33). The rotation moves the anchor plate 58 into an extended, bone-gripping position no longer aligned with the distal end of the implant structure 20 (as is shown in FIG. 33). In the extended, bone-gripping position, the apexes 64 of the triangular anchor plate 58 project radially outward from the triangular sides 68 of the implant structure 20. The anchor plate 58 presents at the distal end of the implant structure 20 an enlarged lateral surface area, larger than the cross sectional area of the implant structure itself.

Figure 34:
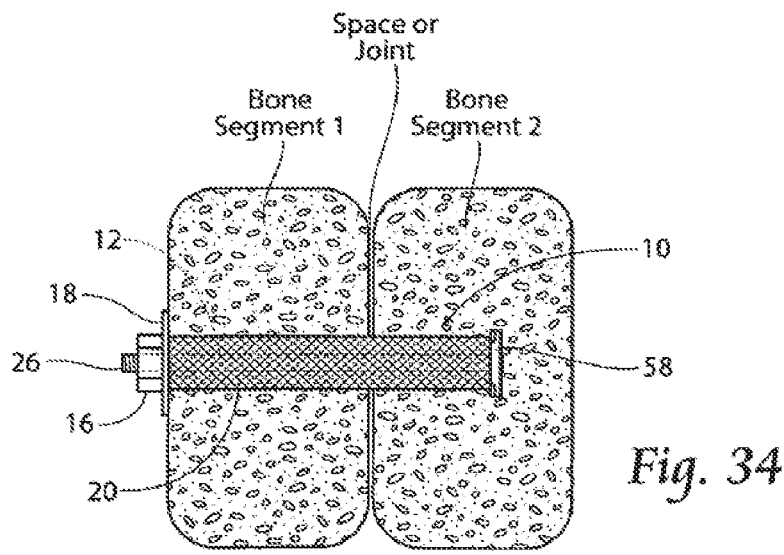
FIG. 34 is a side section view of the compression stem assembly shown in FIG. 31 assembled in adjacent bone regions, which are shown in FIG. 34 in a diagrammatically fashion for the purpose of illustration, without anatomic detail.

During rotation of the anchor plate 58 toward the bone-gripping position, the cutting edges 72 of the anchor plate 58 advance into bone and cut bone, seating the anchor plate 58 into bone in the bone segment or region (see FIG. 34). In the bone-gripping position, the anchor plate 58 anchors the distal end of the anchor body 12 into bone. The anchor plate 58 resists axial migration and separation, in much the same fashion as the anchor screw 14.

The sides 68 of the implant structure 20 at the distal end of the structure 20 preferably include cut-outs 70 (see FIGS. 31 and 32). The cut-outs 70 are sized and configured so that, when the anchor plate 58 is rotated into its bone-gripping position, the body of the anchor plate 58 adjoining the apexes detents and comes to rest within the cut outs 70, as FIG. 33 shows. Nested within the cut-outs 70, further tightening of the anchor nut 16 and washer 18 at the proximal end of the anchor body 12, as previously described, locks the anchor plate 58 in the bone-gripping, anchored position. By tightening the anchor nut, the more distal end of the anchor body 12, anchored by the plate 58 in the second bone segment, draws the second bone segment toward the first bone segment, reducing the space or joint between them, while eventually compressing the implant structure 20 between the distal anchor plate 58 and the proximal nut/washer (as FIG. 34 shows), thereby comprising a compression stem assembly 10.

2. Two Piece Compressible Implant Structure

Figure 35A:
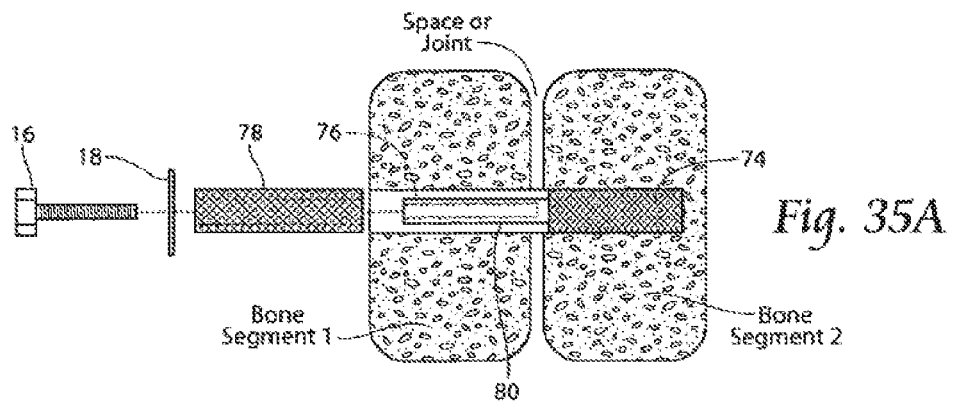
FIGS. 35A and 35B are side section views of an alternative embodiment of a compression stem assembly prior to assembly (FIG. 35A) and after assembly (FIG. 35B) in adjacent bone regions, which are shown in FIGS. 35A and 35B in a diagrammatically fashion for the purpose of illustration, without anatomic detail.
Figure 35B:
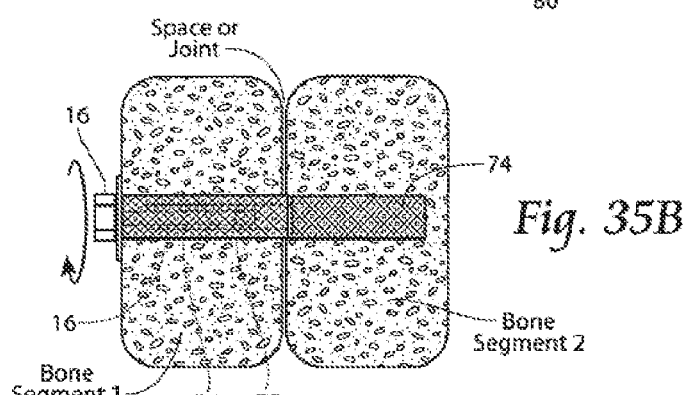

An alternative embodiment of a compressible implant structure is shown in FIGS. 35A and 35B. In use, the implant structure is sized and configured to be implanted in adjoining bone segments, which are separated by a space or joint, for the purpose of bone fixation or joint fusion, as already described.

In this embodiment (see FIG. 35A), the implant structure can possess a circular or curvilinear cross section, as previously described. Unlike previous implant structures, the implant structure 20 shown in FIG. 35A comprises two mating implant components 74 and 78.

As before described, each implant component 74 and can be formed—e.g., by machining, molding, or extrusion—from a durable material usable in the prosthetic arts that is not subject to significant bio-absorption or resorption by surrounding bone or tissue over time.

Each implant component 74 and 78 includes exterior bony in-growth or through-growth regions, as previously described.

Prior to introduction of the implant structure, a broached bore is formed through the bone segments in the manner previously described, and is shown in FIGS. 8A to 8D. The implant component 74 is sized and configured to be securely affixed within the broached bore in the most distal bone segment where the broached bore terminates, e.g., by making an interference fit and/or otherwise being secured by the use of adhesives. The implant component 74 is intended to anchor the overall implant structure.

The implant component 74 further includes a post 76 that extends through the broached bore into the most proximal bone segment, where the broached bore originates. The post 76 includes internal threads 80.

The second implant component 78 is sized and configured to be introduced into the broached bore of the most proximal bone segment. The second implant component includes an interior bore, so that the implant component 78 is installed by sliding it over the post 76 of the first implant component 74, as FIG. 35B shows.

An anchor screw 16 (desirably with a washer 18) includes external screw threads, which are sized and configured to mate with the complementary internal screw threads 80 within the post 76. Tightening the anchor screw 16 draws the first and second implant components 74 and 78 together, reducing the space or joint between the first and second bone segments and putting the resulting implant structure into compression, as FIG. 35B shows.

3. Radial Compression
(Split Implant Structure)

Figure 36A:
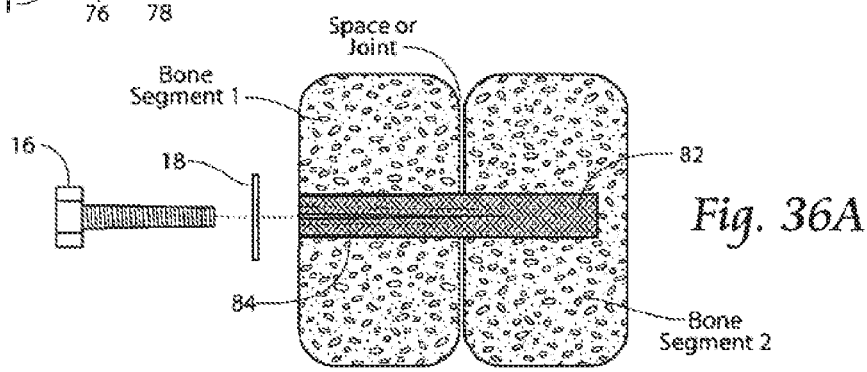
FIGS. 36A and 36B are side section views of a radially compressible implant prior to assembly (FIG. 36A) and after assembly (FIG. 36B) in adjacent bone regions, which are shown in FIGS. 36A and 36B in a diagrammatically fashion for the purpose of illustration, without anatomic detail.
Figure 36B:
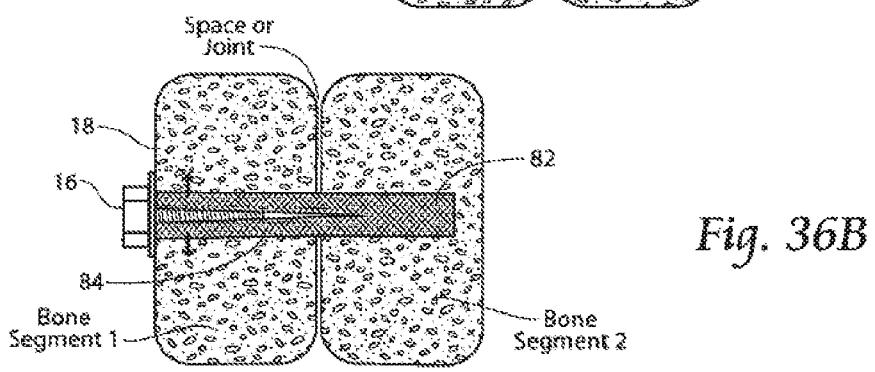
Figure 37:
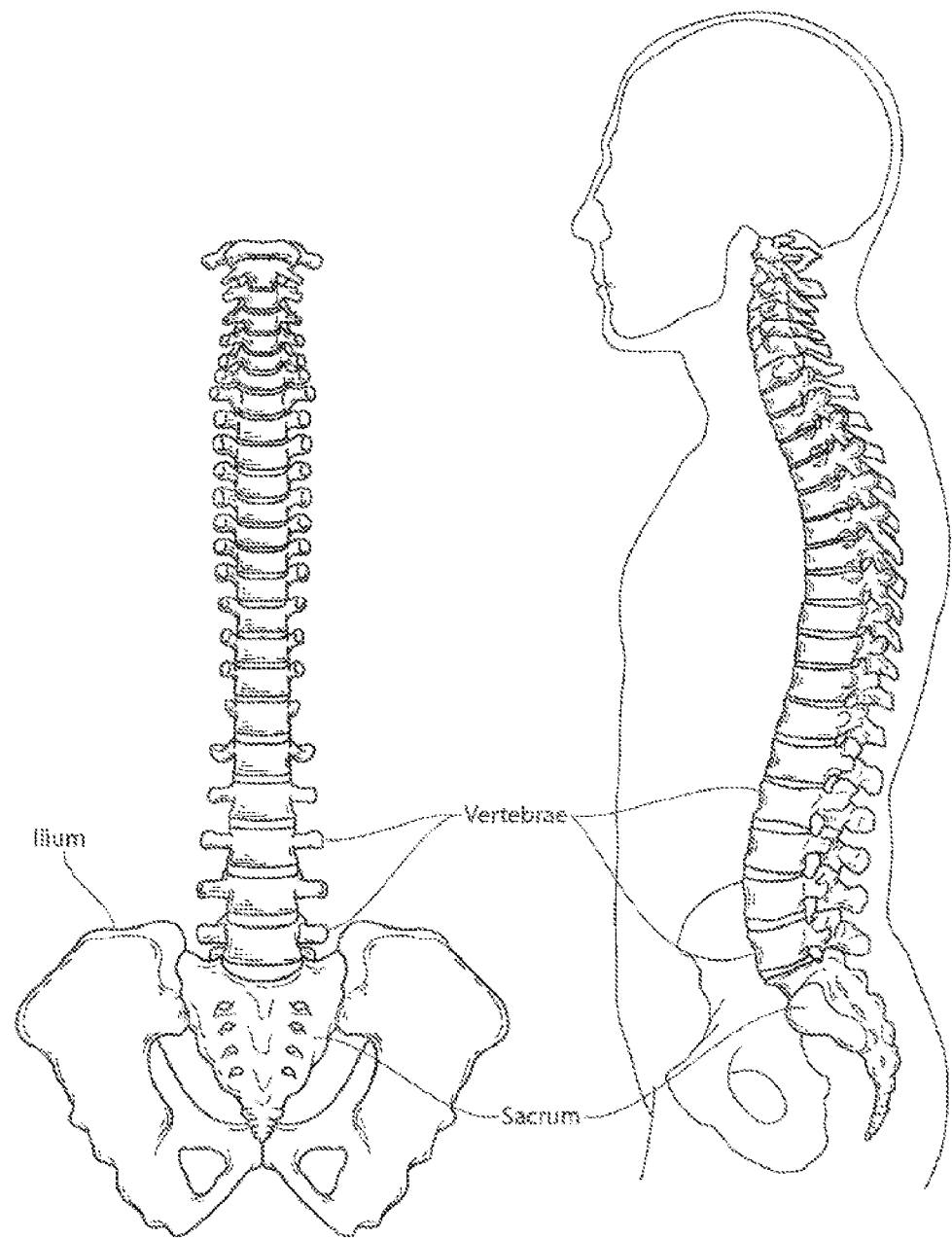
FIG. 37 is an anatomic anterior and lateral view of a human spine.
Figure 38:
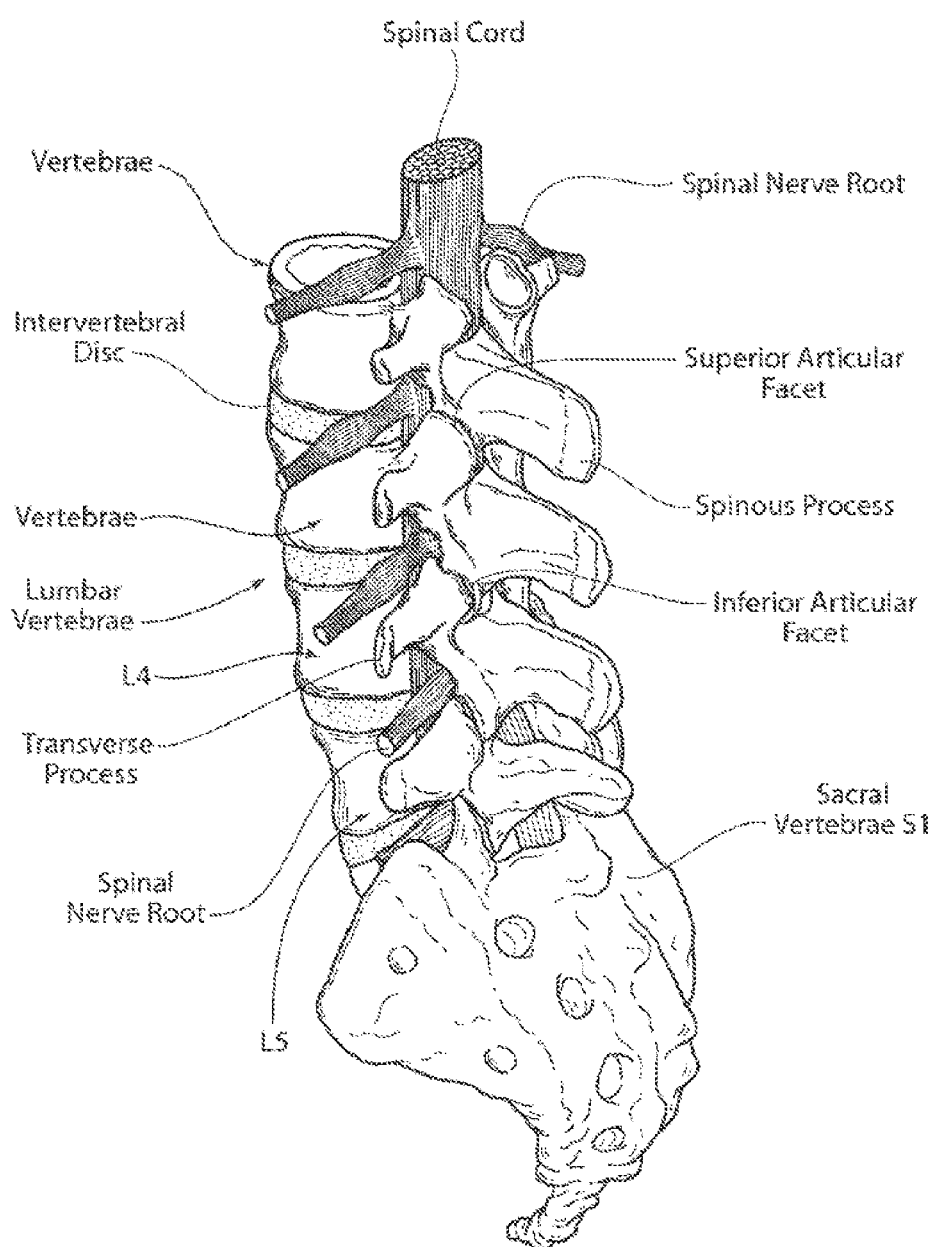
FIG. 38 is an anatomic posterior perspective view of the lumbar region of a human spine, showing lumbar vertebrae L2 to L5 and the sacral vertebrae.
Figure 39:
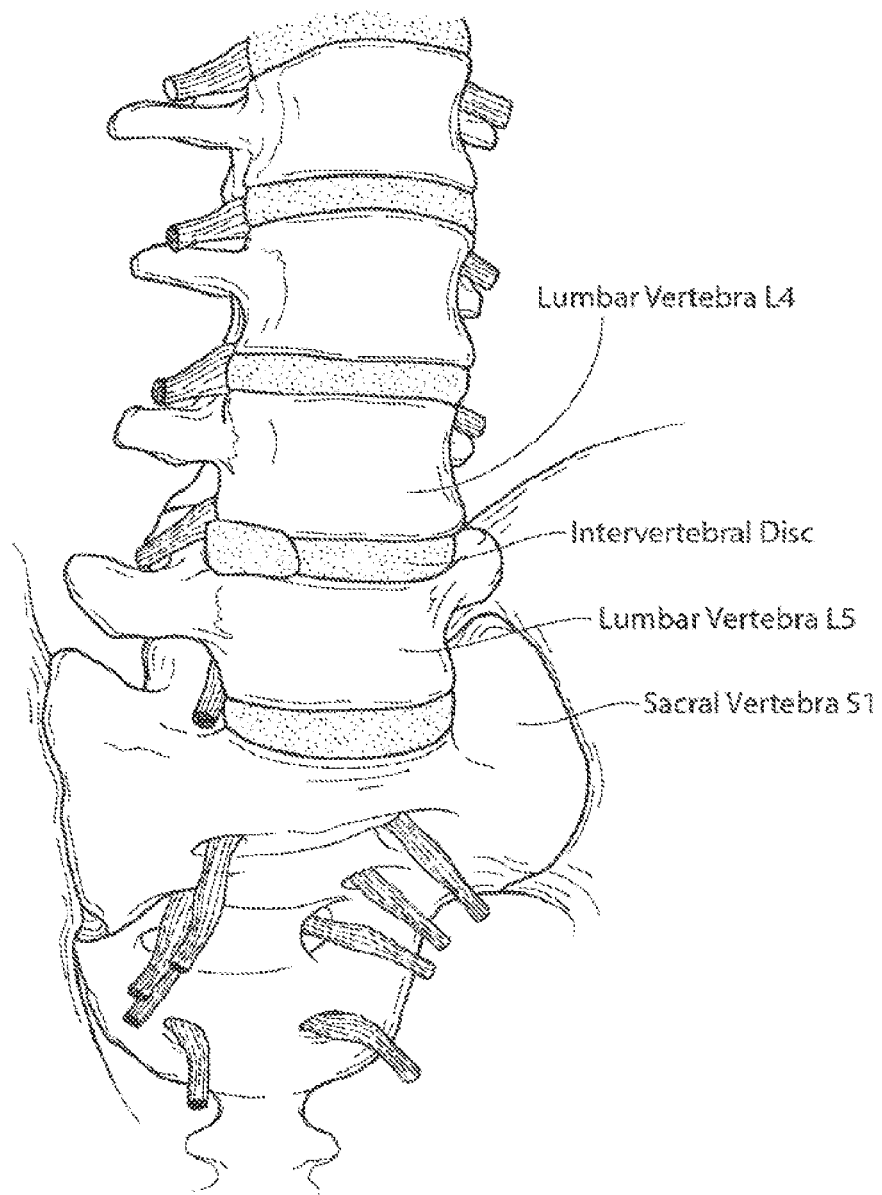
FIG. 39 is an anatomic anterior perspective view of the lumbar region of a human spine, showing lumbar vertebrae L2 to L5 and the sacral vertebrae.

An alternative embodiment of an implant structure 82 is shown in FIGS. 36A and 36B. In use, the implant structure 82 is sized and configured to be implanted in adjoining bone segments, which are separated by a space or joint, for the purpose of bone fixation or joint fusion, as already described. The implant structure 82 is sized and configured to be placed into radial compression.

The implant structure 82 includes a body that can possess a circular or curvilinear cross section, as previously described. As before described, the implant structure 82 can be formed—e.g., by machining, molding, or extrusion—from a durable material usable in the prosthetic arts that is not subject to significant bio-absorption or resorption by surrounding bone or tissue over time.

The implant structure 82 includes one or more exterior bony in-growth or through-growth regions, as previously described.

Unlike previously described implant structures, the proximal end of the implant structure 82 includes an axial region of weakness comprising a split 84. Further included is a self-tapping screw 16. The screw 16 includes a tapered threaded body. The tapered body forms a wedge of increasing diameter in the direction toward the head of the screw 16. The screw 16 is self-tapping, being sized and configured to be progressively advanced when rotated into the split 84, while creating its own thread, as FIG. 36B shows.

Prior to introduction of the implant structure 84, a broached bore is formed through the bone segments in the manner previously described, and as shown in FIGS. 8A to 8D. The implant structure 84 is introduced into the broached bore, as FIG. 36A shows. The implant structure is desirably sized and configured to be securely affixed within the broached bore in the most distal bone segment where the broached bore terminates, e.g., by making an interference fit and/or otherwise being secured by the use of adhesives. The interference fit and/or adhesives anchor the overall implant structure 84.

After introduction of the implant structure 84 into the broached bore, the self-tapping screw 16 (desirably with a washer 18) is progressively advanced by rotation into the split 84. The wedge-shape of the threaded body of the screw 16 progressively urges the body of the implant structure 84 to expand axially outward along the split 84, as FIG. 36B shows. The expansion of the diameter of the body of the implant structure 82 about the split 84 presses the proximal end of the implant structure 82 into intimate contact against adjacent bone. The radial expansion of the body of the implant structure 82 about the split 84 radially compresses the proximal end of the implant structure 82 against bone. The radial compression assures intimate contact between the bony in-growth region and bone within the broached bore, as well as resists both rotational and axial migration of the implant structure 82 within the bone segments.

F. Implant Structures Without Compression

It should be appreciated that an elongated, stem-like, implant structure 20 having a bony in-growth and/or through-growth region, like that shown in FIG. 2, can be sized and configured for the fixation of bone fractures (i.e., fixation of parts of the same bone) or for the fixation of bones which are to be fused (arthrodesed) throughout the body without association with a compression stem assembly 10 as just described, or without other means for achieving compression of the implant structure as just described. The configuration and use of representative elongated, stem-like, implant structures 20 having bony in-growth and/or through-growth regions 24 for the fixation of bone fractures (i.e., fixation of parts of the same bone) or for the fixation of bones which are to be fused, without association with a compression stem assembly 10, are described, e.g., in U.S. patent application Ser. No. 11/136,141, filed on May 24, 2005, titled "SYSTEMS AND METHODS FOR THE FIXATION OR FUSION OF BONE," now U.S. Pat. No. 7,922,765 B2, which is incorporated herein by reference.

II. Arthrodesis of the Sacroiliac Joint Using the Implant Structures

Figure 9:
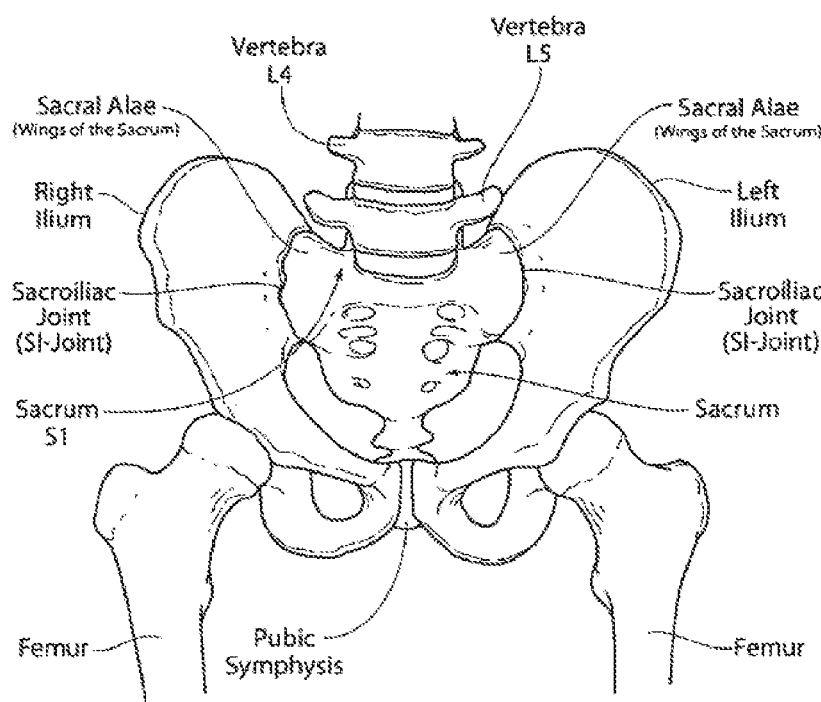
FIGS. 9 and 10 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 10:
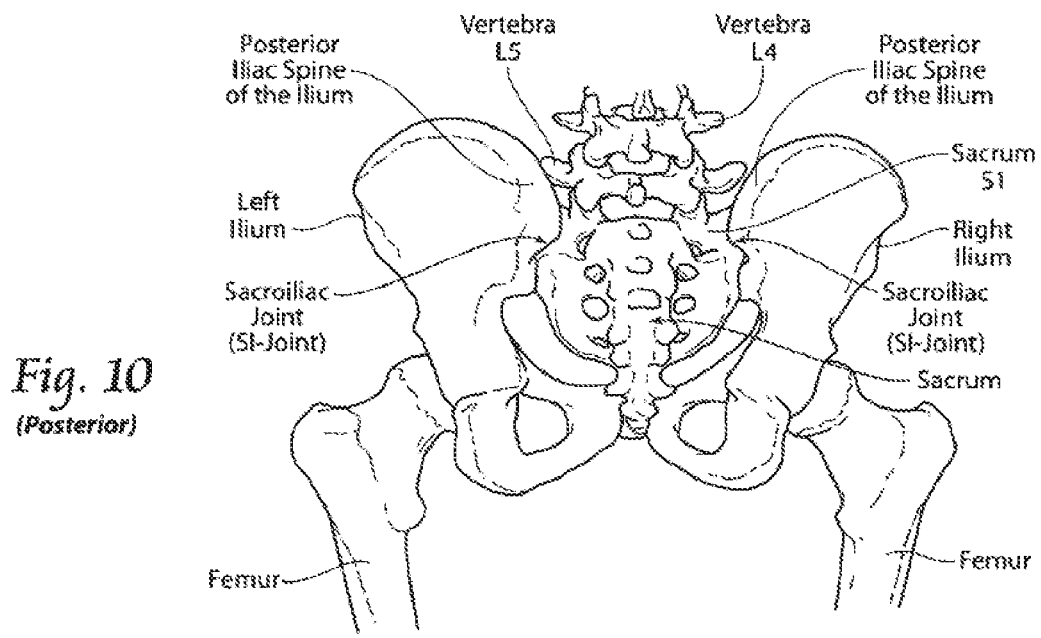

Elongated, stem-like implant structures 20 like that shown in FIG. 2 (and the alternative embodiments) make possible the fixation of the SI-Joint (shown in anterior and posterior views, respectively, in FIGS. 9 and 10) in a minimally invasive manner, with or without association with a compression stem assembly 10. These implant structures 20 can be effectively implanted through the use of two alternative surgical approaches; namely, (i) a Lateral Approach, or (ii) a Postero-Lateral Approach. Either procedure is desirably aided by conventional lateral and/or anterior-posterior (A-P) visualization techniques, e.g., using X-ray image intensifiers such as a C-arms or fluoroscopes to produce a live image feed which is displayed on a TV screen.

A. The Lateral Approach

1. Without Association of a Compression Stem Assembly

In one embodiment of a lateral approach (see FIGS. 11, 12, and 13A/B), one or more implant structures 20 are introduced (without use of a compression stem assembly 10) laterally through the ilium, the SI-Joint, and into the sacrum S1. This path and resulting placement of the implant structures 20 are best shown in FIGS. 12 and 13A/B. In the illustrated embodiment, three implant structures 20 are placed in this manner. Also in the illustrated embodiment, the implant structures 20 are triangular in cross section, but it should be appreciated that implant structures 20 of other cross sections as previously described can be used.

Before undertaking a lateral implantation procedure, the physician identifies the SI-Joint segments that are to be fixated or fused (arthrodesed) using, e.g., the Faber Test, or CT-guided injection, or X-ray/MRI of SI Joint.

Aided by lateral and anterior-posterior (A-P) c-arms, and with the patient lying in a prone position (on their stomach), the physician aligns the greater sciatic notches (using lateral visualization) to provide a true lateral position. A 3 cm incision is made starting aligned with the posterior cortex of the sacral canal, followed by blood-tissue separation to the ilium. From the lateral view, the guide pin 38 (with sleeve) (e.g., a Steinmann Pin) is started resting on the ilium at a position inferior to the sacrum S1 end plate and just anterior to the sacral canal. In A-P and lateral views, the guide pin 38 should be parallel to the S1 end plate at a shallow angle anterior (e.g., 15.degree. to 20.degree. off horizontal, as FIG. 13A shows). In a lateral view, the guide pin 38 should be posterior to the sacrum anterior wall. In the A-P view, the guide pin 38 should be superior to the S1 inferior foramen and lateral of mid-line. This corresponds generally to the sequence shown diagrammatically in FIGS. 8A and 8B. A soft tissue protector (not shown) is desirably slipped over the guide pin 38 and firmly against the ilium before removing the guide pin 38 sleeve.

Over the guide pin 38 (and through the soft tissue protector), the pilot bore 42 is drilled in the manner previously described, as is diagrammatically shown in FIG. 8C. The pilot bore 42 extends through the ilium, through the SI-Joint, and into the S1. The drill bit 40 is removed.

The shaped broach 44 is tapped into the pilot bore 42 over the guide pin 38 (and through the soft tissue protector) to create a broached bore 48 with the desired profile for the implant structure 20, which, in the illustrated embodiment, is triangular. This generally corresponds to the sequence shown diagrammatically in FIG. 8D. The triangular profile of the broached bore 48 is also shown in FIG. 11.

Figure 11:
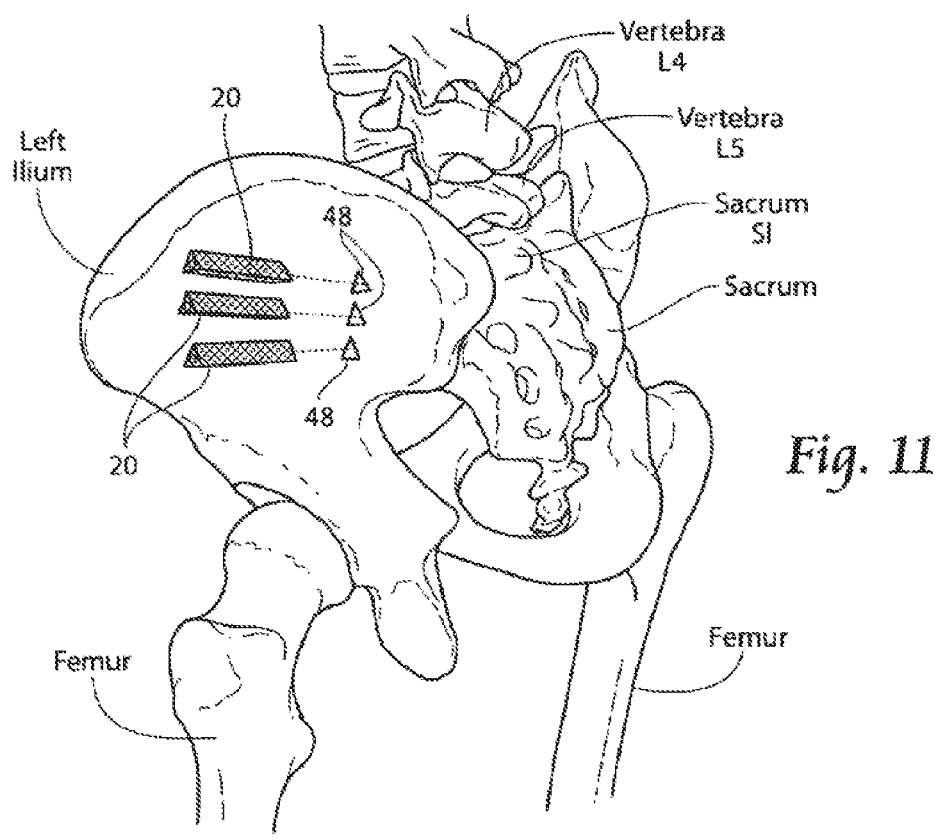
Figure 12:
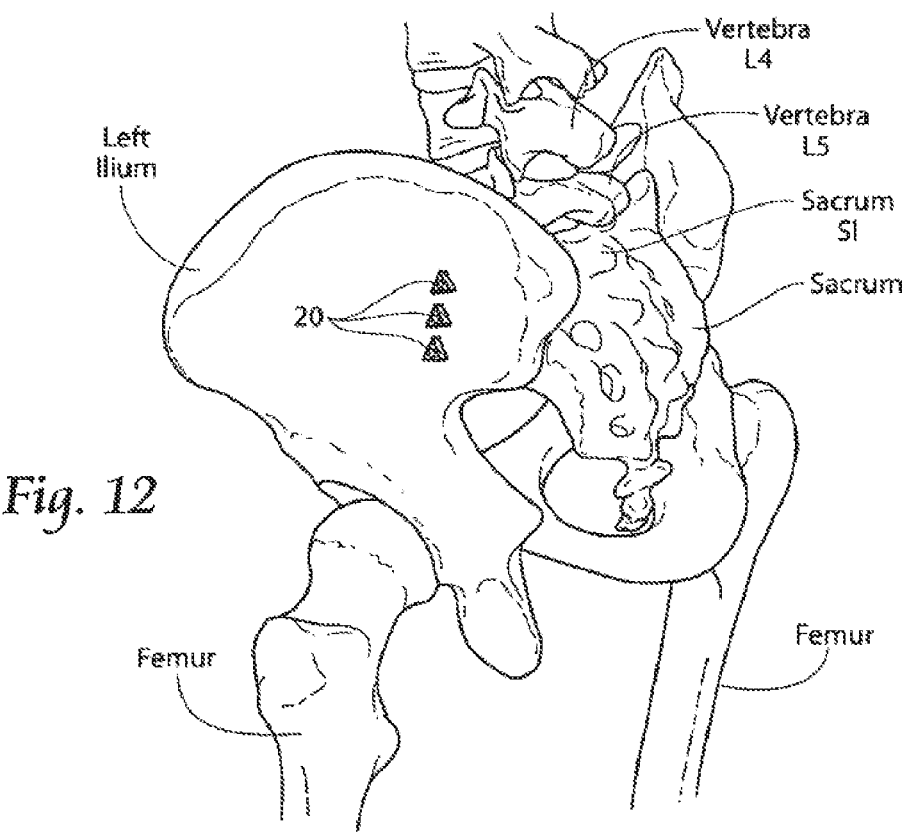
Figure 13A:
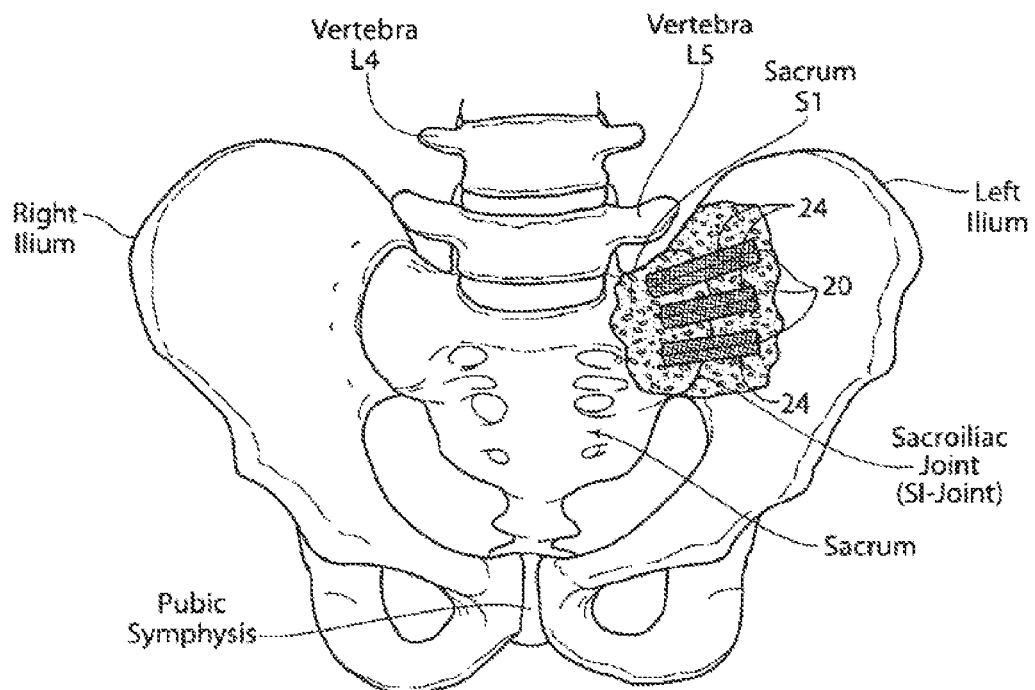
Figure 13B:
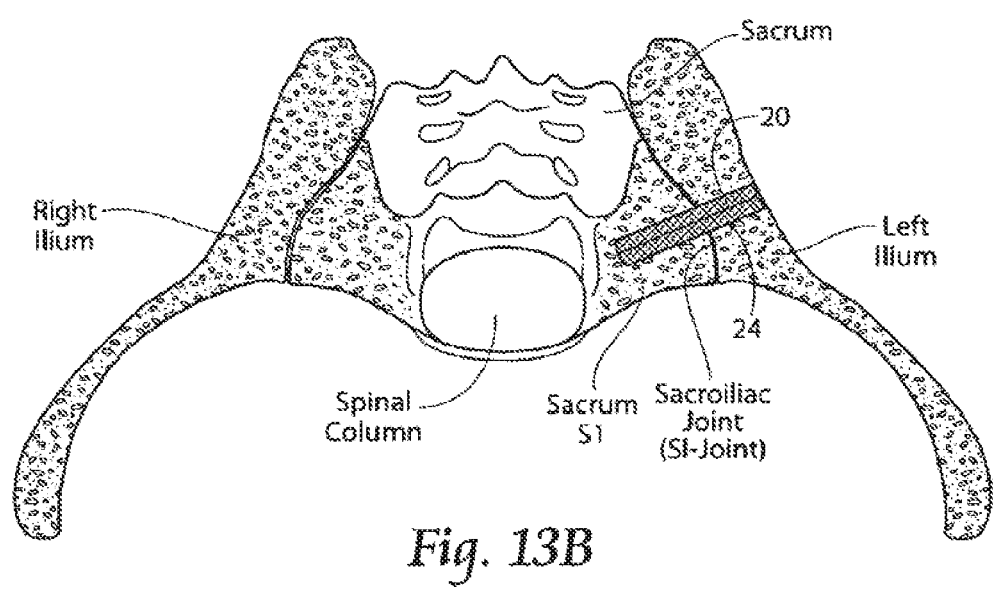

As shown in FIGS. 11 and 12, a triangular implant structure 20 can be now tapped (in this embodiment, without an associated compression sleeve assembly) through the soft tissue protector over the guide pin 38 through the ilium, across the SI-Joint, and into the S1, until the proximal end of the implant structure 20 is flush against the lateral wall of the ilium (see also FIGS. 13A and 13B). The guide pin 38 and soft tissue protector are withdrawn, leaving the implant structure 20 residing in the broached passageway, flush with the lateral wall of the ilium (see FIGS. 13A and 13B). In the illustrated embodiment, two additional implant structures 20 are implanted in this manner, as FIG. 12 best shows.

The implant structures 20 are sized according to the local anatomy. For the SI-Joint, representative implant structures 20 can range in size, depending upon the local anatomy, from about 35 mm to about 55 mm in length, and about 7 mm diameter. The morphology of the local structures can be generally understood by medical professionals using textbooks of human skeletal anatomy along with their knowledge of the site and its disease or injury. The physician is also able to ascertain the dimensions of the implant structure 20 based upon prior analysis of the morphology of the targeted bone using, for example, plain film x-ray, fluoroscopic x-ray, or MRI or CT scanning.

2. With Association of a Compression Stem Assembly

Figure 14:
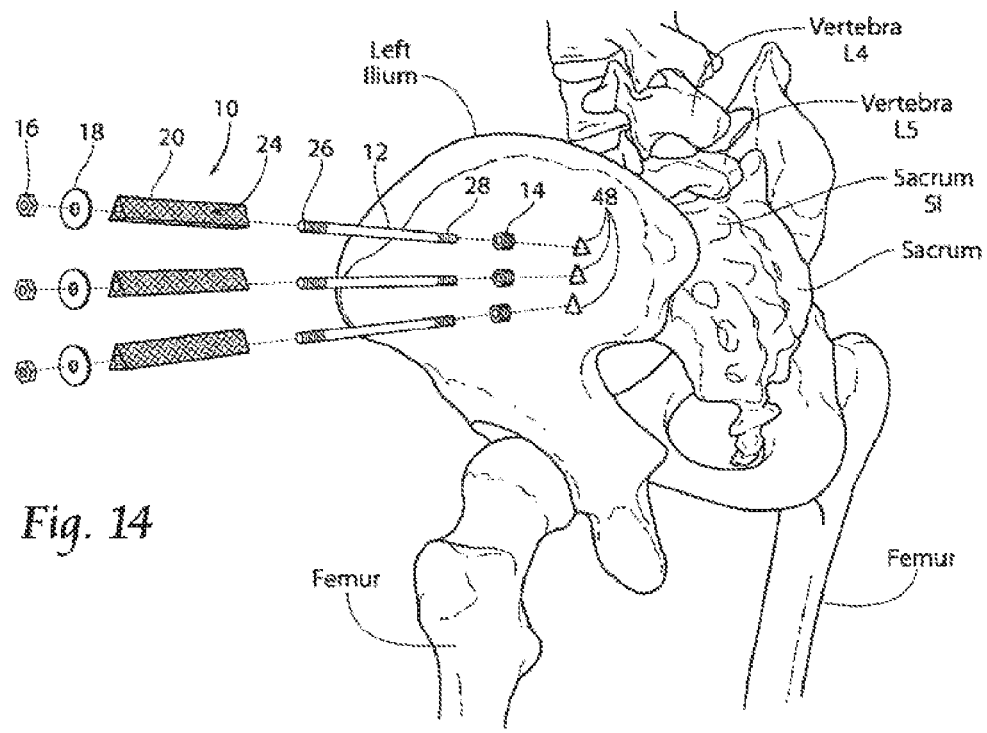
Figure 15:
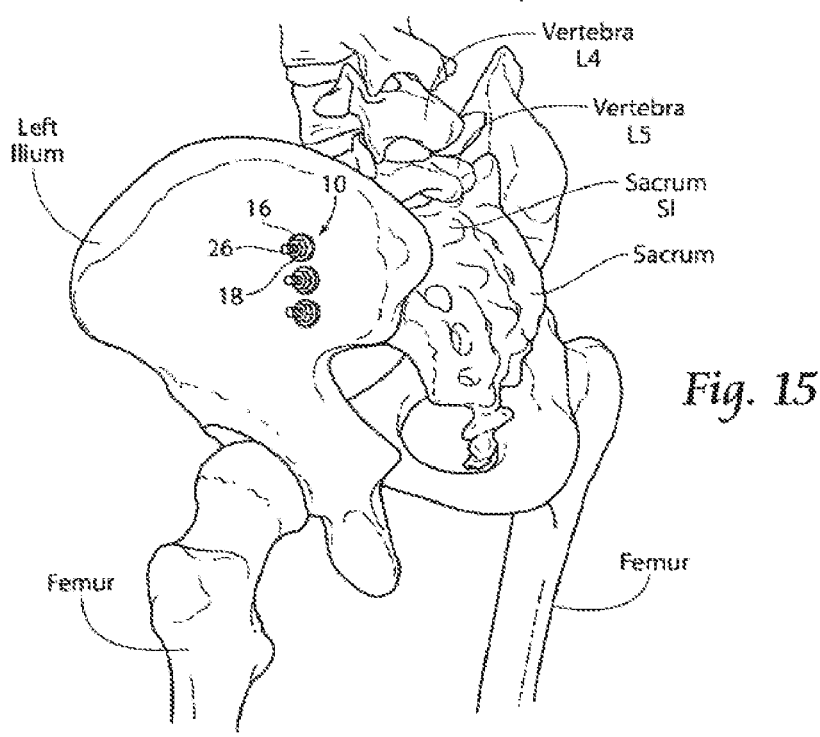
Figure 16A:
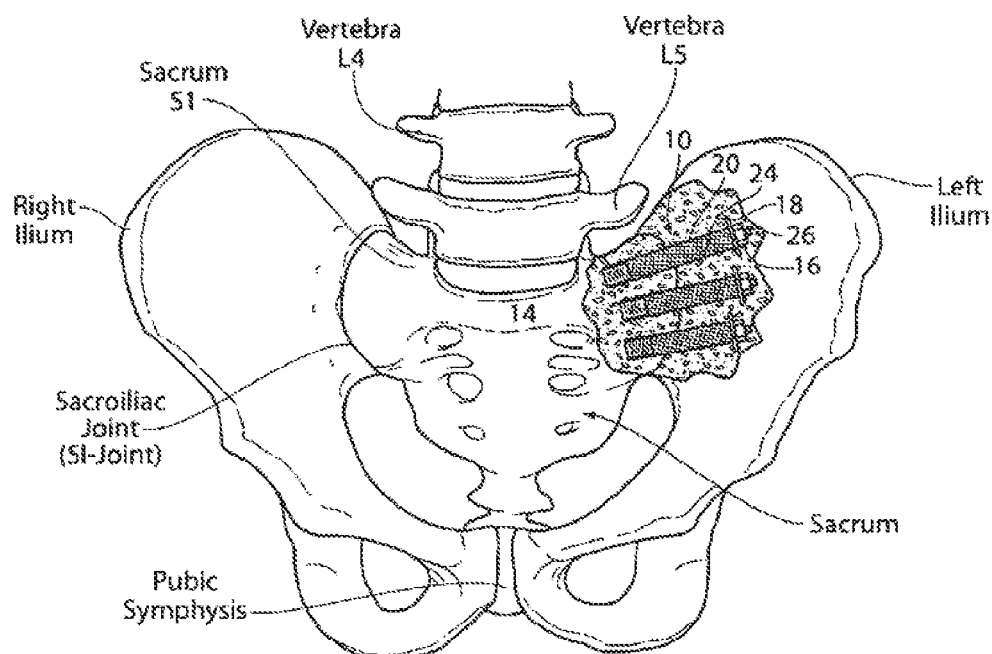

As shown in FIGS. 14 to 16A/B, the lateral approach also lends itself to the introduction of one or more implant structures 20 in association with compression stem assemblies 10, as previously described, laterally through the ilium, the SI-Joint, and into the sacrum S1. This path and resulting placement of the implant structures are best shown in FIGS. 16A and 16B. As in the embodiment shown in FIGS. 11 to 13A/B, three implant structures 20 are placed in this manner. Also, as in the embodiment shown in FIGS. 11 to 13A/B, the implant structures are triangular in cross section, but it still should be appreciated that implant structures having other cross sections, as previously described, can be used. In this embodiment of the lateral approach, the implant structure 20 is not inserted immediately following the formation of the broached bore 48. Instead, components of the compression stem assembly 10 are installed first in the broached bore 48 to receive the implant structure 20.

More particularly, following formation of the broached bore 48, as previously described, the guide pin 38 is removed, while keeping the soft tissue protector in place. The anchor screw 14 of the compression stem assembly 10 is seated in bone in the sacrum S1 beyond the terminus of the broached bore 48, in the manner generally shown in FIGS. 8E to 8G. In this arrangement, to accommodate placement of the anchor screw 14 of the compression stem assembly 10, an extent of bone in the sacrum S1 is left native and undrilled beyond the terminus of the pilot bore 42 and broached bore 48. The anchor screw 14 is advanced and buried in this extent of native and undrilled bone in the sacrum S1, as FIGS. 16A and 16B show, to be coupled to the threaded distal end 28 of the anchor body 12.

Figure 16B:
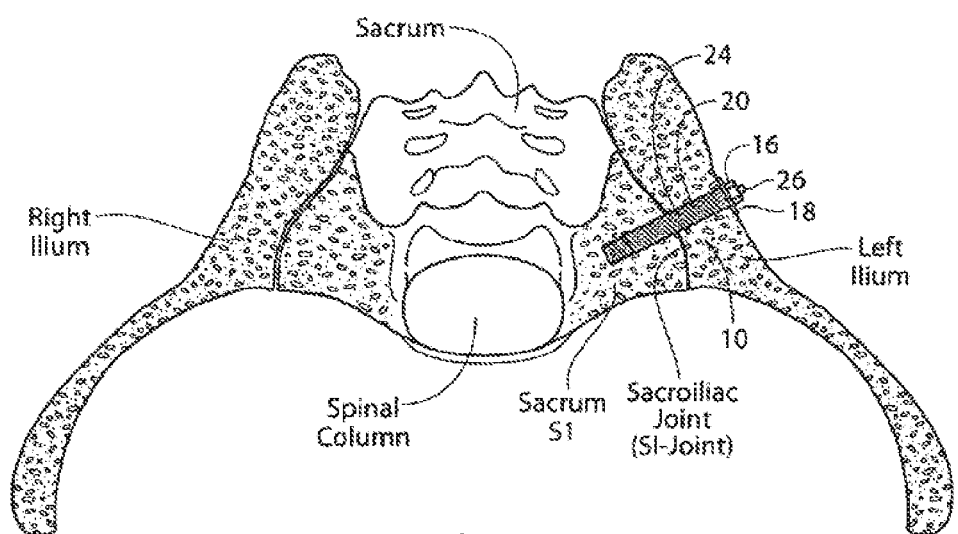
Figure 17:
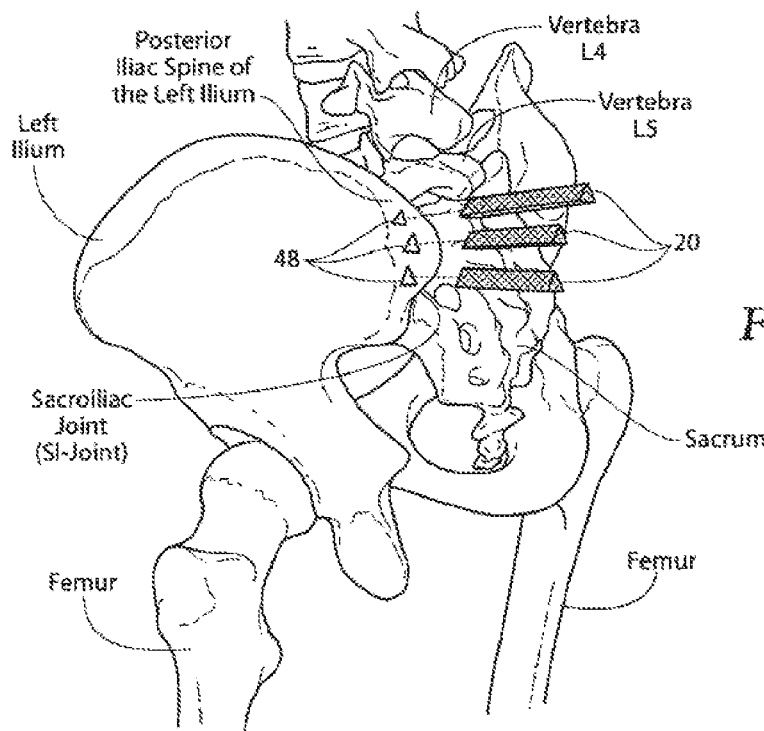

The threaded proximal end 28 of the anchor body 12 is threaded into and mated to the anchor screw 14 within the sacrum S1, as previously described and as shown in FIG. 8H, with the remainder of the anchor body 12 extending proximally through the SI-Joint and ilium, to project an exposed distance outside the lateral wall of the ilium, as FIGS. 16A and 16B show. The implant structure 20 is then placed by sliding it over the anchor body 12, until flush against the lateral wall of the ilium, as previously described and as shown in FIG. 8I. The anchor washer 18 and nut are then installed and tightened on the proximal end of the anchor body 12, as previously described and shown in FIGS. 8J to 8L, putting the assembly into compression. The resulting assembly is shown in FIGS. 15 and 16A/B.

As shown in FIGS. 14 and 15, three compression stem assemblies 10 can be installed by lateral approach across the SI-Joint. As individual compression stem assemblies are placed into compression by tightening the anchor nut 16, the implant structures of neighboring compression stem assemblies may advance to project slightly beyond the lateral wall of the ilium. If this occurs, the projecting implant structures 20 can be gently tapped further into the ilium over their respective anchor pins 12.

B. The Postero-Lateral Approach

1. Without Association of a Compression Stem Assembly

Figure 18:
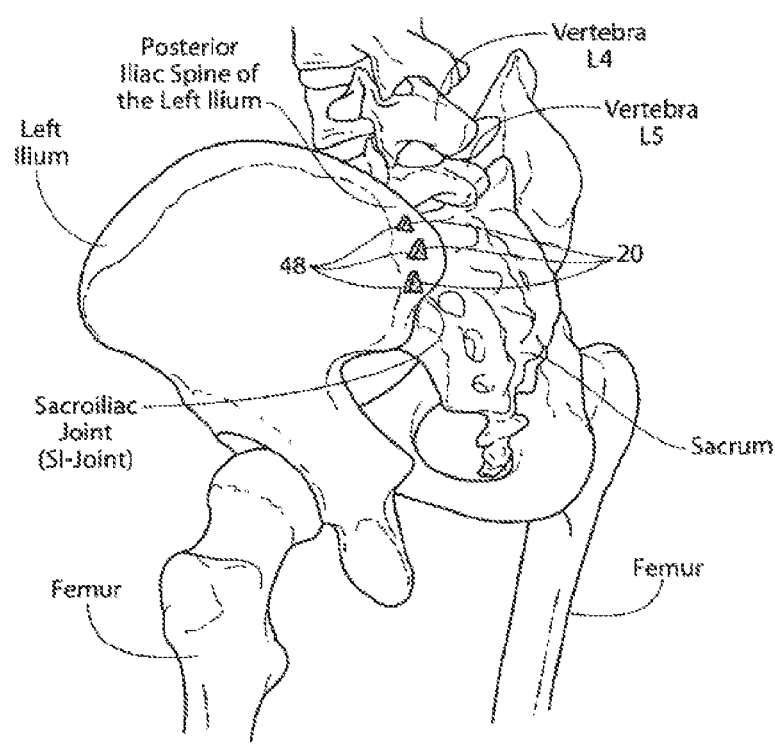
Figure 19A:
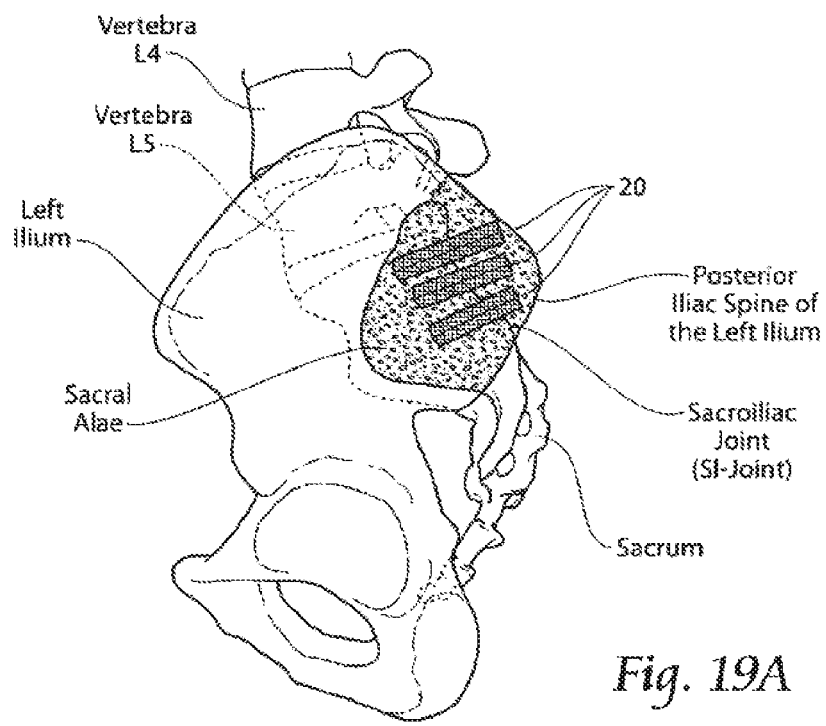
Figure 19B:
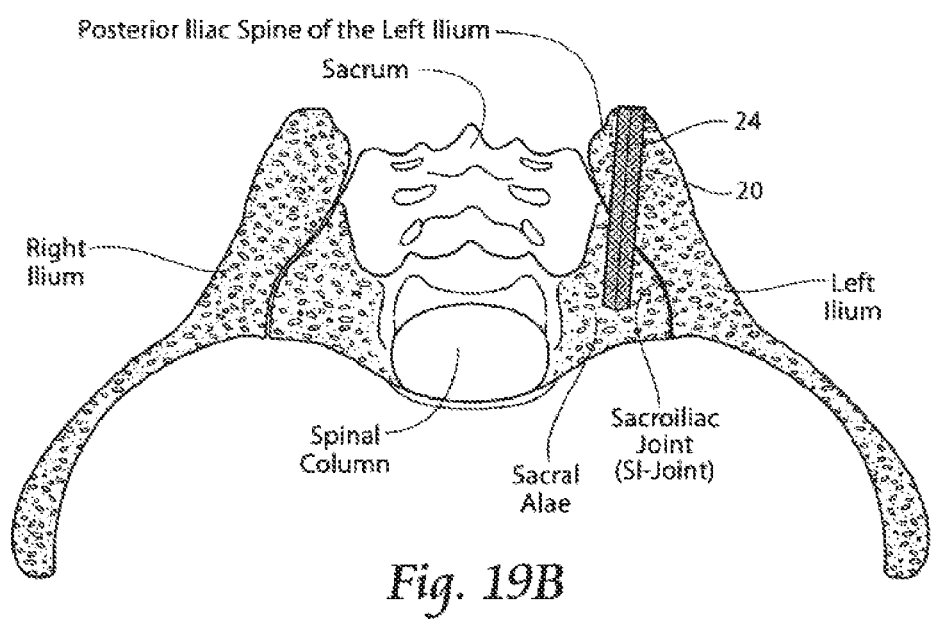

As shown in FIGS. 17 to 19A/B, one or more implant structures can be introduced (without use of a compression stem assembly 10) in a postero-lateral approach entering from the posterior iliac spine of the ilium, angling through the SI-Joint, and terminating in the sacral alae. This path and resulting placement of the implant structures 20 are best shown in FIGS. 18 and 19A/B. In the illustrated embodiment, three implant structures 20 are placed in this manner. Also in the illustrated embodiment, the implant structures 20 are triangular in cross section, but it should be appreciated that implant structures 20 of other cross sections as previously described can be used.

The postero-lateral approach involves less soft tissue disruption that the lateral approach, because there is less soft tissue overlying the entry point of the posterior iliac spine of the ilium. Introduction of the implant structure 20 from this region therefore makes possible a smaller, more mobile incision. Further, the implant structure 20 passes through more bone along the postero-lateral route than in a strictly lateral route, thereby involving more surface area of the SI-Joint and resulting in more fusion and better fixation of the SI-Joint. Employing the postero-lateral approach also makes it possible to bypass all nerve roots, including the L5 nerve root.

The set-up for a postero-lateral approach is generally the same as for a lateral approach. It desirably involves the identification of the SI-Joint segments that are to be fixated or fused (arthrodesed) using, e.g., the Faber Test, or CT-guided injection, or X-ray/MRI of SI Joint. It is desirable performed with the patient lying in a prone position (on their stomach) and is aided by lateral and anterior-posterior (A-P) c-arms. The same surgical tools are used to form the pilot bore 42 over a guide pin 38, except the path of the pilot bore 42 now starts from the posterior iliac spine of the ilium, angles through the SI-Joint, and terminates in the sacral alae. The pilot bore 42 is shaped into the desired profile using a broach, as before described (shown in FIG. 17), and the implant structure 20 is inserted into the broached bore 48 the manner shown in FIGS. 18 and 19A/B. The triangular implant structure 20 is tapped (in this embodiment, without an associated compression sleeve assembly 10) through the soft tissue protector over the guide pin 38 from the posterior iliac spine of the ilium, angling through the SI-Joint, and terminating in the sacral alae, until the proximal end of the implant structure 20 is flush against the posterior iliac spine of the ilium, as FIG. 18 shows. As shown in FIGS. 17 to 19A/B, three implant structures 20 are introduced in this manner. Because of the anatomic morphology of the bone along the postero-lateral route, it may be advisable to introduce implant structures of difference sizes, with the most superior being the longest in length, and the others being smaller in length.

2. With Association of a Compression Stem Assembly

Figure 20:
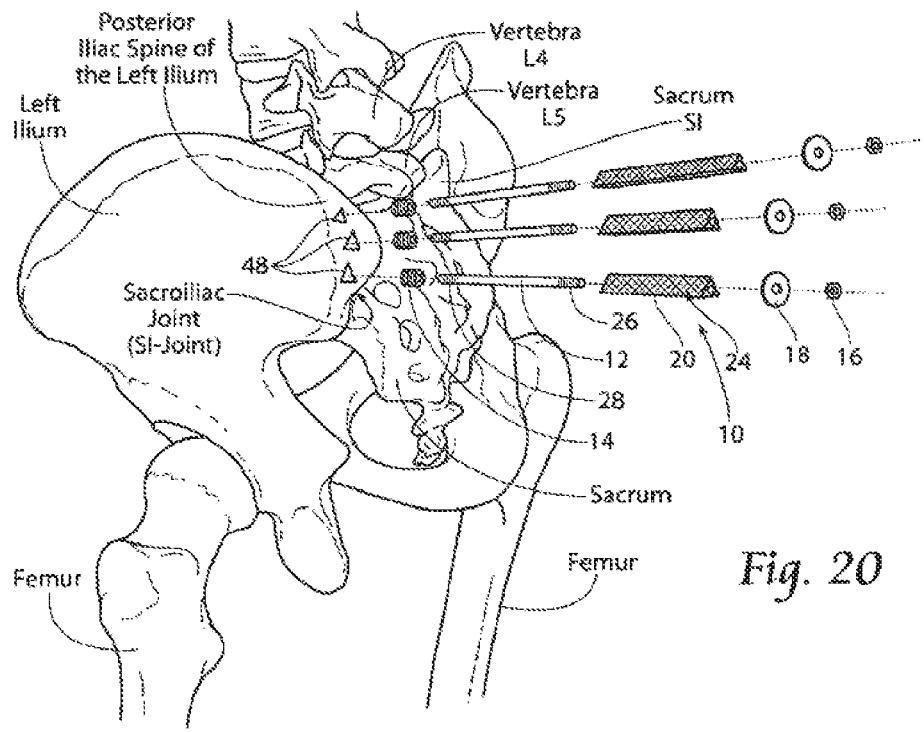
Figure 21:
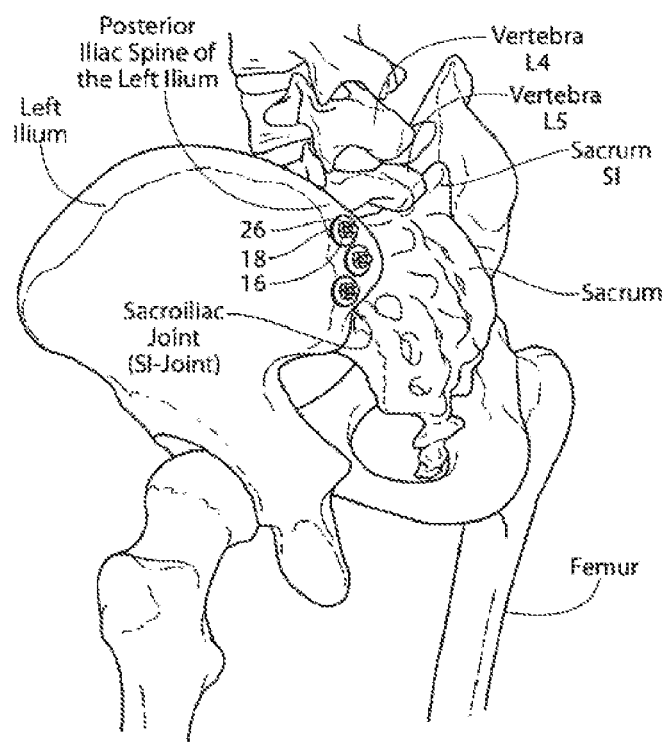
Figure 22A:
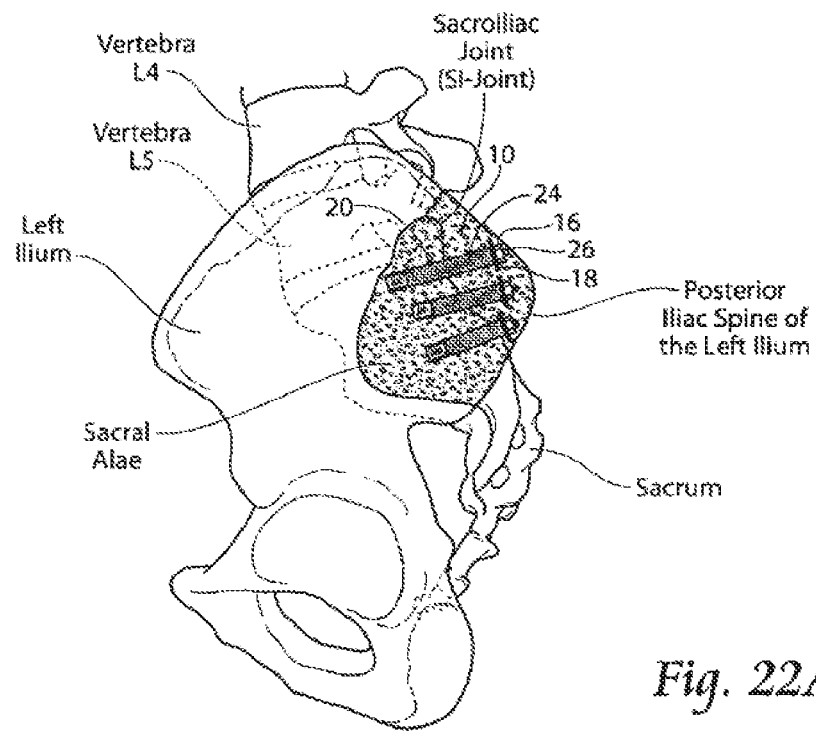

As shown in FIGS. 20 to 22A/B, the postero-lateral approach also lends itself to the introduction of one or more implant structures 20 in association with compression stem assemblies 10, as previously described, entering from the posterior iliac spine of the ilium, angling through the SI-Joint, and advancing into the sacral alae. This path and resulting placement of the implant structures 20 with compression stem assemblies 10 are best shown in FIGS. 22A/B. As in the embodiment shown in FIGS. 17 to 19A/B, three implant structures 20 are placed in this-manner. Also, as in the embodiment shown in FIGS. 17 to 19A/B, the implant structures 20 are triangular in cross section, but it still should be appreciated that implant structures 20 of other cross sections as previously described can be used. In this embodiment of the posterior-lateral approach, the implant structure 20 is not inserted immediately following the formation of the broached bore 48. Instead, components of the compression stem assembly 10 are installed in the broached bore 48 first to receive the implant structure 20, as have been previously described as is shown in FIG. 20.

As before explained, the set-up for a postero-lateral approach is generally the same as for a lateral approach. It is desirable performed with the patient lying in a prone position (on their stomach) and is aided by lateral and anterior-posterior (A-P) c-arms. The same surgical tools are used to form the pilot bore 42 over a guide pin 38 that starts from the posterior iliac spine of the ilium, angles through the SI-Joint, and terminates in the sacral alae. The pilot bore 42 is shaped into the desired profile using a broach 44, as before described (and as shown in FIG. 20). In this arrangement, to accommodate placement of the anchor screw 14 of the compression stem assembly 10, an extent of bone in the sacral alae is left native and undrilled beyond the terminus of the formed pilot bore 42 and broached bore 48. The anchor screw 14 is advanced and buried in this extent of native and undrilled bone in the sacral alae, as FIGS. 22A/B show, to be coupled to the threaded distal end 28 of the anchor body 12. Due to the morphology of the sacral alae, the anchor screw 14 may be shorter than it would be if buried in the sacrum S1 by the lateral approach.

Figure 22B:
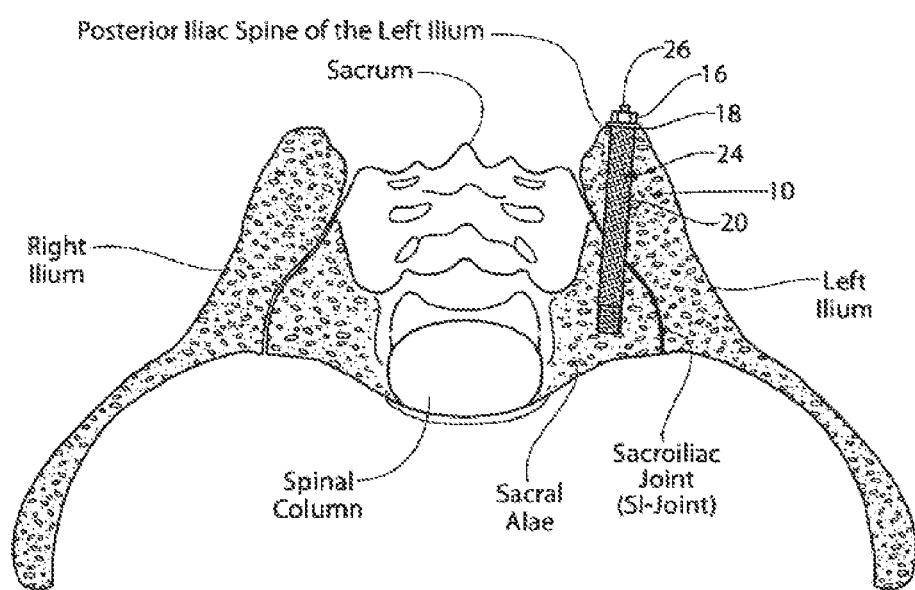

The threaded proximal end 28 of the anchor body 12 is threaded into and mated to the anchor screw 14 within the sacral alae, as previously described and as shown in FIG. 8H, with the remainder of the anchor body 12 extending proximally through the SI-Joint to project an exposed distance outside the superior iliac spine of the ilium, as FIGS. 21 to 22A/B show. The implant structure 20 is then placed by sliding it over the anchor body 12, until flush against the superior iliac spine of the ilium, as previously described and as shown in FIG. 8I. The anchor washer 18 and nut are then installed and tightened on the proximal end of the anchor body 12, as previously described and shown in FIGS. 8J to 8L, putting the assembly 10 into compression. The resulting assembly 10 is shown in FIGS. 21 and 22A/B.

As shown in FIGS. 20 and 21, three compression stem assemblies 10 can be installed by postero-lateral approach across the SI-Joint. As before explained, as individual compression stem assemblies 10 are placed into compression by tightening the anchor nut 16, the implant structures 20 of neighboring compression stem assemblies 10 may advance to project slightly beyond the superior iliac spine of the ilium. If this occurs, the projecting implant structures 20 can be gently tapped further into the superior iliac spine of the ilium over their respective anchor bodies 12.

C. Conclusion

Using either a posterior approach or a postero-lateral approach, one or more implant structures 20 can be individually inserted in a minimally invasive fashion, with or without association of compression stem assemblies 10, or combinations thereof, across the SI-Joint, as has been described. Conventional tissue access tools, obturators, cannulas, and/or drills can be used for this purpose. No joint preparation, removal of cartilage, or scraping are required before formation of the insertion path or insertion of the implant structures 20, so a minimally invasive insertion path sized approximately at or about the maximum outer diameter of the implant structures 20 need be formed.

The implant structures 20, with or without association of compression stem assemblies 10, obviate the need for autologous bone graft material, additional pedicle screws and/or rods, hollow modular anchorage screws, cannulated compression screws, threaded cages within the joint, or fracture fixation screws.

In a representative procedure, one to six, or perhaps eight, implant structures 20 might be needed, depending on the size of the patient and the size of the implant structures 20. After installation, the patient would be advised to prevent loading of the SI-Joint while fusion occurs. This could be a six to twelve week period or more, depending on the health of the patient and his or her adherence to post-op protocol.

The implant structures 20 make possible surgical techniques that are less invasive than traditional open surgery with no extensive soft tissue stripping. The lateral approach and the postero-lateral approach to the SI-Joint provide straightforward surgical approaches that complement the minimally invasive surgical techniques. The profile and design of the implant structures 20 minimize rotation and micromotion. Rigid implant structures 20 made from titanium provide immediate post-op SI Joint stability. A bony in-growth region 24 comprising a porous plasma spray coating with irregular surface supports stable bone fixation/fusion. The implant structures 20 and surgical approaches make possible the placement of larger fusion surface areas designed to maximize post-surgical weight bearing capacity and provide a biomechanically rigorous implant designed specifically to stabilize the heavily loaded SI-Joint.

III. Arthrodesis of the Sacroiliac Joint Using Other Structures

The Lateral Approach and the Postero-Lateral Approach to the SI-Joint, aided by conventional lateral and/or anterior-posterior (A-P) visualization techniques, make possible the fixation of the SI-Joint in a minimally invasive manner using other forms of fixation/fusion structures. Either approach makes possible minimal incision size, with minimal soft tissue stripping, minimal tendon irritation, less pain, reduced risk of infection and complications, and minimal blood loss.

Figure 23:
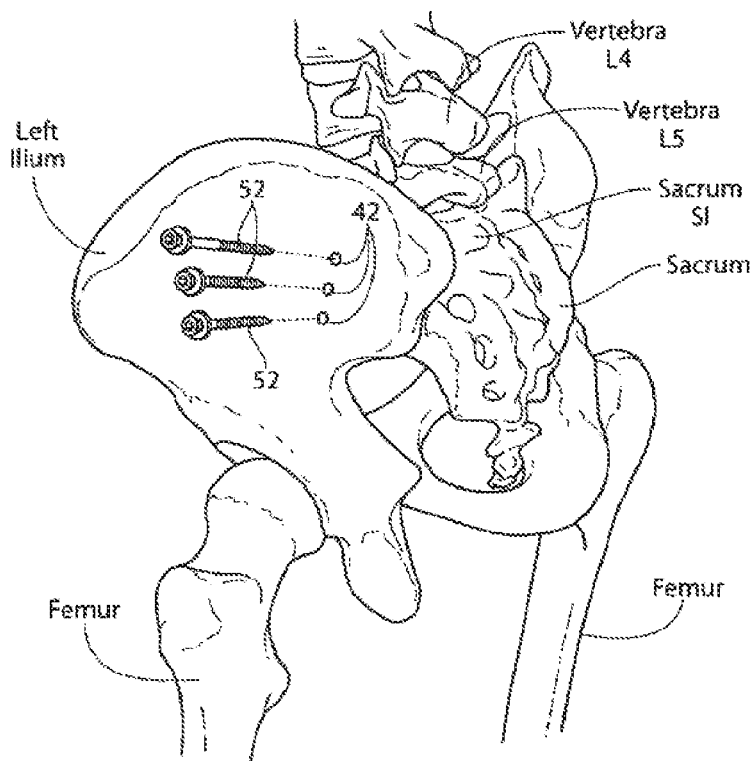
FIGS. 23 and 24A and 24B are anatomic views showing, respectively, in exploded perspective, assembled anterior view, and assembled axial section view, the implantation of a screw-like structure for the fixation of the SI-Joint using a lateral approach laterally through the ilium, the SI-Joint, and into the sacrum S1.
Figure 24A:
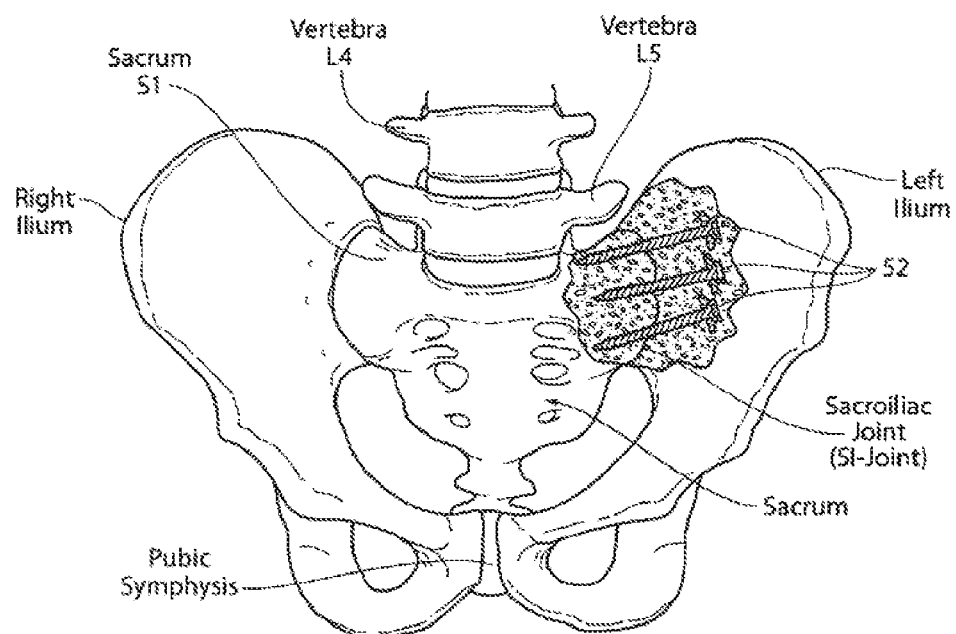
Figure 24B:
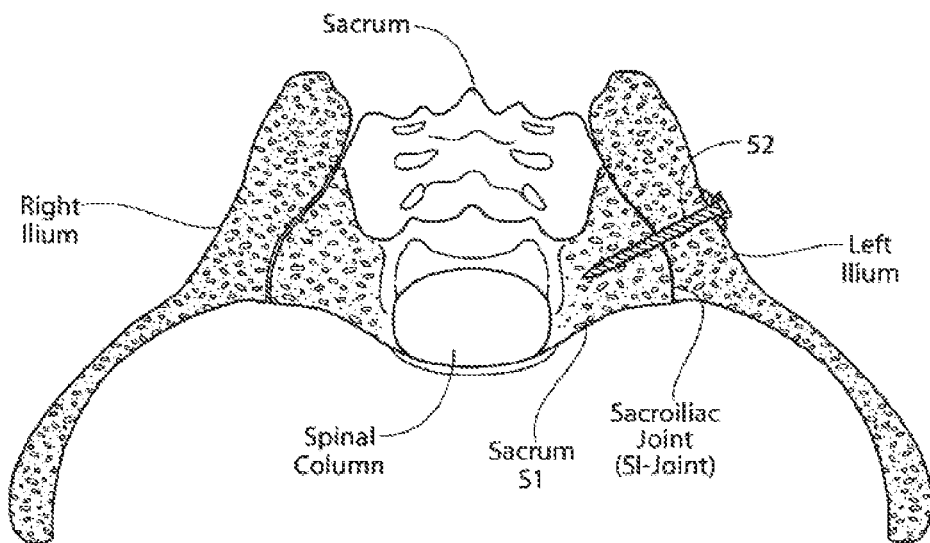

For example (see FIGS. 23 and 24A/B), one or more screw-like structures 52, e.g., a hollow modular anchorage screw, or a cannulated compression screw, or a fracture fixation screw, can be introduced using the lateral approach described herein, being placed laterally through the ilium, the SI-Joint, and into the sacrum S1. This path and resulting placement of the screw-like structures 52 are shown in FIGS. 23 and 24A/B. Desirably, the screw-like structure carry a bony in-growth material or a bony through-growth configuration, as described, as well as being sized and configured to resist rotation after implantation.

Figure 25:
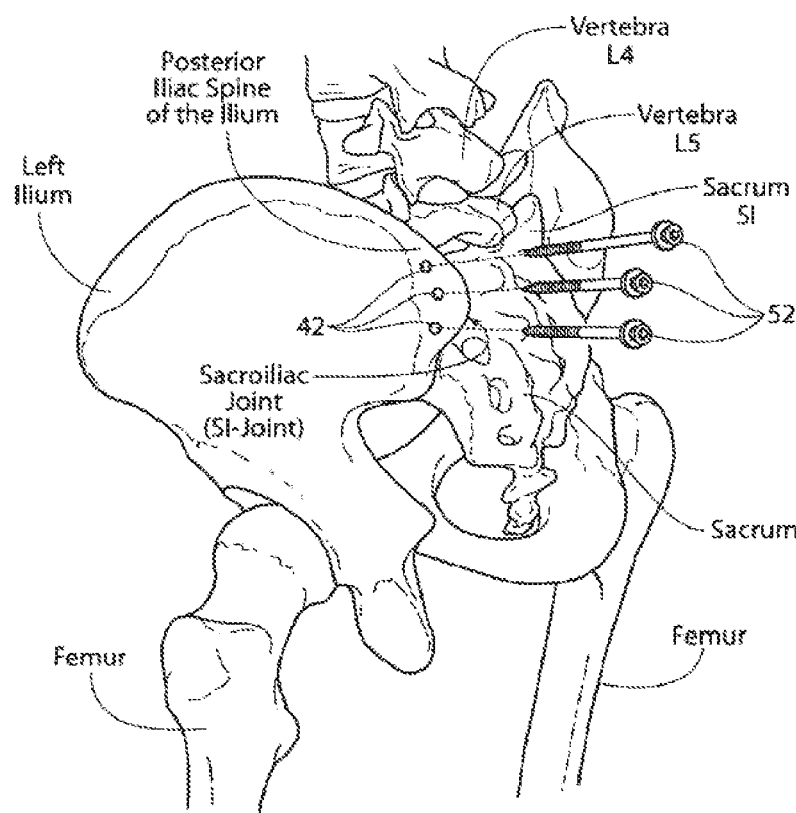
FIGS. 25 and 26A and 26B are anatomic views showing, respectively, in exploded perspective, assembled lateral view, and assembled axial section view, the implantation of a screw-like structure for the fixation of the SI-Joint using a postero-lateral approach entering from the posterior iliac spine of the ilium, angling through the SI-Joint, and terminating in the sacral alae.
Figure 26A:
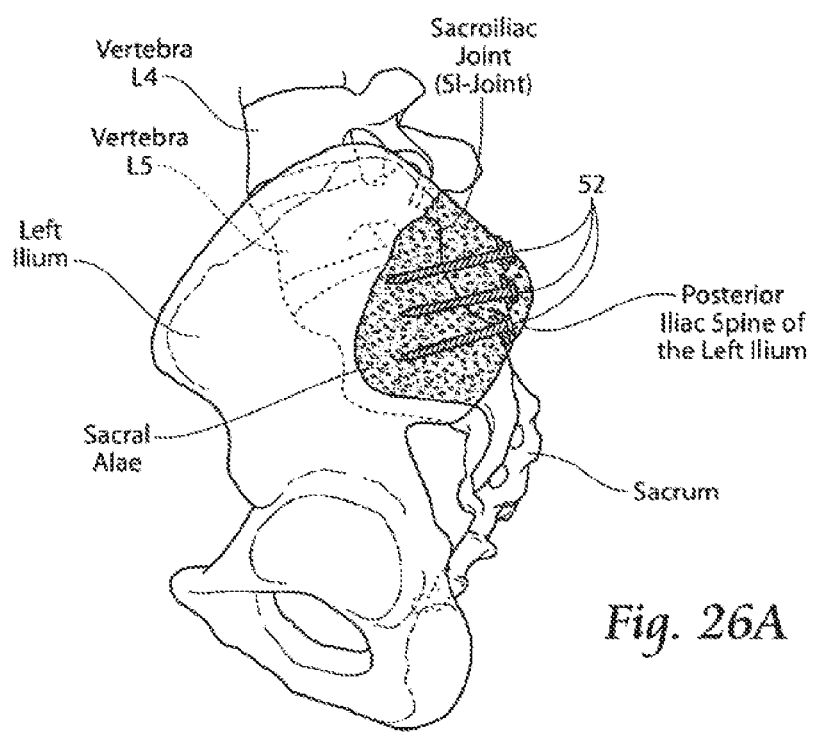
Figure 26B:
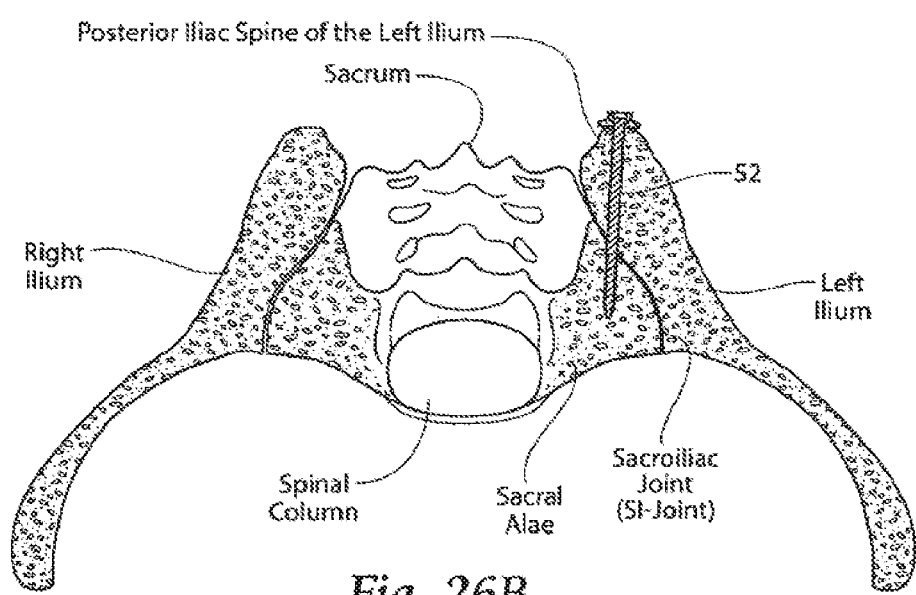

Likewise, one or more of the screw-like structures 52 can be introduced using the postero-lateral approach described herein, entering from the posterior iliac spine of the ilium, angling through the SI-Joint, and terminating in the sacral alae. This path and resulting placement of the screw-like structure are shown in FIGS. 25 and 26A/B. Desirably, the screw-like structures 52 carry a bony in-growth material or a bony through-growth configuration, as described, as well as being sized and configured to resist rotation after implantation, as before described.

Figure 27:
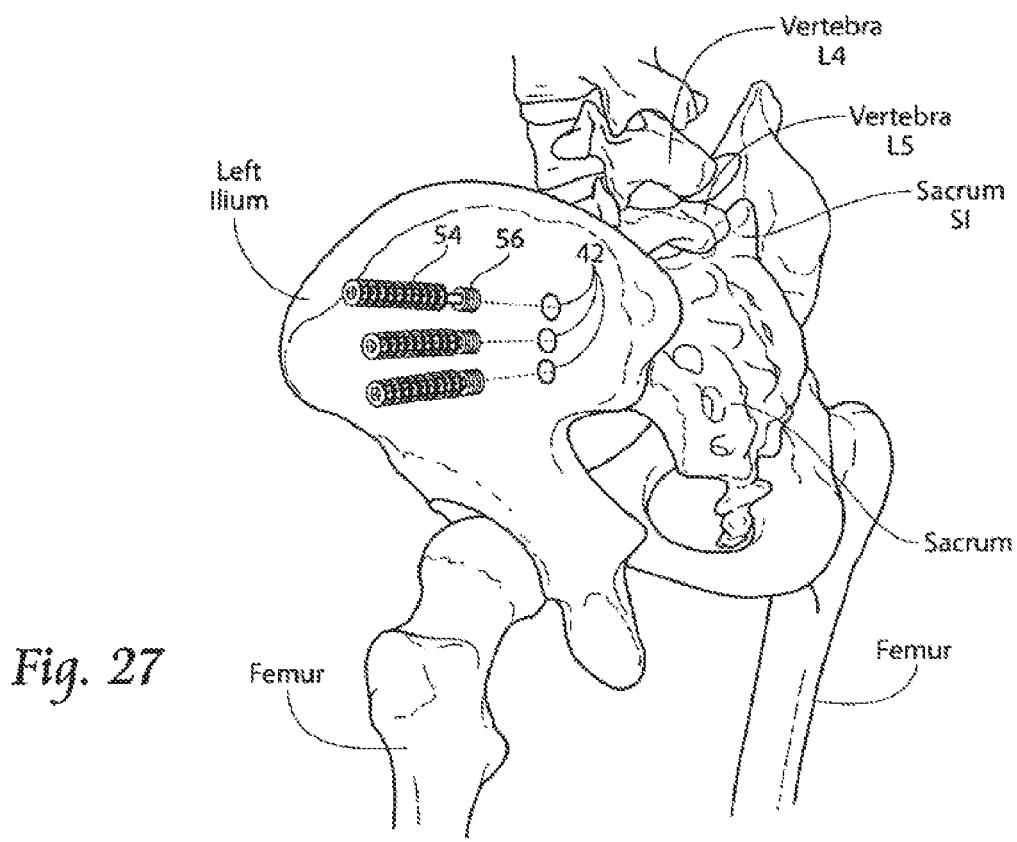
FIGS. 27 and 28A and 28B are anatomic views showing, respectively, in exploded perspective, assembled anterior view, and assembled axial section view, the implantation of a fusion cage structure for the fixation of the SI-Joint using a lateral approach laterally through the ilium, the SI-Joint, and into the sacrum S1.
Figure 28A:
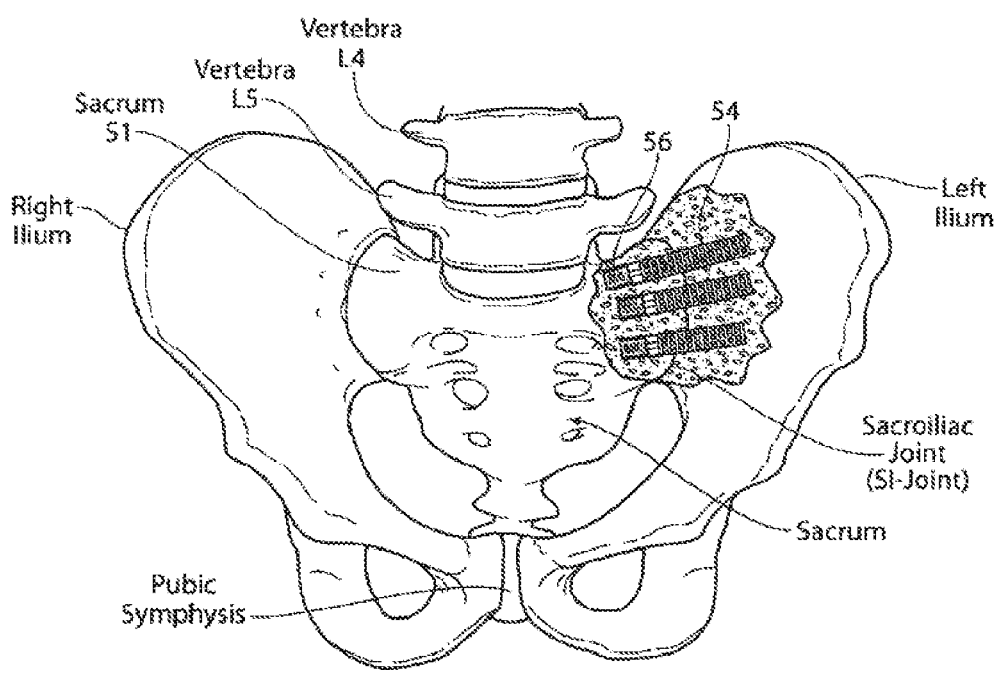
Figure 28B:
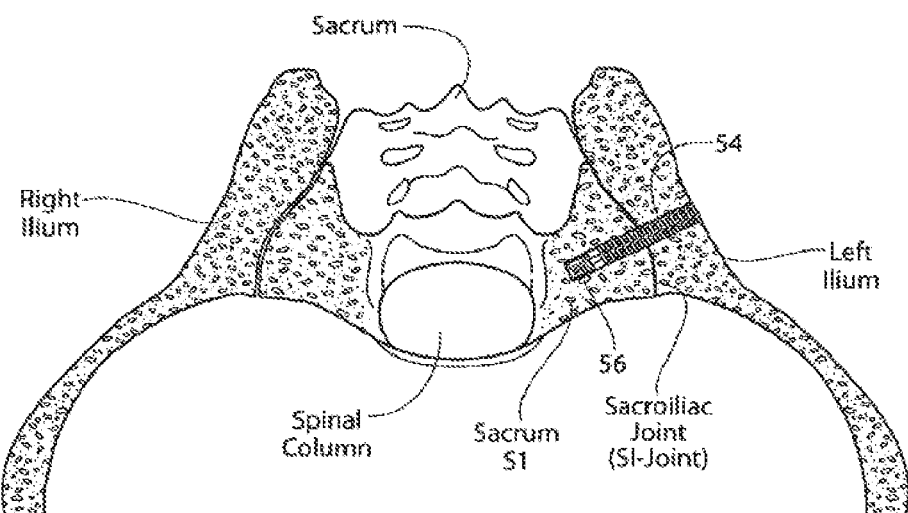

As another example, one or more fusion cage structures 54 containing bone graft material can be introduced using the lateral approach described herein, being placed laterally through the ilium, the SI-Joint, and into the sacrum S1. This path and resulting placement of the fusion cage structures 54 are shown in FIGS. 27 and 28A/B. Such a structure 54 may include an anchor screw component 56, to be seated in the sacrum S1, as shown in FIGS. 27 and 28A/B.

Figure 29:
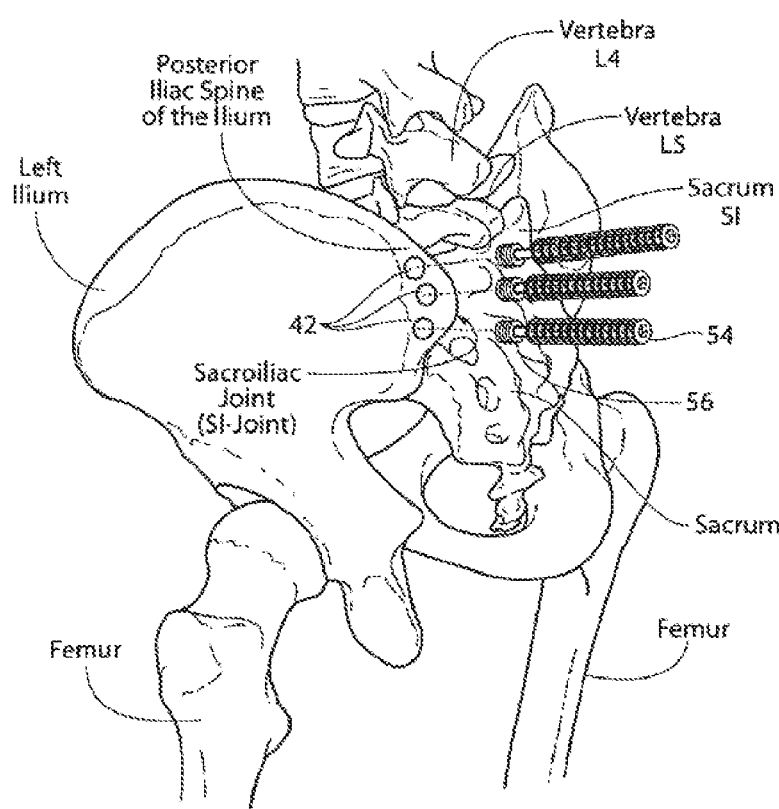
FIGS. 29 and 30A and 30B are anatomic views showing, respectively, in exploded perspective, assembled lateral view, and assembled axial section view, the implantation of a fusion cage structure for the fixation of the SI-Joint using a postero-lateral approach entering from the posterior iliac spine of the ilium, angling through the SI-Joint, and terminating in the sacral alae.
Figure 30A:
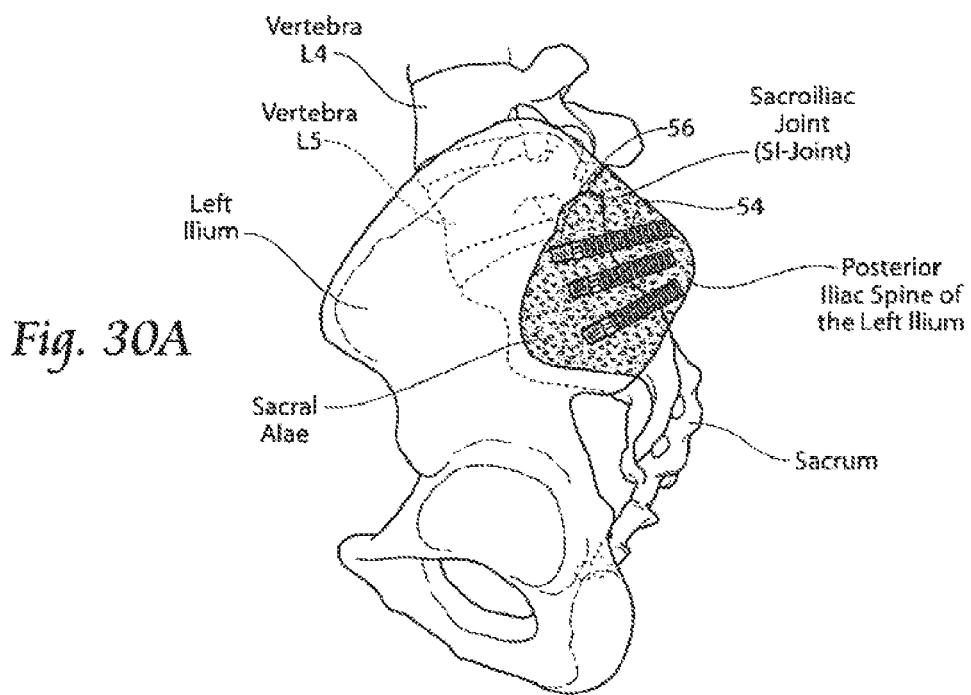
Figure 30B:
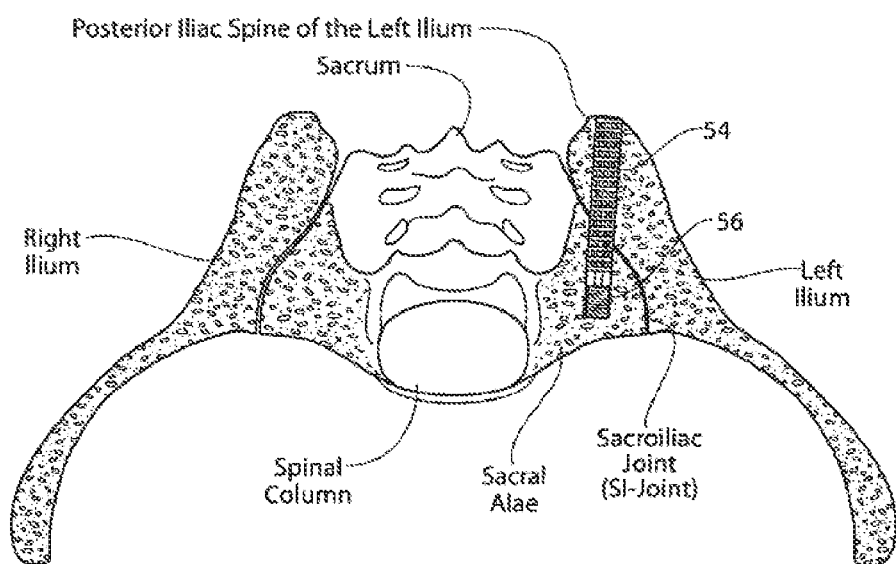

Likewise, one or more of the fusion cage structures 54 can be introduced using the postero-lateral approach described herein, entering from the posterior iliac spine of the ilium, angling through the SI-Joint, and terminating in the sacral alae. This path and resulting placement of the fusion cage structures 54 are shown in FIGS. 29 and 30A/B. Such a structure 54 may include an anchor screw component 56, to be seated in the sacral alae, as shown in FIGS. 27 and 28A/B.

IV. Conclusion

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

Part II

The following describes embodiments of the implant for the fusion or fixation of other joints or bone segments.

I. The Implant Structure

FIG. 40 shows a representative embodiment of an elongated, stem-like, cannulated implant structure 20. As will be described in greater detail later, the implant structure 20 is sized and configured for the fixation of bones which are to be fused (arthrodesed) (i.e. fixation of two or more individual bones that are adjacent and/or jointed) and/or the stabilization of adjacent bone structures. In particular, and as will be demonstrated, the implant structure is well suited for the fusion or stabilization of adjacent bone structures in the lumbar region of the spine, either across the intervertebral disc or across one or more facet joints.

The implant structure 20 can be formed—e.g., by machining, molding, or extrusion—from a durable material usable in the prosthetic arts that is not subject to significant bioabsorption or resorption by surrounding bone or tissue over time. The implant structure 20, is intended to remain in place for a time sufficient to stabilize a bone fracture or fusion site. Such materials include, but are not limited to, titanium, titanium alloys, tantalum, tivanium (aluminum, vanadium, and titanium), chrome cobalt, surgical steel, or any other total joint replacement metal and/or ceramic, sintered glass, artificial bone, any uncemented metal or ceramic surface, or a combination thereof.

Alternatively, the implant structure 20 may be formed from a suitable durable biologic material or a combination of metal and biologic material, such as a biocompatible bone-filling material. The implant structure 20 may be molded from a flowable biologic material, e.g., acrylic bone cement, that is cured, e.g., by UV light, to a non-flowable or solid material.

The implant structure 20 is sized according to the local anatomy. The morphology of the local structures can be generally understood by medical professionals using textbooks of human skeletal anatomy along with their knowledge of the site and its disease or injury. The physician is also able to ascertain the dimensions of the implant structure 20 based upon prior analysis of the morphology of the targeted bone region using, for example, plain film x-ray, fluoroscopic x-ray, or MRI or CT scanning.

As FIGS. 41 to 44 show, the implant structure 20 can take various shapes and have various cross-sectional geometries. The implant structure 20 can have, e.g., a generally curvilinear (i.e., round or oval) cross-section—as FIG. 41 shows for purposes of illustration—or a generally rectilinear cross section (i.e., square or rectangular or hexagon or H-shaped or triangular—as FIG. 42 shows for purposes of illustration—or combinations thereof. In FIG. 40, the implant structure 20 is shown to be triangular in cross section, which effectively resists rotation and micromotion once implanted.

As FIGS. 43 and 44 show, the implant structure 20, whether curvilinear (FIG. 43) or rectilinear (FIG. 44) can include a tapered region 34 at least along a portion of its axial length, meaning that the width or diameter of the implant structure 20 incrementally increases along its axial length. Desirably, the tapered region 34 corresponds with, in use, the proximal region of the implant structure 20 (i.e., the last part of the implant structure 20 to enter bone). The amount of the incremental increase in width or diameter can vary. As an example, for an implant structure 20 having a normal diameter of 7 mm, the magnitude of the incremental increase at its maximum can range between about 0.25 mm to 1.25 mm. The tapered region 34 enhances the creation and maintenance of compression between bone segments or regions.

As FIG. 40 shows, the implant structure 20 includes a region 24 formed along at least a portion of its length to promote bony in-growth onto or into surface of the structure and/or bony growth entirely through all or a portion of the structure. The bony in-growth or through-growth region 24 along the surface of the implant structure 20 accelerates bony in-growth or through-growth onto, into, or through the implant structure 20. Bony in-growth or through-growth onto, into, or through the implant structure 20 helps speed up the fusion process of the adjacent bone regions fixated by the implant structure 20.

The bony in-growth or through-growth region 24 desirably extends along the entire outer surface of the implant structure 20, as shown in FIGS. 40 to 44. The bony in-growth region 24 or through-growth can comprise, e.g., through holes, and/or various surface patterns, and/or various surface textures, and/or pores, or combinations thereof. The configuration of the bony in-growth or through-growth region 24 can, of course, vary. By way of examples, the bony in-growth or through-growth region 24 can comprise an open mesh configuration; or beaded configuration; or a trabecular configuration; or include holes or fenestrations. Any configuration conducive to bony in-growth and/or bony through-growth will suffice.

The bony in-growth or through-growth region 24 can be coated or wrapped or surfaced treated to provide the bony in-growth or through-growth region, or it can be formed from a material that itself inherently possesses a structure conducive to bony in-growth or through-growth, such as a porous mesh, hydroxyapetite, or other porous surface. The bony in-growth or through-growth region can includes holes that allow bone to grow throughout the region.

In a preferred embodiment, the bony in-growth region or through-growth region 24 comprises a porous plasma spray coating on the implant structure 20. This creates a biomechanically rigorous fixation/fusion system, designed to support reliable fixation/fusion and acute weight bearing capacity.

The bony in-growth or through-growth region 24 may further be covered with various other coatings such as antimicrobial, antithrombotic, and osteoinductive agents, or a combination thereof. The entire implant structure 20 may be impregnated with such agents, if desired.

The implant structure includes an interior bore that accommodates its placement in a non-invasive manner by sliding over a guide pin, as will be described in greater detail later.

As before stated, the implant structure 20 is well suited for the fusion and/or stabilization of adjacent bone structures in the lumbar region of the spine. Representative examples of the placement of the implant structure 20 in the lumbar region of the spine will now be described.

A. Use of the Implant Structures to Achieve Anterior Lumbar Interbody Fusion

Figure 45:
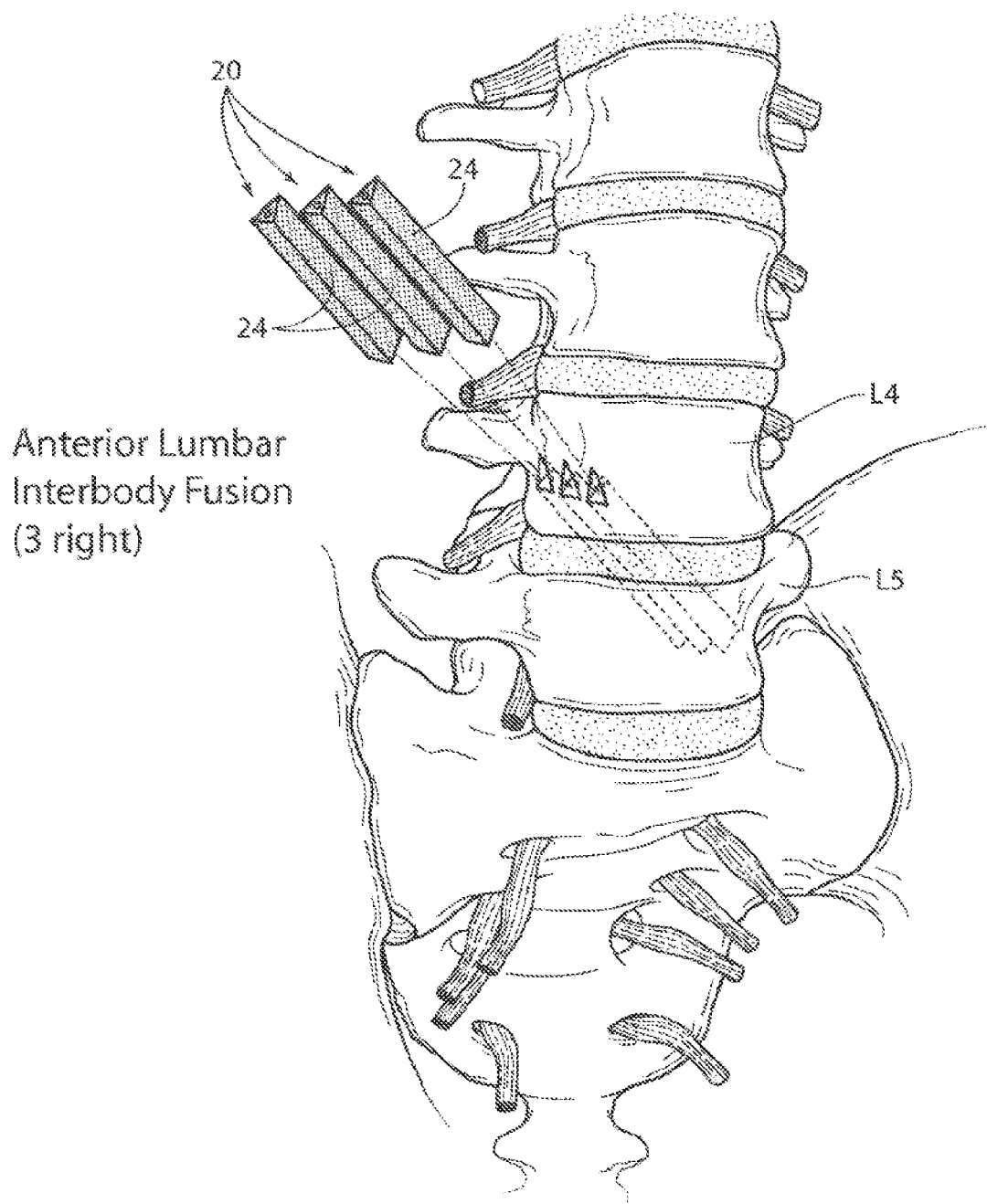
FIG. 45 is an anatomic anterior perspective view showing, in an exploded view prior to implantation, a representative configuration of an assembly of one or more implant structures as shown in FIG. 40, sized and configured to achieve anterior lumbar interbody fusion, in a non-invasive manner and without removal of the intervertebral disc.
Figure 46:
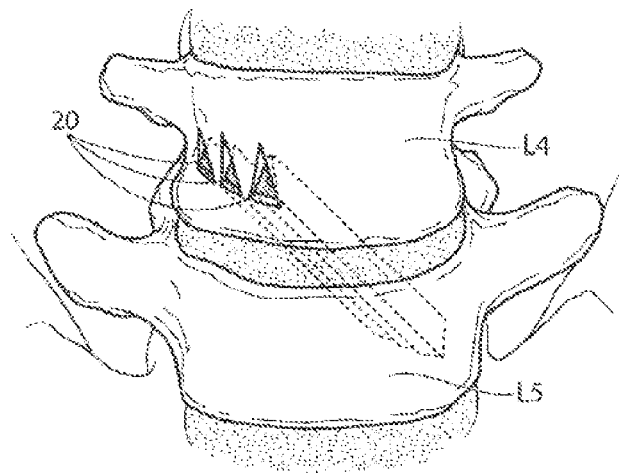
FIG. 46 is an anatomic anterior perspective view showing the assembly shown in FIG. 45 after implantation.
Figure 47:
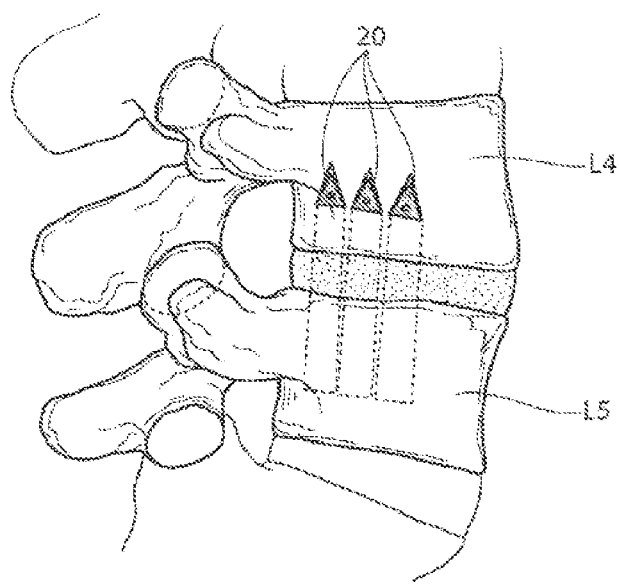
FIG. 47 is an anatomic right lateral perspective view showing the assembly shown in FIG. 45 after implantation.
Figure 48:
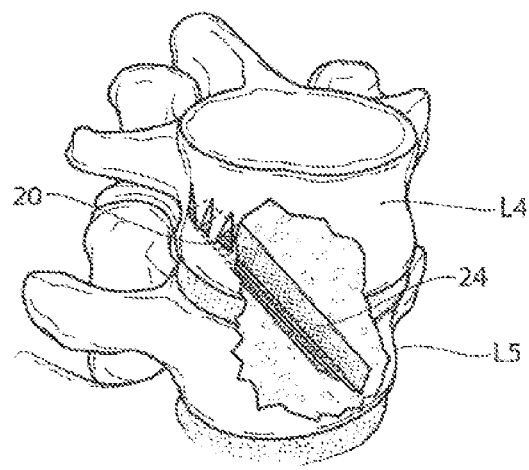
FIG. 48 is an anatomic superior left lateral perspective view showing the assembly shown in FIG. 45 after implantation.

FIG. 45 shows, in an exploded view prior to implantation, a representative configuration of an assembly of one or more implant structures 20 sized and configured to achieve anterior lumbar interbody fusion, in a non-invasive manner and without removal of the intervertebral disc. FIGS. 46 to 48 show the assembly after implantation, respectively, in an anterior view, a right lateral view, and a superior left lateral perspective view.

In the representative embodiment illustrated in FIGS. 46 to 48, the assembly comprises three implant structures 20. It should be appreciated, however, that a given assembly can include a greater or lesser number of implant structures 20.

In the representative embodiment shown in FIGS. 46 to 48, the three implant structures 20 are spaced in an adjacent lateral array. The implant structures 20 extend from an anterolateral region of a selected vertebral body (i.e., a lateral region anterior to a transverse process), across the intervertebral disc into an opposite anterolateral region of an adjacent caudal (inferior) vertebra. As shown in FIGS. 46 to 48, the array of implant structures 20 extends in an angled path (e.g., about 20.degree. to about 40.degree. off horizontal) through the cranial (superior) lumbar vertebral body (shown as L4) in an inferior direction, through the adjoining intervertebral disc, and terminates in the next adjacent caudal (inferior) lumbar vertebral body (shown as L5).

More particularly, in the representative embodiment shown in FIGS. 45 to 48, the implant structures 20 enter the right anterolateral region of vertebra L4 and terminate within the left anterolateral interior of vertebra L5, spanning the intervertebral disc between L4 and L5.

Alternatively, or in combination, an array of implant structures 20 can likewise extend between L5 and S1 in the same trans-disc formation.

The implant structures 20 are sized according to the local anatomy. The implant structures 20 can be sized differently, e.g., 3 mm, 4 mm, 6 mm, etc.), to accommodate anterolateral variations in the anatomy. The implant structures 20 can be sized for implantation in adults or children.

The intimate contact created between the bony in-growth or through-growth region 24 along the surface of the implant structure 20 accelerates bony in-growth or through-growth onto, into, or through the implant structure 20, to accelerate trans-disc fusion between these lumbar vertebrae.

FIGS. 49A to 49G diagrammatically show, for purposes of illustration, a representative lateral (or posterolateral) procedure for implanting the assembly of implant structures 20 shown in FIGS. 46 to 48.

The physician identifies the vertebrae of the lumbar spine region that are to be fused using, e.g., the Faber Test, or CT-guided injection, or X-ray/MRI of the lumbar spine. Aided by lateral and anterior-posterior (A-P) c-arms, and with the patient lying in a prone position (on their stomach), the physician makes a 3 mm incision laterally or postero-laterally from the side (see FIG. 49A). Aided by conventional visualization techniques, e.g., using X-ray image intensifiers such as a C-arms or fluoroscopes to produce a live image feed which is displayed on a TV screen, a guide pin 38 is introduced by conventional means into L4 (see FIG. 49B) for the first, most anterolateral implant structure (closest to the right transverse process of L4), in the desired angled inferiorly-directed path through the intervertebral disc and into the interior left anterolateral region of vertebra L5.

When the guide pin 38 is placed in the desired orientation, the physician desirable slides a soft tissue protector over the guide pin 38 before proceeding further. To simplify the illustration, the soft tissue protector is not shown in the drawings.

Figure 49A:
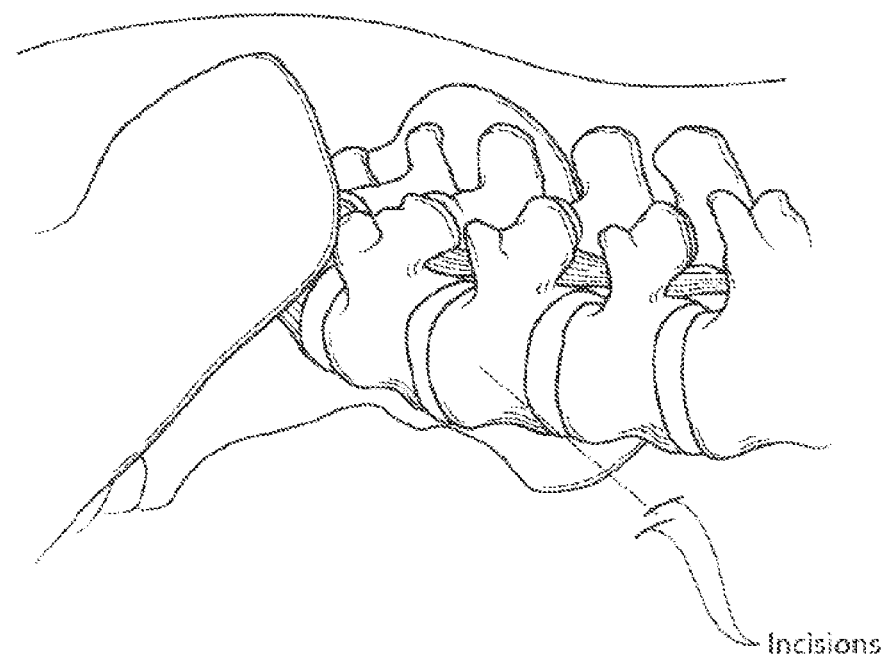
FIGS. 49A to 49G are diagrammatic views showing, for purposes of illustration, a representative lateral (or postero-lateral) procedure for implanting the assembly of implant structures shown in FIGS. 46 to 48.
Figure 49B:
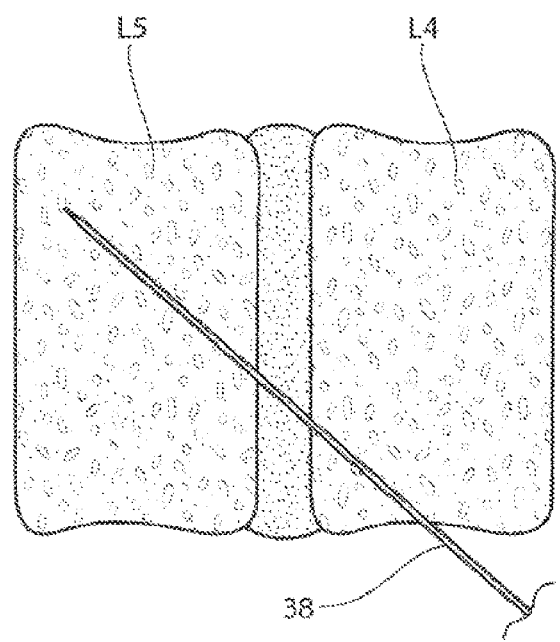
Figure 49C:
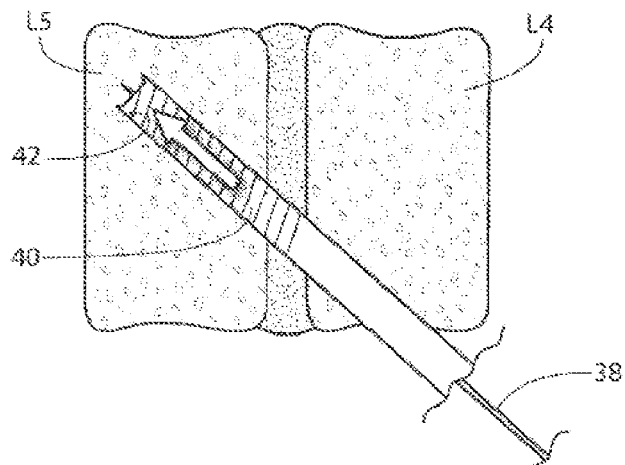
Figure 49D:
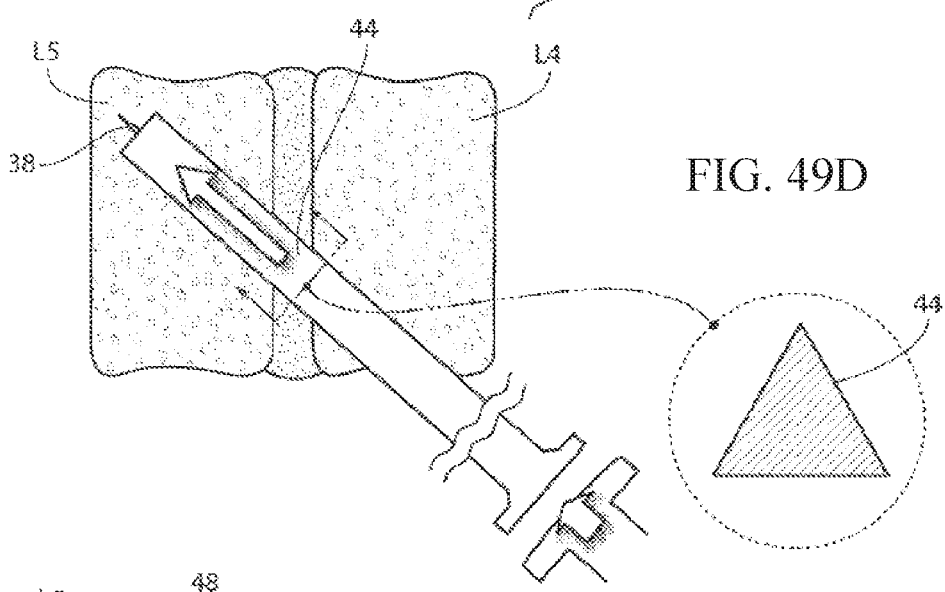
Figure 49E:
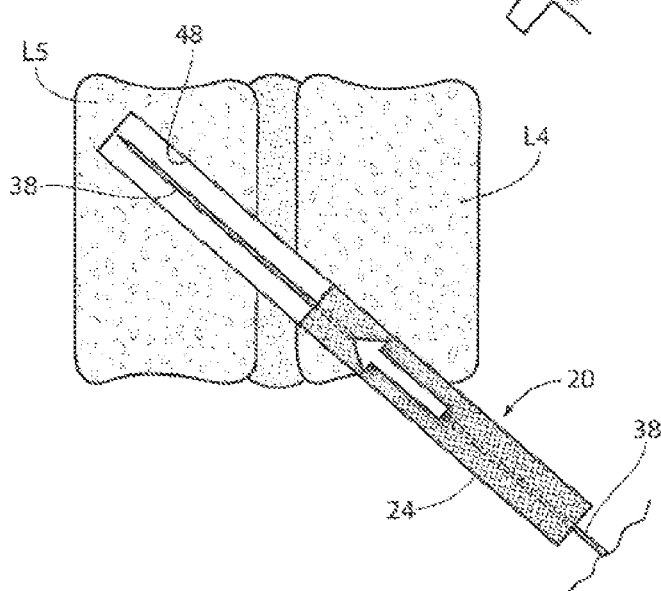

Through the soft tissue protector, a cannulated drill bit 40 is next passed over the guide pin 38 (see FIG. 49C). The cannulated drill bit 40 forms a pilot insertion path or bore 42 along the first angled path defined by the guide pin 38. A single drill bit or multiple drill bits 40 can be employed to drill through bone fragments or bone surfaces to create a pilot bore 42 of the desired size and configuration.

When the pilot bore 42 is completed, the cannulated drill bit 40 is withdrawn over the guide pin 38.

Through the soft tissue protector, a broach 44 having the external geometry and dimensions matching the external geometry and dimensions of the implant structure 20 (which, in the illustrated embodiment, is triangular) (see FIG. 49D) is tapped through the soft tissue protector over the guide pin 38 and into the pilot bore 42. The shaped broach 44 cuts along the edges of the pilot bore 42 to form the desired profile (which, in the illustrated embodiment, is triangular) to accommodate the implant structure 20.

The broach 44 is withdrawn (see FIG. 49E), and the first, most anterolateral implant structure 20 is passed over the guide pin 38 through the soft tissue protector into the broached bore 48. The guide pin 38 and soft tissue protector are withdrawn from the first implant structure 20.

Figure 49F:
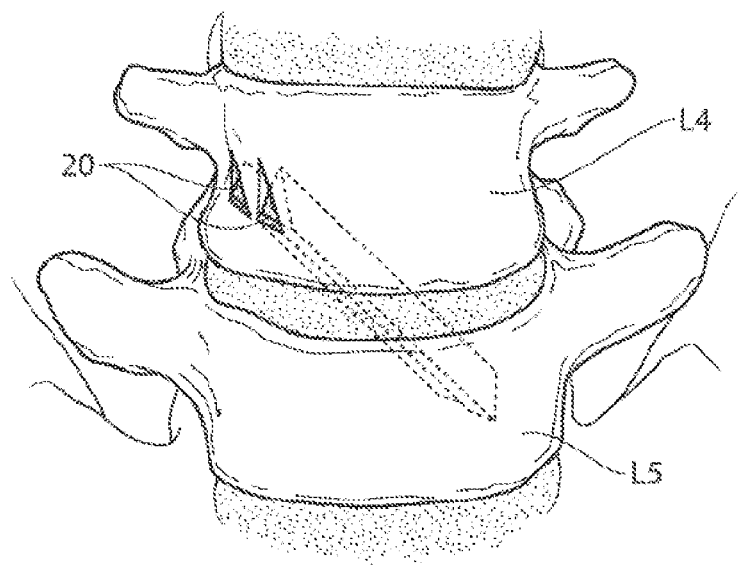
Figure 49G:
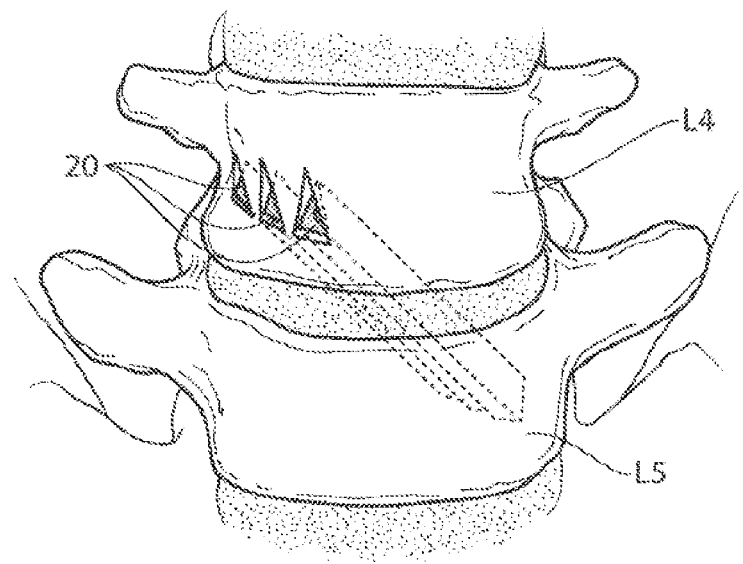

The physician repeats the above-described procedure sequentially for the next anterolateral implant structures 20: for each implant structure, inserting the guide pin 38, forming the pilot bore, forming the broached bore, inserting the respective implant structure, withdrawing the guide pin, and then repeating the procedure for the next implant structure, and so on until all implant structures 20 are placed (as FIGS. 49F and 49G indicate). The incision site(s) are closed.

In summary, the method for implanting the assembly of the implant structures 20 comprises (i) identifying the bone structures to be fused and/or stabilized; (ii) opening an incision; (iii) using a guide pin to established a desired implantation path through bone for the implant structure 20; (iv) guided by the guide pin, increasing the cross section of the path; (v) guided by the guide pin, shaping the cross section of the path to correspond with the cross section of the implant structure 20; (vi) inserting the implant structure 20 through the path over the guide pin; (vii) withdrawing the guide pin; (viii) repeating, as necessary, the procedure sequentially for the next implant structure(s) until all implant structures 20 contemplated are implanted; and (ix) closing the incision.

Figure 50:
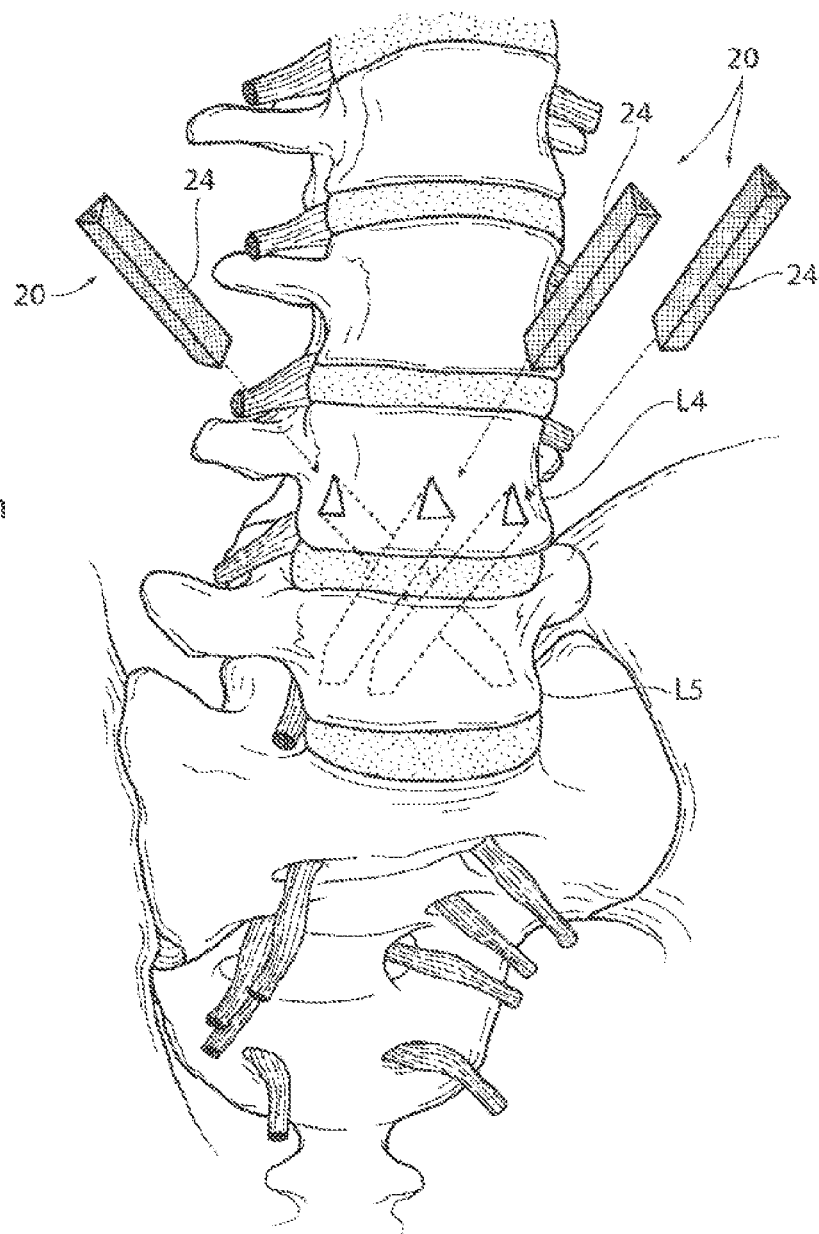
FIG. 50 is an anatomic anterior perspective view showing, in an exploded view prior to implantation, assemblies comprising one or more implant structures like that shown in FIG. 40 inserted from left and/or right anterolateral regions of a given lumbar vertebra, in an angled path through the intervertebral disc and into an opposite anterolateral interior region of the next inferior lumbar vertebra, FIG. 50 showing in particular two implant structures entering on the right anterolateral side of L4, through the intervertebral disc and into the left anterolateral region of L5, and one implant structure entering on the left anterolateral side of L4, through the intervertebral disc and into the right anterolateral region of L5, the left and right implant structures crossing each other in transit through the intervertebral disc.
Figure 51:
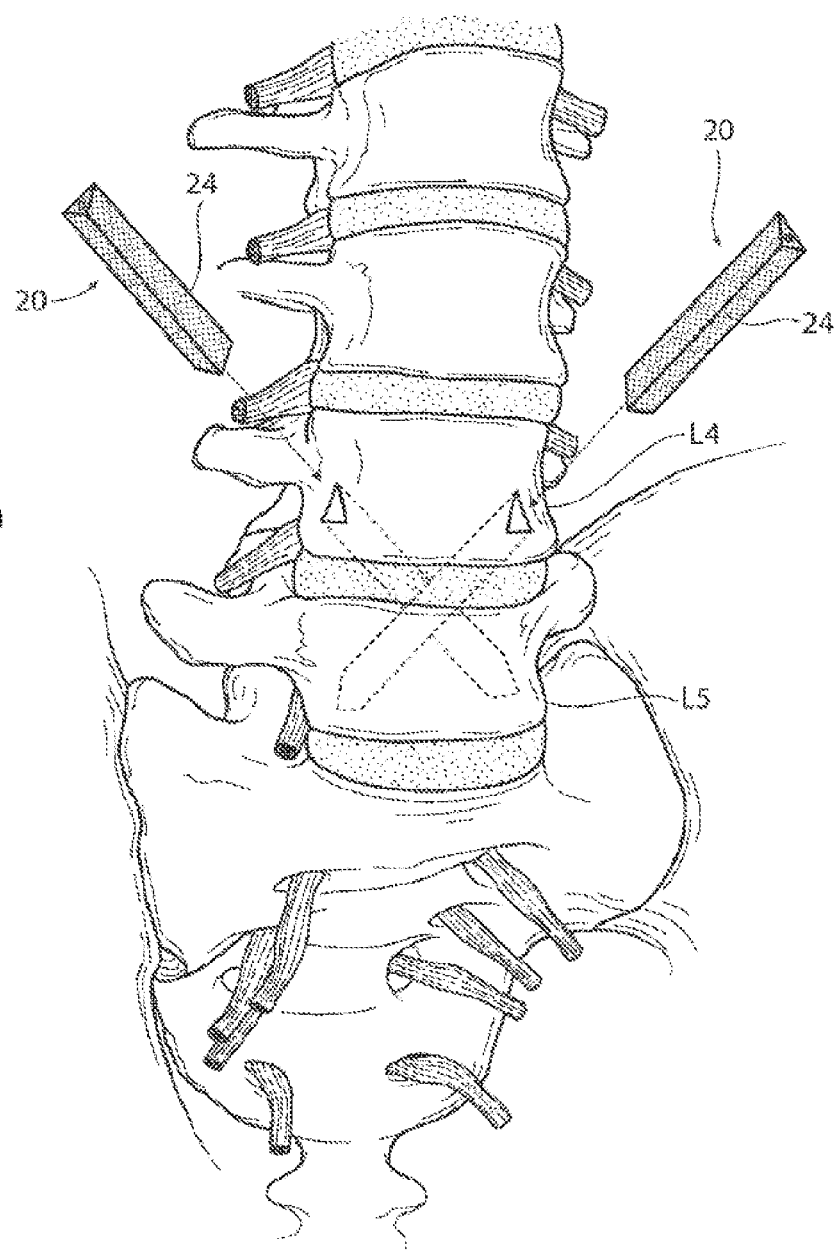
FIG. 51 is an anatomic anterior perspective view showing, in an exploded view prior to implantation, assemblies comprising one or more implant structures like that shown in FIG. 40 inserted from left and/or right anterolateral regions of a given lumbar vertebra, in an angled path through the intervertebral disc and into an opposite anterolateral interior region of the next inferior lumbar vertebra, FIG. 50 showing in particular one implant structure entering on the right anterolateral side of L4, through the intervertebral disc and into the left anterolateral region of L5, and one implant structure entering on the left anterolateral side of L4, through the intervertebral disc and into the right anterolateral region of L5, the left and right implant structures crossing each other in transit through the intervertebral disc.

As FIGS. 50 and 51 show, assemblies comprising one or more implant structures 20 can be inserted from left and/or right anterolateral regions of a given lumbar vertebra, in an angled path through the intervertebral disc and into an opposite anterolateral interior region of the next inferior lumbar vertebra.

For purposes of illustration, FIG. 50 shows two implant structures 20 entering on the right anterolateral side of L4, through the intervertebral disc and into the left anterolateral region of L5, and one implant structure 20 entering on the left anterolateral side of L4, through the intervertebral disc and into the right anterolateral region of L5. In this arrangement, the left and right implant structures 20 cross each other in transit through the intervertebral disc.

As another illustration of a representative embodiment, FIG. 51 shows one implant structure 20 entering on the right anterolateral side of L4, through the intervertebral disc and into the left anterolateral region of L5, and one implant structure 20 entering on the left anterolateral side of L4, through the intervertebral disc and into the right anterolateral region of L5. In this arrangement as well, the left and right implant structures 20 cross each other in transit through the intervertebral disc.

B. Use of Implant Structures to Achieve Translaminar Lumbar Fusion (Posterior Approach)

Figure 52:
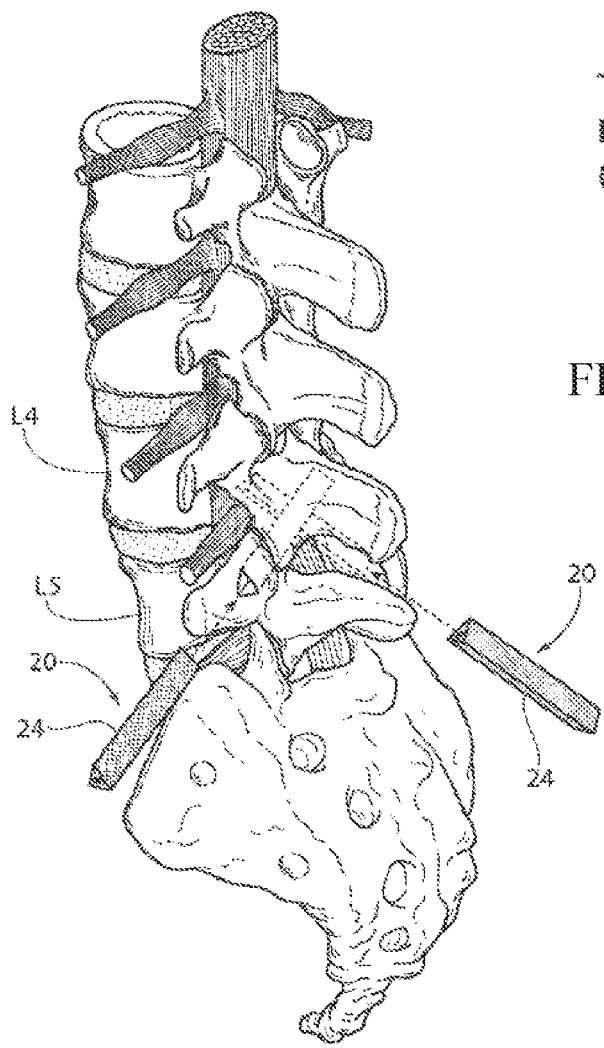
FIG. 52 is an anatomic posterior perspective view, exploded prior to implantation, of a representative configuration of an assembly of one or more implant structures like that shown in FIG. 40, sized and configured to achieve translaminar lumbar fusion in a non-invasive manner and without removal of the intervertebral disc.
Figure 53:
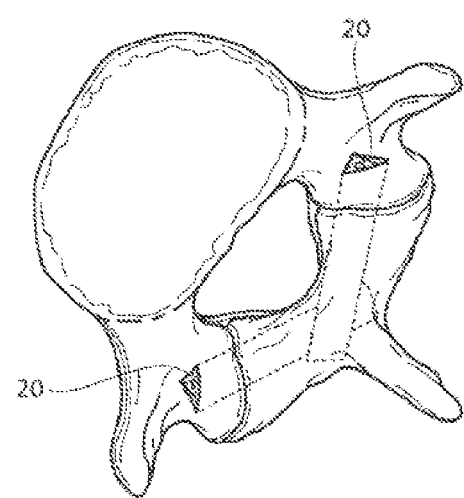
FIG. 53 is an anatomic inferior transverse plane view showing the assembly shown in FIG. 52 after implantation.

FIG. 52 shows, in an exploded view prior to implantation, a representative configuration of an assembly of one or more implant structures 20 sized and configured to achieve translaminar lumbar fusion in a non-invasive manner and without removal of the intervertebral disc. FIG. 53 shows the assembly after implantation, respectively, in an inferior transverse plane view.

As can be seen in the representative embodiment illustrated in FIGS. 52 and 53, the assembly comprises two implant structures 20. The first implant structure 20 extends from the left superior articular process of vertebra L5, through the adjoining facet capsule into the left inferior articular process of vertebra L4, and, from there, further through the lamina of vertebra L4 into an interior right posterolateral region of vertebra L4 adjacent the spinous process. The second implant structure 20 extends from the right superior articular process of vertebra L5, through the adjoining facet capsule into the right inferior articular process of vertebra L4, and, from there, further through the lamina of vertebra L4 into an interior left posterolateral region of vertebra L4 adjacent the spinous process. The first and second implant structures 20 cross each other within the medial lamina of vertebra L4.

The first and second implant structures 20 are sized and configured according to the local anatomy. The selection of a translaminar lumbar fusion (posterior approach) is indicated when the facet joints are aligned with the sagittal plane. Removal of the intervertebral disc is not required, unless the condition of the disc warrants its removal.

A procedure incorporating the technical features of the procedure shown in FIGS. 49A to 49G can be tailored to a posterior procedure for implanting the assembly of implant structures 20 shown in FIGS. 52 and 53. The method comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to established a desired implantation path through bone for the first (e.g., left side) implant structure 20, which, in FIGS. 52 and 53, traverses through the left superior articular process of vertebra L5, through the adjoining facet capsule into the left inferior articular process of vertebra L4, and then through the lamina of vertebra L4 into an interior right posterolateral region of vertebra L4 adjacent the spinous process. The method further includes (iv) guided by the guide pin, increasing the cross section of the path; (v) guided by the guide pin, shaping the cross section of the path to correspond with the cross section of the implant structure; (vi) inserting the implant structure 20 through the path over the guide pin; (vii) withdrawing the guide pin; and (viii) using a guide pin to established a desired implantation path through bone for the second (e.g., right side) implant structure 20, which, in FIGS. 52 and 53, traverses through the right superior articular process of vertebra L5, through the adjoining facet capsule into the right inferior articular process of vertebra L4, and through the lamina of vertebra L4 into an interior left posterolateral region of vertebra L4 adjacent the spinous process. The physician repeats the remainder of the above-described procedure sequentially for the right implant structure 20 as for the left, and, after withdrawing the guide pin, closes the incision.

The intimate contact created between the bony in-growth or through-growth region 24 along the surface of the implant structure 20 across the facet joint accelerates bony in-growth or through-growth onto, into, or through the implant structure 20, to accelerate fusion of the facets joints between L4 and L5. Of course, translaminar lumbar fusion between L5 and S1 can be achieved using first and second implant structures in the same manner.

C. Use of Implant Structures to Achieve Lumbar Facet Fusion (Posterior Approach)

FIG. 54 shows, in an exploded view prior to implantation, a representative configuration of an assembly of one or more implant structures 20 sized and configured to lumbar facet fusion, in a non-invasive manner and without removal of the intervertebral disc. FIGS. 55 and 56 show the assembly after implantation, respectively, in an inferior transverse plane view and a lateral view.

As can be seen in the representative embodiment illustrated in FIGS. 54 and 56, the assembly comprises two implant structures 20. The first implant structure 20 extends from the left inferior articular process of vertebra L4, through the adjoining facet capsule into the left superior articular process of vertebra L5 and into the pedicle of vertebra L5. The second implant structure 20 extends from the right inferior articular process of vertebra L5, through the adjoining facet capsule into the right superior articular process of vertebra L5 and into the pedicle of vertebra L5. In this arrangement, the first and second implant structures 20 extend in parallel directions on the left and right pedicles of vertebra L5. The first and second implant structures 20 are sized and configured according to the local anatomy. The selection of lumbar facet fusion (posterior approach) is indicated when the facet joints are coronally angled. Removal of the intervertebral disc is not necessary, unless the condition of the disc warrants its removal.

A procedure incorporating the technical features of the procedure shown in FIGS. 49A to 49G can be tailored to a posterior procedure for implanting the assembly of implant structures 20 shown in FIGS. 54 to 56. The method comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to established a desired implantation path through bone for the first (e.g., left side) implant structure 20, which, in FIGS. 54 to 56, traverses through the left inferior articular process of vertebra L4, through the adjoining facet capsule into the left superior articular process of vertebra L5 and into the pedicle of vertebra L5. The method further includes (iv) guided by the guide pin, increasing the cross section of the path; (v) guided by the guide pin, shaping the cross section of the path to correspond with the cross section of the implant structure 20; (vi) inserting the implant structure 20 through the path over the guide pin; (vii) withdrawing the guide pin; and (viii) using a guide pin to established a desired implantation path through bone for the second (e.g., right side) implant structure 20, which, in FIGS. 54 to 56, traverses through the right inferior articular process of vertebra L5, through the adjoining facet capsule into the right superior articular process of vertebra L5 and into the pedicle of vertebra L5. The physician repeats the remainder of the above-described procedure sequentially for the right implant structure 20 as for the left and, withdrawing the guide pin, closes the incision.

The intimate contact created between the bony in-growth or through-growth region 24 along the surface of the implant structure 20 across the facet joint accelerates bony in-growth or through-growth onto, into, or through the implant structure 20, to accelerate fusion of the facets joints between L4 and L5.

Of course, translaminar lumbar fusion between L5 and S1 can be achieved using first and second implant structures in the same manner.

D. Use of Implant Structures to Achieve Trans-Iliac Lumbar Fusion (Anterior Approach)

Figure 57A:
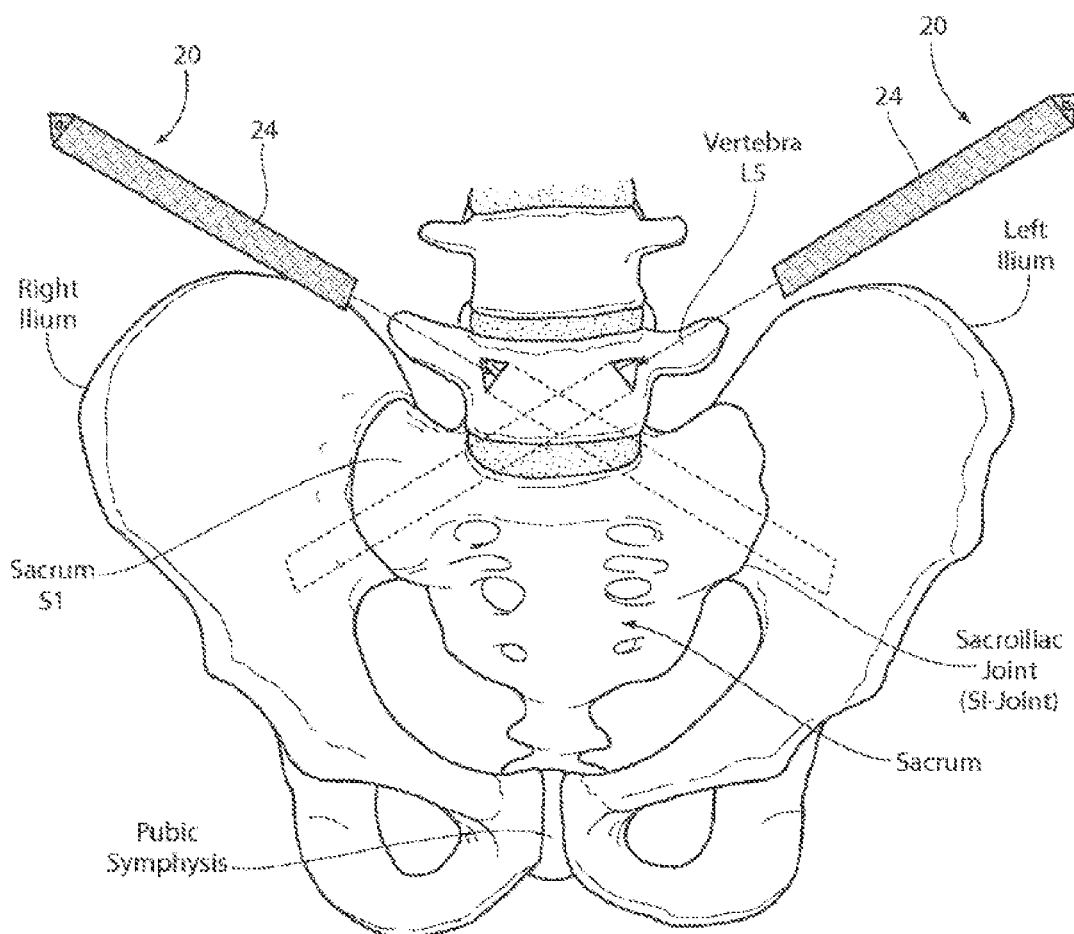
FIG. 57A is an anatomic anterior perspective view showing, in an exploded view prior to implantation, a representative configuration of an assembly of one or more implant structures like that shown in FIG. 40, sized and configured to achieve fusion between lumbar vertebra L5 and sacral vertebra S 1, in a non-invasive manner and without removal of the intervertebral disc, using an anterior approach.
Figure 57B:
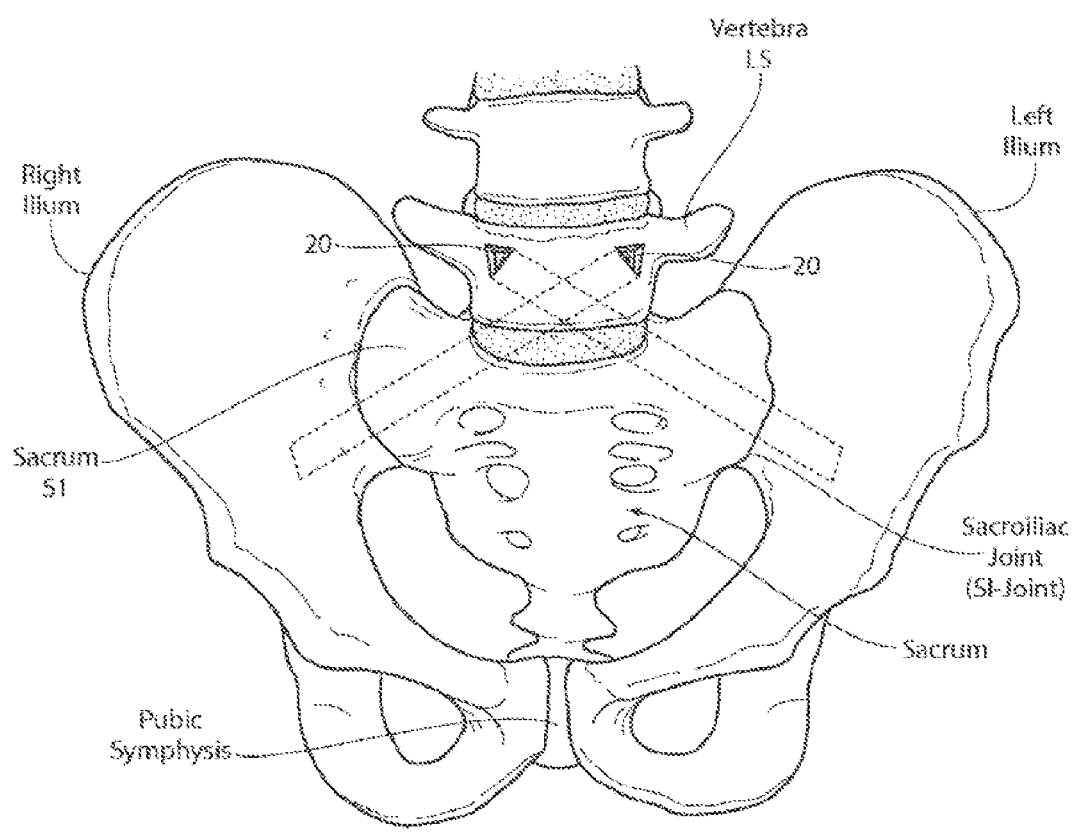
FIG. 57B is an anatomic anterior perspective view showing the assembly shown in FIG. 57A after implantation.

FIG. 57A shows, in an exploded view prior to implantation, a representative configuration of an assembly of one or more implant structures 20 sized and configured to achieve fusion between lumbar vertebra L5 and sacral vertebra S1, in a non-invasive manner and without removal of the intervertebral disc. FIG. 57B shows the assembly after implantation.

In the representative embodiment illustrated in FIGS. 57A and 57B, the assembly comprises two implant structures 20. It should be appreciated, however, that a given assembly can include a greater or lesser number of implant structures 20.

As FIGS. 57A and 57B show, the assembly comprises two implant structures 20 inserted from left and right anterolateral regions of lumbar vertebra L5, in an angled path (e.g., about 20.degree. to about 40.degree. off horizontal) through the intervertebral disc in an inferior direction, into and through opposite anterolateral interior regions of sacral vertebra S1, through the sacro-iliac joint, and terminating in the ilium. In this arrangement, the left and right implant structures 20 cross each other in transit through the intervertebral disc. As before described, the implant structures 20 are sized according to the local anatomy.

The intimate contact created between the bony in-growth or through-growth region 24 along the surface of the implant structure 20 accelerates bony in-growth or through-growth onto, into, or through the implant structure 20, to accelerate lumbar trans-iliac fusion between vertebra L5 and S1.

A physician can employ the lateral (or posterolateral) procedure as generally shown in FIGS. 49A to 49G for implanting the assembly of implant structures 20 shown in FIGS. 57A and 57B, including forming a pilot bore over a guide pin inserted in the angled path, forming a broached bore, inserting the right implant 20 structure, withdrawing the guide pin, and repeating for the left implant structure 20, or vice versa. The incision site(s) are closed.

The assembly as described makes possible the achievement of trans-iliac lumbar fusion using an anterior in a non-invasive manner, with minimal incision, and without necessarily removing the intervertebral disc between L5 and S1.

E. Use of Implant Structures to Achieve Trans-Iliac Lumbar Fusion (Postero-Lateral Approach from Posterior Iliac Spine)

Figure 58A:
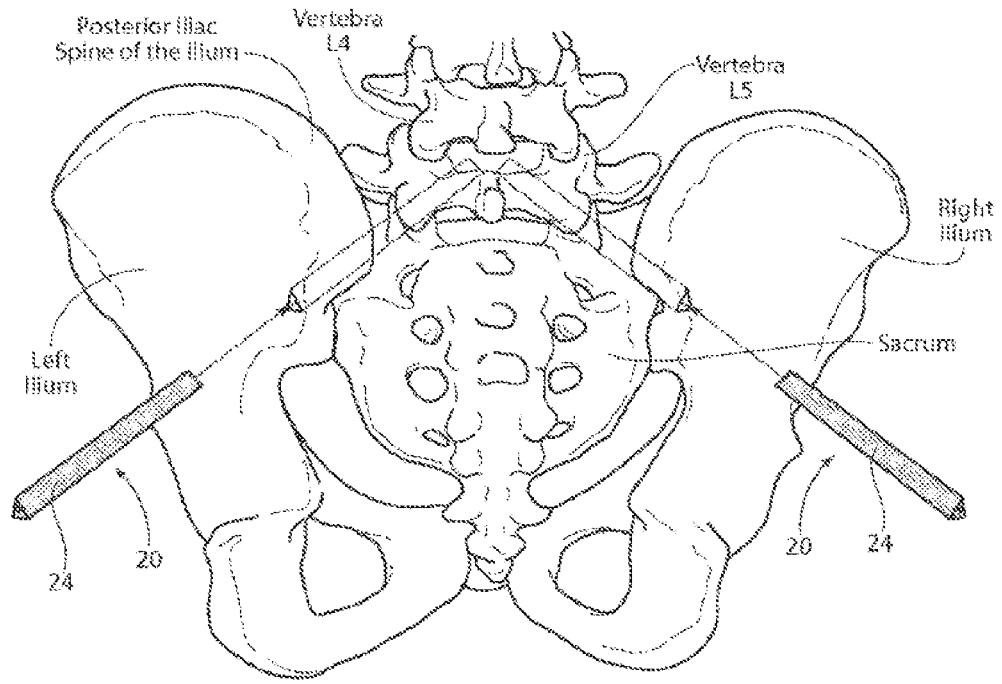
FIG. 58A is an anatomic posterior view showing, in an exploded view prior to implantation, another representative configuration of an assembly of one or more implant structures sized and configured to achieve fusion between lumbar vertebra L5 and sacral vertebra S1, in a non-invasive manner and without removal of the intervertebral disc, using a postero-lateral approach entering from the posterior iliac spine of the ilium, angling through the SI-Joint, and terminating in the lumbar vertebra L5.
Figure 58B:
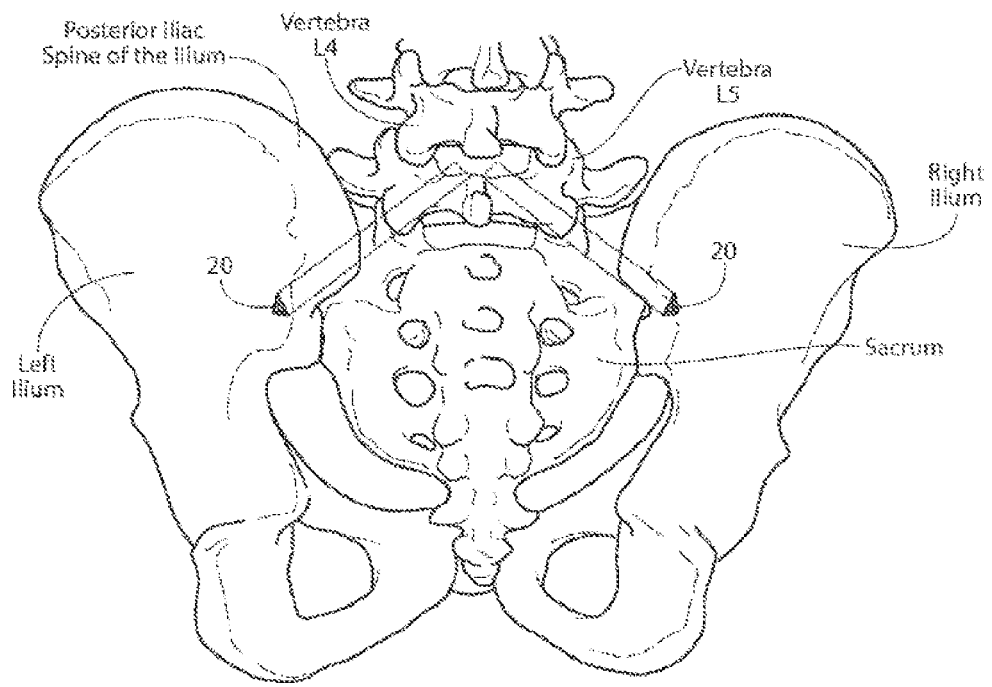
FIG. 58B is an anatomic posterior view showing the assembly shown in FIG. 58A after implantation.
Figure 58C:
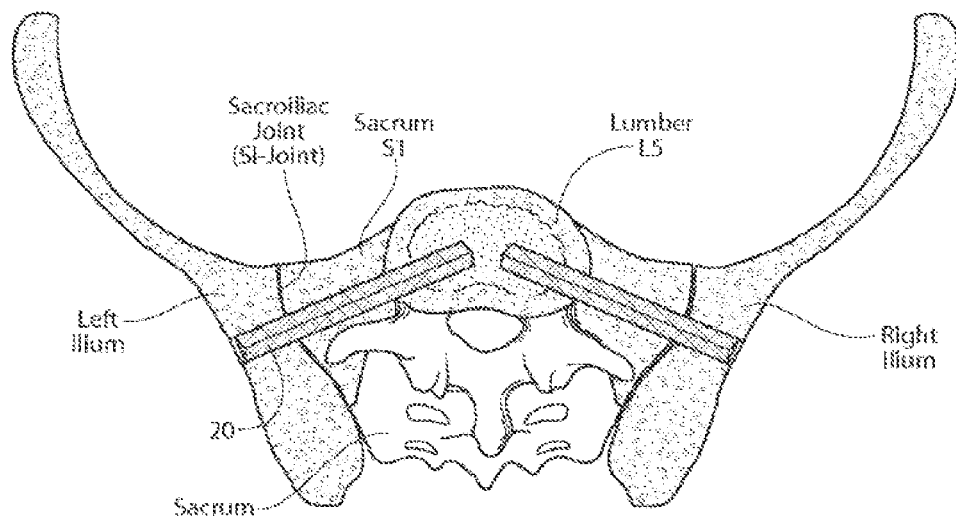
FIG. 58C is an anatomic superior view showing the assembly shown in FIG. 58B.

FIG. 58A shows, in an exploded view prior to implantation, another representative configuration of an assembly of one or more implant structures 20 sized and configured to achieve fusion between lumbar vertebra L5 and sacral vertebra S1, in a non-invasive manner and without removal of the intervertebral disc. FIGS. 58B and 58C show the assembly after implantation.

As FIGS. 58A and 58B show, the one or more implant structures are introduced in a postero-lateral approach entering from the posterior iliac spine of the ilium, angling through the SI-Joint into and through the sacral vertebra S1, and terminating in the lumbar vertebra L5. This path and resulting placement of the implant structures 20 are also shown in FIG. 58C. In the illustrated embodiment, two implant structures 20 are placed in this manner, but there can be more or fewer implant structures 20. Also in the illustrated embodiment, the implant structures 20 are triangular in cross section, but it should be appreciated that implant structures 20 of other cross sections as previously described can be used.

The postero-lateral approach involves less soft tissue disruption that the lateral approach, because there is less soft tissue overlying the entry point of the posterior iliac spine of the ilium. Introduction of the implant structure 20 from this region therefore makes possible a smaller, more mobile incision.

The set-up for a postero-lateral approach is generally the same as for a lateral approach. It desirably involves the identification of the lumbar region that is to be fixated or fused (arthrodesed) using, e.g., the Faber Test, or CT-guided injection, or X-ray/MRI of SI Joint. It is desirable performed with the patient lying in a prone position (on their stomach) and is aided by lateral and anterior-posterior (A-P) c-arms. The same surgical tools are used to form the pilot bore over a guide pin (e.g., on the right side), except the path of the pilot bore now starts from the posterior iliac spine of the ilium, angles through the SI-Joint, and terminates in the lumbar vertebra L5. The broached bore is formed, and the right implant 20 structure is inserted. The guide pin is withdrawn, and the procedure is repeated for the left implant structure 20, or vice versa. The incision site(s) are closed.

The assembly as described makes possible the achievement of trans-iliac lumbar fusion using a postero-lateral approach in a non-invasive manner, with minimal incision, and without necessarily removing the intervertebral disc between L5 and S1.

F. Use of Implant Structures to Stabilize a Spondylolisthesis

Figure 59:
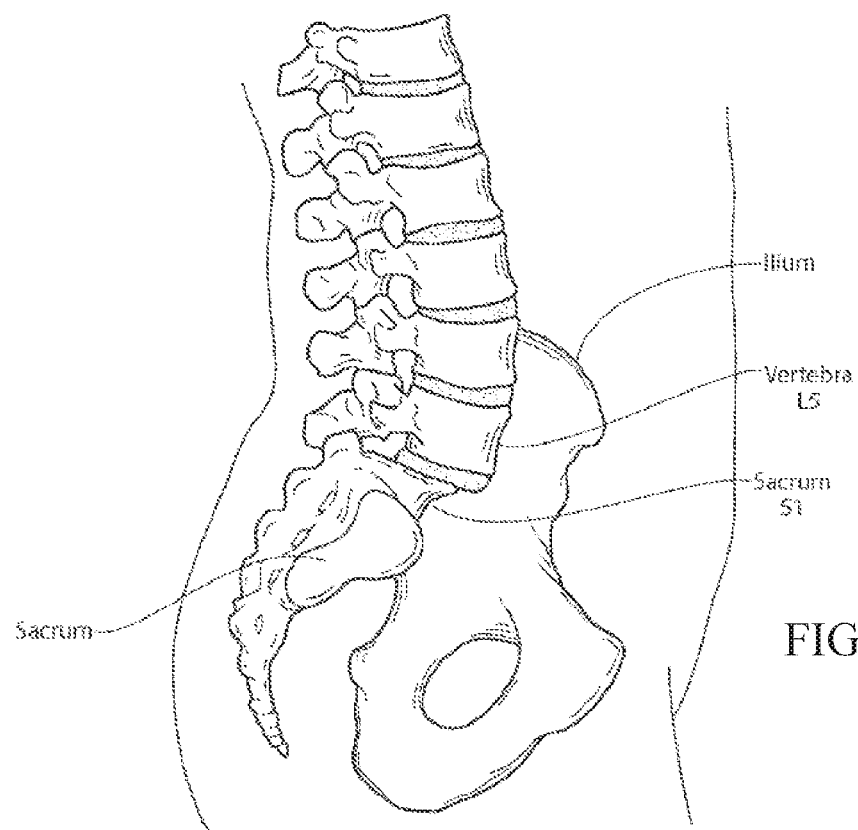
FIG. 59 is an anatomic lateral view showing a spondylolisthesis at the L5/S1 articulation, in which the lumbar vertebra L5 is displaced forward (anterior) of the sacral vertebra S 1.

FIG. 59 shows a spondylolisthesis at the L5/S1 articulation, in which the lumbar vertebra L5 is displaced forward (anterior) of the sacral vertebra S1. As FIG. 59 shows, the posterior fragment of L5 remains in normal relation to the sacrum, but the anterior fragment and the L5 vertebral body has moved anteriorly. Spondylolisthesis at the L5/S1 articulation can result in pressure in the spinal nerves of the cauda equine as they pass into the superior part of the sacrum, causing back and lower limb pain.

Figure 60A:
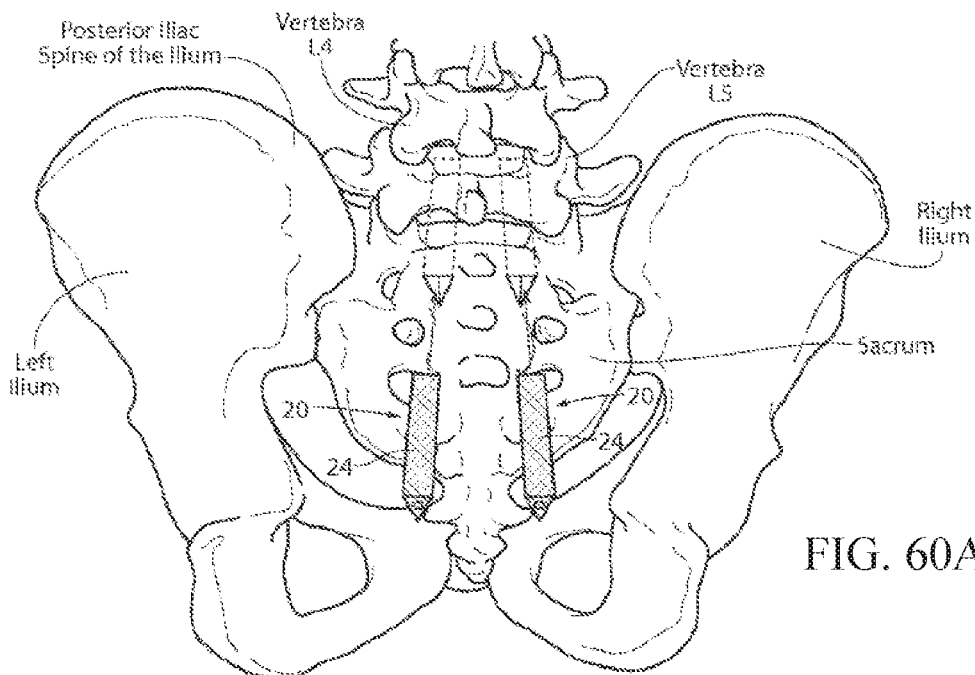
FIG. 60A is an anatomic anterior perspective view showing, in an exploded view prior to implantation, a representative configuration of an assembly of one or more implant structures like that shown in FIG. 40, sized and configured to stabilize a spondylolisthesis at the L5/S1 articulation.
Figure 60B:
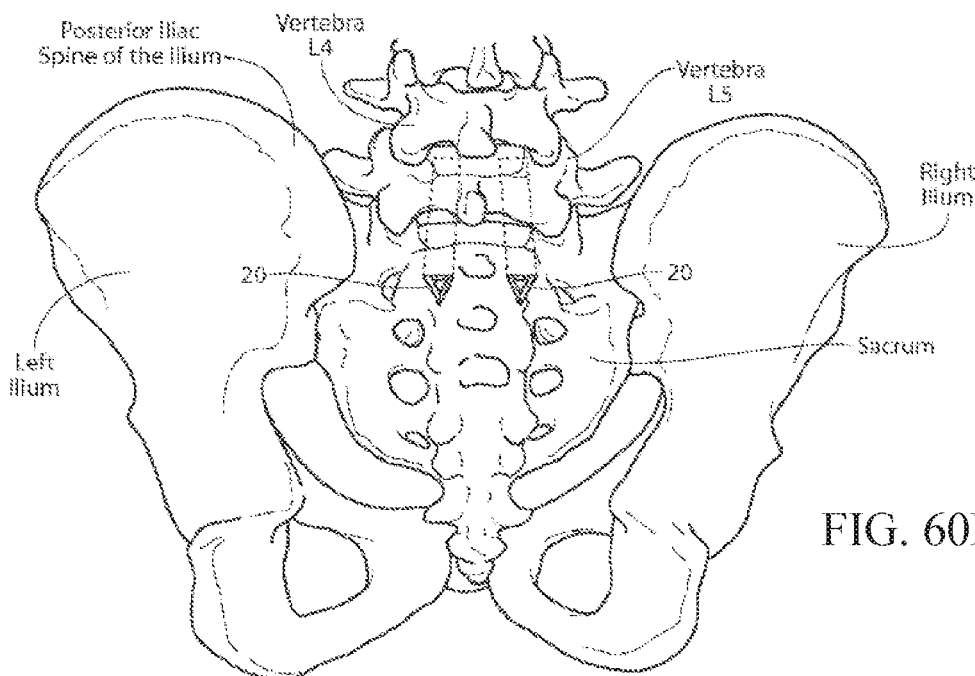
FIG. 60B is an anatomic anterior perspective view showing the assembly shown in FIG. 60A after implantation.
Figure 60C:
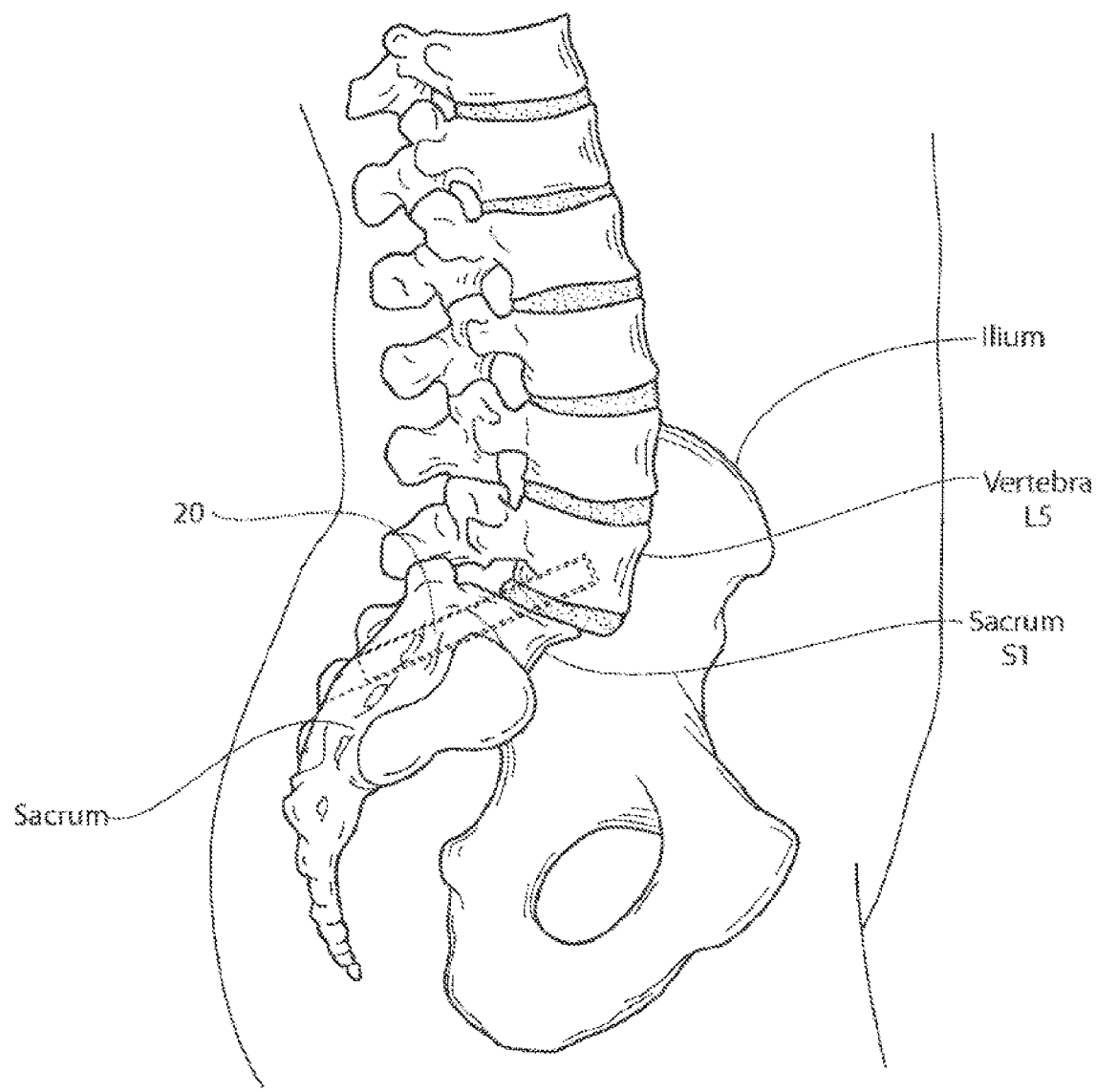
FIG. 60C is an anatomic lateral view showing the assembly shown in FIG. 60B.

FIG. 60A shows, in an exploded view prior to implantation, a representative configuration of an assembly of one or more implant structures 20 sized and configured to stabilize the spondylolisthesis at the L5/S1 articulation. FIGS. 60B and 60C show the assembly after implantation.

As shown, the implant structure 20 extends from a posterolateral region of the sacral vertebra S1, across the intervertebral disc into an opposite anterolateral region of the lumbar vertebra L5. The implant structure 20 extends in an angled path (e.g., about 20.degree. to about 40.degree. off horizontal) through the sacral vertebra S1 in a superior direction, through the adjoining intervertebral disc, and terminates in the lumbar vertebra L5.

A physician can employ a posterior approach for implanting the implant structure 20 shown in FIGS. 60A, 60B, and 60C, which includes forming a pilot bore over a guide pin inserted in the angled path from the posterior of the sacral vertebra S1 through the intervertebral disc and into an opposite anterolateral region of the lumbar vertebra L5, forming a broached bore, inserting the implant structure 20, and withdrawing the guide pin. The incision site is then closed. As previously described, more than one implant structure 20 can be placed in the same manner to stabilize a spondylolisthesis. Furthermore, a physician can fixate the implant structure(s) 20 using the anterior trans-iliac lumbar path, as shown in FIG. 57A/B or 58A/B/C.

The physician can, if desired, combine stabilization of the spondylolisthesis, as shown in FIGS. 60A/B/C, with a reduction, realigning L5 and S-1. The physician can also, if desired, combine stabilization of the spondylolisthesis, as shown in FIGS. 60 A/B/C (with or without reduction of the spondylolisthesis), with a lumbar facet fusion, as shown in FIGS. 54 to 56. The physician can also, if desired, combine stabilization of the spondylolisthesis, as shown in FIGS. 60A/B/C, with a decompression, e.g., by the posterior removal of the spinous process and laminae bilaterally.

II. Conclusion

The various representative embodiments of the assemblies of the implant structures 20, as described, make possible the achievement of diverse interventions involving the fusion and/or stabilization of lumbar and sacral vertebra in a non-invasive manner, with minimal incision, and without the necessitating the removing the intervertebral disc. The representative lumbar spine interventions described can be performed on adults or children and include, but are not limited to, lumbar interbody fusion; translaminar lumbar fusion; lumbar facet fusion; trans-iliac lumbar fusion; and the stabilization of a spondylolisthesis. It should be appreciated that such interventions can be used in combination with each other and in combination with conventional fusion/fixation techniques to achieve the desired therapeutic objectives.

Significantly, the various assemblies of the implant structures 20 as described make possible lumbar interbody fusion without the necessity of removing the intervertebral disc. For example, in conventional anterior lumbar interbody fusion procedures, the removal of the intervertebral disc is a prerequisite of the procedure. However, when using the assemblies as described to achieve anterior lumbar interbody fusion, whether or not the intervertebral disc is removed depends upon the condition of the disc, and is not a prerequisite of the procedure itself. If the disc is healthy and has not appreciably degenerated, one or more implant structures 20 can be individually inserted in a minimally invasive fashion, across the intervertebral disc in the lumbar spine area, leaving the disc intact.

In all the representative interventions described, the removal of a disc, or the scraping of a disc, is at the physician's discretion, based upon the condition of the disc itself, and is not dictated by the procedure.

The bony in-growth or through-growth regions 24 of the implant structures 20 described provide both extra-articular and intra osseous fixation, when bone grows in and around the bony in-growth or through-growth regions 24.

Conventional tissue access tools, obturators, cannulas, and/or drills can be used during their implantation. No disc preparation, removal of bone or cartilage, or scraping are required before and during formation of the insertion path or insertion of the implant structures 20, so a minimally invasive insertion path sized approximately at or about the maximum outer diameter of the implant structures 20 need be formed. Still, the implant structures 20, which include the elongated bony in-growth or through-growth regions 24, significantly increase the size of the fusion area, from the relatively small surface area of a given joint between adjacent bones, to the surface area provided by an elongated bony in-growth or through-growth regions 24. The implant structures 20 can thereby increase the surface area involved in the fusion and/or stabilization by 3-fold to 4-fold, depending upon the joint involved.

The implant structures 20 can obviate the need for autologous grafts, bone graft material, additional pedicle screws and/or rods, hollow modular anchorage screws, cannulated compression screws, cages, or fixation screws. Still, in the physician's discretion, bone graft material and other fixation instrumentation can be used in combination with the implant structures 20.

The implant structures 20 make possible surgical techniques that are less invasive than traditional open surgery with no extensive soft tissue stripping and no disc removal. The assemblies make possible straightforward surgical approaches that complement the minimally invasive surgical techniques. The profile and design of the implant structures 20 minimize rotation and micro-motion. Rigid implant structures 20 made from titanium provide immediate post-op fusion stability. A bony in-growth region 24 comprising a porous plasma spray coating with irregular surface supports stable bone fixation/fusion. The implant structures 20 and surgical approaches make possible the placement of larger fusion surface areas designed to maximize post-surgical weight bearing capacity and provide a biomechanically rigorous implant designed specifically to stabilize the heavily loaded lumbar spine.

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

What is claimed is:

1. A method of fusing a bone joint, the method comprising:
   identifying the bone joint to be fused, the bone joint comprising a first bone segment, a second bone segment, and a joint region located between the first and second bone segments;
   providing an elongated bone fixation/fusion implant having a longitudinal axis along a direction of elongation, and having a plurality of cross-sectional profiles transverse to the longitudinal axis, each of the plurality of cross-sectional profiles encompassing an entire cross-section of the implant and being at least partially defined by a plurality of longitudinal apices;
   inserting a distal end of the elongated implant in a direction along the longitudinal axis through the first bone segment, transversely across the joint region and at least partially into the second bone segment, wherein at least one of the plurality of cross-sectional profiles is completely surrounded by the first bone segment, and wherein at least one of the plurality of cross-sectional profiles is completely surrounded by the second bone segment; and
   implanting the elongated implant across the bone joint by leaving the elongated implant in place across the bone joint postoperatively.

2. The method of claim 1, further comprising creating a bore through the first bone segment, transversely across the joint region and at least partially into the second bone segment, wherein creating the bore occurs at a time before the inserting step.

3. The method of claim 2, wherein the bore has the same shape as the elongated implant.

4. The method of claim 2, further comprising, at a time after creating the bore and at a time before the inserting step, reshaping a profile of the bore.

5. The method of claim 1, wherein the providing step comprises providing the elongated implant with a cross-sectional profile defined by three longitudinal apices.

6. The method of claim 1, wherein the elongated implant is cannulated, having a central lumen extending therethrough to assist in the placement of the elongated implant within the bone segments.

7. The method of claim 6, further comprising placing a guide pin into the first and second bone segments.

8. The method of claim 7, further comprising introducing a cannulated drill bit over the guide pin to form an implant bore in the bone segments.

9. The method of claim 7, wherein the inserting step comprises sliding the elongated implant over the guide pin.

10. The method of claim 9, further comprising removing the guide pin from the bone segments after the elongated implant has been inserted into the bone segments.

11. The method of claim 1, wherein the providing step comprises providing the elongated implant with the cross-sectional profile defined by exactly three longitudinal apices.

12. The method of claim 1, wherein the elongated implant is cannulated, having a central lumen extending therethrough with an inside diameter matching a nominal outside diameter of a guide pin to assist in the placement of the elongated implant within the bone segments.

13. A method of fusing a bone joint, the method comprising:

identifying the bone joint to be fused, the bone joint comprising a first bone segment, a second bone segment, and a joint region located between the first and second bone segments;

providing an elongated bone fixation/fusion implant having a cross-sectional profile defined by a plurality of longitudinal apices;

inserting a distal end of the elongated implant first through the first bone segment, then transversely across the joint region and then at least partially into the second bone segment; and implanting the elongated implant across the bone joint by leaving the elongated implant in place across the bone joint postoperatively.

* * * * *

UNITED STATES PATENT AND TRADEMARK OFFICE
CERTIFICATE OF CORRECTION

| | |
|---|---|
| PATENT NO. | : 12,004,961 B2 |
| APPLICATION NO. | : 16/930174 |
| DATED | : June 11, 2024 |
| INVENTOR(S) | : Reiley |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 369 days.

Signed and Sealed this
Twelfth Day of August, 2025

Coke Morgan Stewart
*Acting Director of the United States Patent and Trademark Office*